(12) United States Patent
Coffin

(10) Patent No.: US 12,024,724 B2
(45) Date of Patent: *Jul. 2, 2024

(54) ONCOLYTIC VIRUS STRAIN

(71) Applicant: Replimune Limited, Oxfordshire (GB)

(72) Inventor: Robert Coffin, London (GB)

(73) Assignee: Replimune Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/817,618

(22) Filed: Aug. 4, 2022

(65) Prior Publication Data

US 2023/0130992 A1 Apr. 27, 2023

Related U.S. Application Data

(63) Continuation of application No. 16/740,203, filed on Jan. 10, 2020, now Pat. No. 11,473,063, which is a continuation of application No. 16/068,826, filed as application No. PCT/GB2017/050037 on Jan. 9, 2017, now Pat. No. 10,570,377.

(30) Foreign Application Priority Data

| Jan. 8, 2016 | (GB) | ..................................... | 1600380 |
| Jan. 8, 2016 | (GB) | ..................................... | 1600381 |
| Jan. 8, 2016 | (GB) | ..................................... | 1600382 |

(51) Int. Cl.
| *A61K 35/763* | (2015.01) |
| *A61K 39/395* | (2006.01) |
| *A61K 45/06* | (2006.01) |
| *A61P 35/00* | (2006.01) |
| *C07K 14/005* | (2006.01) |
| *C07K 14/535* | (2006.01) |
| *C07K 16/28* | (2006.01) |
| *C12N 7/00* | (2006.01) |
| *A61K 39/00* | (2006.01) |

(52) U.S. Cl.
CPC .............. *C12N 7/00* (2013.01); *A61K 35/763* (2013.01); *A61K 39/3955* (2013.01); *A61K 39/39558* (2013.01); *A61K 45/06* (2013.01); *A61P 35/00* (2018.01); *C07K 14/005* (2013.01); *C07K 14/535* (2013.01); *C07K 16/2818* (2013.01); *A61K 2039/505* (2013.01); *C12N 2710/16621* (2013.01); *C12N 2710/16622* (2013.01); *C12N 2710/16632* (2013.01); *C12N 2710/16633* (2013.01); *C12N 2710/16643* (2013.01); *C12N 2740/13022* (2013.01)

(58) Field of Classification Search
CPC ... A61K 35/763; A61P 35/00; C07K 14/5434; C07K 14/55; C07K 14/535; C12N 15/86; C12N 2710/16632; C12N 2710/16643
See application file for complete search history.

(56) References Cited

U.S. PATENT DOCUMENTS

| 5,122,458 A | 6/1992 | Post et al. |
| 5,168,062 A | 12/1992 | Stinski |
| 5,288,641 A | 2/1994 | Roizman |
| 5,328,688 A | 7/1994 | Roizman |
| 5,385,839 A | 1/1995 | Stinski |
| 5,599,691 A | 2/1997 | Roizman |
| 5,602,007 A | 2/1997 | Dunn et al. |
| 5,698,531 A | 12/1997 | Nabel et al. |
| 5,824,318 A | 10/1998 | Mohr et al. |
| 5,846,707 A | 12/1998 | Roizman |
| 6,040,169 A | 3/2000 | Brown et al. |
| 6,071,692 A | 6/2000 | Roizman |
| 6,120,773 A | 9/2000 | Roizman |
| 6,172,047 B1 | 1/2001 | Roizman et al. |
| 6,297,219 B1 | 10/2001 | Nabel et al. |
| 6,340,673 B1 | 1/2002 | Roizman et al. |
| 6,423,528 B1 | 7/2002 | Brown et al. |
| 6,428,968 B1 | 8/2002 | Molnar-Kimber et al. |
| 6,649,157 B2 | 11/2003 | Coffey et al. |
| 6,770,274 B1 | 8/2004 | Martuza et al. |
| 7,063,835 B2 | 6/2006 | Coffin |
| 7,223,593 B2 | 5/2007 | Coffin |
| 7,537,924 B2 | 5/2009 | Coffin |
| 7,749,745 B2 | 7/2010 | Johnson et al. |
| 7,981,669 B2 | 7/2011 | Coffin et al. |
| 8,273,568 B2 | 9/2012 | Martuza et al. |
| 8,277,818 B2 | 10/2012 | Coffin |

(Continued)

FOREIGN PATENT DOCUMENTS

| EP | 1235853 B1 | 7/2009 |
| JP | 2013511549 A | 4/2013 |

(Continued)

OTHER PUBLICATIONS

Carson et al., "Oncolytic Herpe Simplex Virus 1 (HSV-1) Vectors: Increasing Treatment Efficacy and Range Throught Strategic Virus Design", Drugs Future. 2010,35(3): 183-195.
Fransen et al., "Controlled Local Delivery of CTLA-4 Blocking Antibody Induces CD8+ T-Cell-Dependent Tumor Eradication and Decreaes Risk of Toxic Side Effects" Clin Cancer Res. 2013,19(19):5381-9.
Hooren et al., "Abstract B103: Intralesional administration of CTLA-4 blocking monoclonal antibodies as a means to optimize bladder cancer therapy", Cancer Immunol Res. 2016,4 (11_Supplement): B103.

(Continued)

*Primary Examiner* — Bao Q Li
(74) *Attorney, Agent, or Firm* — Norton Rose Fulbright US LLP

(57) ABSTRACT

The present invention relates to an oncolytic virus which is, or is derived from, a clinical isolate which has been selected by comparing the abilities of a panel of three or more clinical isolates of the same viral species to kill tumor cells of two or more tumor cell lines in vitro and selecting a clinical isolate which is capable of killing cells of two or more tumor cell lines more rapidly and/or at a lower dose in vitro than one or more of the other clinical isolates in the panel.

30 Claims, 33 Drawing Sheets

Specification includes a Sequence Listing.

(56) References Cited

U.S. PATENT DOCUMENTS

| | | | |
|---|---|---|---|
| 8,361,978 B2 | 1/2013 | Rabkin et al. | |
| 8,470,577 B2 | 6/2013 | Johnson et al. | |
| 8,679,830 B2 | 3/2014 | Coffin et al. | |
| 8,680,068 B2 | 3/2014 | Coffin | |
| 8,703,120 B2 | 4/2014 | Martuza et al. | |
| 8,871,193 B2 | 10/2014 | Johnson et al. | |
| 8,986,672 B2 | 3/2015 | Zhang et al. | |
| 9,487,581 B2 | 11/2016 | Abate et al. | |
| 9,492,482 B2 | 11/2016 | Beech et al. | |
| 9,827,307 B2 | 11/2017 | Rabkin et al. | |
| 9,868,961 B2 | 1/2018 | Allison et al. | |
| 10,039,796 B2 | 8/2018 | Zhang et al. | |
| 10,287,252 B2 | 5/2019 | Cowley et al. | |
| 10,301,600 B2 | 5/2019 | Coffin | |
| 10,570,377 B2 * | 2/2020 | Coffin | C07K 16/2818 |
| 10,612,005 B2 | 4/2020 | Coffin | |
| 10,626,377 B2 | 4/2020 | Coffin | |
| 10,765,710 B2 | 9/2020 | Zitvogel et al. | |
| 10,947,513 B2 | 3/2021 | Coffin | |
| 2003/0091537 A1 | 5/2003 | Coffin | |
| 2008/0014175 A1 | 1/2008 | Hallahan et al. | |
| 2010/0297072 A1 | 11/2010 | DePinho | |
| 2011/0044953 A1 | 2/2011 | Allison et al. | |
| 2013/0202639 A1 | 8/2013 | Kousoulas et al. | |
| 2014/0154216 A1 | 6/2014 | Coffin | |
| 2014/0271677 A1 | 9/2014 | Palese et al. | |
| 2015/0232812 A1 | 8/2015 | Coffin | |
| 2015/0283234 A1 | 10/2015 | Graziano et al. | |
| 2016/0040186 A1 | 2/2016 | Liu | |
| 2021/0252135 A1 | 8/2021 | Coffin | |

FOREIGN PATENT DOCUMENTS

| | | |
|---|---|---|
| JP | 2015/508156 A | 3/2015 |
| JP | 2016509045 A | 3/2016 |
| WO | 97/12623 A1 | 4/1997 |
| WO | 9830707 A2 | 7/1998 |
| WO | 2001/53505 A2 | 7/2001 |
| WO | 2001/53506 A2 | 7/2001 |
| WO | 2005/011715 A1 | 2/2005 |
| WO | 2006/002394 A2 | 1/2006 |
| WO | 2006/048749 A1 | 5/2006 |
| WO | 2007/052029 A1 | 5/2007 |
| WO | 2007/123737 A2 | 11/2007 |
| WO | 2010042189 A2 | 4/2010 |
| WO | 2011063309 A1 | 5/2011 |
| WO | 2011/118866 A1 | 9/2011 |
| WO | 2012/038606 A1 | 3/2012 |
| WO | 2013/038066 A1 | 3/2013 |
| WO | 2013112942 A1 | 8/2013 |
| WO | 2014/022138 A2 | 2/2014 |
| WO | 2014/036412 A2 | 3/2014 |
| WO | 2014/066532 A1 | 5/2014 |
| WO | 2014128235 A1 | 8/2014 |
| WO | 2015032755 A1 | 3/2015 |
| WO | 2015/059303 A1 | 4/2015 |
| WO | 2015/077624 A1 | 5/2015 |
| WO | 2015066042 A1 | 5/2015 |
| WO | 2015/128313 A1 | 9/2015 |
| WO | 2015/153417 A1 | 10/2015 |
| WO | 2016/008976 A1 | 1/2016 |
| WO | 2016/118865 A1 | 7/2016 |
| WO | 2017/118864 A1 | 7/2017 |
| WO | 2017/118866 A1 | 7/2017 |
| WO | 2017118867 A1 | 7/2017 |
| WO | 2017/181420 A1 | 10/2017 |
| WO | 2018127713 A1 | 7/2018 |

OTHER PUBLICATIONS

Hooren et al., "Local checkpoint inhibition of CTLA-4 as a monotherapy or in combination with anti-PD1 prevents the growth of murine bladder cancer" Eur J Immunol. 2017,47(2):385-393.

Marabelle et al., "Intratumoral Anti-CTLA-4 Therapy: Enhancing Efficacy While Avoiding Toxicity", Clin Cancer Res. 2013, 19(19):5261-3.

Annex A—WO 2017/118864—Figures 3 and 4 published Jul. 13, 2017.

Heinkoff and Heinkoff (1992) Proc. Natl. Acad. Sci. USA 89:10915-10919.

Herpesviridae Information from Virus Pathogen Resource (ViPR) retrieved on Nov. 4, 2021, available at: https://www.viprbrc.org/brc/aboutPathogen.spg7decoratoiHierpes.

Hetrologous Expression. In Binder, Hirokawa and Windorst (eds.)—Encyclopedia of Neuroscience. (2009) Springer, Berlin, Heidleberg Https://Doi.org/10.1007/978-3-540-29678-2_2190.

Hillier et al. Genomics in C. elegans: so many genes, such a little worm, 15 Genome Research 1651-60 (2005).

Ho et al. Unconventional viral gene expression mechanisms as therapeutic targets, 593 Nature 362-371 (May 2021).

Hoffmann et al. World J Gastroenterol. Jun. 14, 2007;13(22):3063-70.

Hoffmann et al. World J Gastroenterol. Mar. 28, 2008 14(12):1842-1850.

Hoggmann et al. W.J. G 2007, Jun. 14, 13 (22), pp. 3063-30700.

Hu et al. "A simplified system for generating oncolytic adenovirus vector carrying one or two transgenes", Cancer Gene Therapy (2008) 15, 173-182 r 2008 Nature Publishing Group.

Huang et al., Mol Ther, Feb. 2010, vol. 18, No. 2, pp. 264-274.

Hurwitz et al.: "CTLA-4 blockade synergizes with tumor-derived granulocyte-macrophage colony-stimulating factor for treatment of an experimental mammary carcinoma", Proc Natl Acad Sci USA, Aug. 18, 1998;95(17):10067-71.

IGI Global "What is Heterologous Expression" retrieved from https://www.igiglobal.com/dictionary/heterologousexpression/49470.

Inouye et al., "Codon optimization of genes for efficient protein expression in mammalian cells by selection of only preferred human codons", Protein Expression and Purification, 2015, 109:47-54.

International Search Report and Written Opinion issued in International Patent Application No. PCT/GB2017/050036, dated Apr. 26, 2017.

International Search Report and Written Opinion issued in International Patent Application No. PCT/GB2017/050037, dated Apr. 25, 2017.

International Search Report and Written Opinion issued in International Patent Application No. PCT/GB2017/050038, dated Apr. 24, 2017.

International Search Report for International Patent Application No. PCT/EP2015/066263, mailed from European Patent Office Oct. 7, 2015.

International Search Report for International Patent Application No. PCT/FI2009/051025, mailed from European Patent Office Mar. 24, 2010.

Ishihara et al. Systemic CD8+ T Cell-Mediated Tumoricidal Effects by Intratumoral Treatment of Oncolytic Herpes Simplex Virus with the Agonistic Monoclonal Antibody for Murine Glucocorticoid-Induced Tumor Necrosis Factor Receptor, 9(8) PLoS One e104669 (Aug. 2014).

Ishikawa et al. STING regulates intracellular DNA-mediated, type I interferon-dependent innate immunity, 461 Nature 788-792 (Oct. 8, 2009).

Jacobs et al. HSV-1 based vectors for gene therapy of neurological diseases and brain tumors Part II Vector Systems and Applications, 1(5) Neoplasia 402-416 (Nov. 1999).

Jacobs et al. Vaccinia Virus Vaccines: Past, Present and Future, 84(1) Antiviral Res. 1-13 (Oct. 2009).

John et al. Oncolytic Virus and Anti-4-IBB Combination Therapy Elicits Strong Antitumor Immunity against Established Cancer, 72(7) Cancer Research 1651-60 (Apr. 2012).

Kanagavelu et al PlosOne 2014, 9, 2, e90100.

Kanagavelu et al Vaccine 2012 30 691-701.

Karlin and Altschul (1993) Proc. Natl. Acad. Sci. USA 90:5873-5787.

Kasuya et al., Journal of Japan Surgical Society, 2006, 107, Extra Issue (2), p. 369, No. PS-005-8.

(56) References Cited

OTHER PUBLICATIONS

Kaufman et al: "Oncolytic viruses: a new class of immunotherapy drugs", Nat Rev Drug Discov, vol. 14, 642-662 (Sep. 2015).
Kaufmann et al. Chemovirotherapy of Malignant Melanoma with a Targeted and Armed Oncolytic Measles Virus, 133 Journal of Investigative Dermatology 1034-42 (2013).
Kelly and Russell, History of Oncolytic Viruses: Genesis to Genetic Engineering, 15(4) Molecular Therapy 651-659 (Apr. 2007).
Kim et al Cancer Res 2009, 69, 21, 8516-8525.
Kleinpeter et al. Vectorization in an oncolytic vaccinia virus of an antibody, a Fab and a scFv against programmed cell death-1 (PD-1) allows their intratumoral delivery and an improved tumor-growth inhibition, 5(10) Oncoimmunology e1220467 (2016).
Le Boeuf et al. Synergistic Interaction Between Oncolytic Viruses Augments Tumor Killing, 18(5) Molecular Therapy 888-895 (May 2010).
Lee et al. Enhanced Antitumor Effect of Oncolytic Adenovirus Expressing Interleukin-12 and B7-1in an Immunocompetent Murine Model, 12(19) Clin. Cancer Res. 5859-68 (Oct. 2006).
Lee et al.: "Oncolytic potential of E1B 55 kDa-deleted YKL-1 recombinant adenovirus: correlation with p53 functional status" Int J Cancer (2000) 88: 454-463.
Li et al. Int. J. Cancer 2008, 123: 493-499.
Li, B. et al: "Established B16 tumors are rejected following treatment with GM-CSF-secreting tumor cell immunotherapy In combination with anti-4-1 BB mAb", Clin Immunol. Oct. 2007;125(1):76-87.
Li, B. et al: "Anti-programmed death-1 synergizes with granulocyte macrophage colony-stimulating factor-secreting tumor cell immunotherapy providing therapeutic benefit to mice with established tumors", Clin Cancer Res. Mar. 1, 2009;15(5):1623-34.
Lipson and Drake, Ipilimumab: An Anti-CTLA-4 Antibody for Metastatic Melanoma, 17(22) Clin. Cancer Res. 6958-62 (Nov. 2011).
List of known isolates within each virus family extracted from NCBI Taxonomy Browser Output of Ex. 1023, dtd Nov. 3, 2021.
Liu et al., "ICP34.5 deleted herpes simplex cirus with enhanced oncolytic, immune stimulating, and anti-tumour properties," Gene Therapy, 2003, 10(4):292-303.
Loskog, Angelica, "Immunostimulatory Gene Therapy Using Oncolytic Viruses as Vehicles," Viruses, 2015, 7:5780-5791.
Lundstrom, New frontiers in oncolytic viruses: optimizing and selecting for virus strains with improved efficacy, 12 Biologics: Targets and Therapy 43-60 (2018).
Ma et al. Oncolytic herpes simplex virus and immunotherapy, 19 BMC Immunology 40 (2018).
Maclean et al., "Herpes simplex cirus type 1 deletion variants 1714 and 1716 pinpoint neurovirulence-related sequences in Glasgow strain 17 + between immediate early gene 1 and the 'a' sequence," Journal of General Virology, 1991, 72:631-639.
Majid et al. Recombinant Vesicular Stomatitis Virus (VSV) and Other Strategies in HCV Vaccine Designs and Immunotherapy. Tan SL, (Ed.) Hepatitis C Viruses: Genomes and Molecular Biology, Ch. 15. Norfolk (UK): Horizon Bioscience (2006).
Malhotra et al. Use of an Oncolytic Virus Secreting GM-CSF as Combined Oncolytic and Immunotherapy for Treatment of Colorectal and Hepatic Adenocarcinomas, 141(4) Surgery 520-529 (Apr. 2007).
McDonald et al. A measles virus vaccine strain derivative as a novel oncolytic agent against breast cancer, 99 Breast Cancer Research and Treatment 177-184 (2006).
Msaouel et al. Attenuated oncolytic measles Virus strains as cancer therapeutics, 13(9) Curr. Pharm. Biotechnol. 1732-41 (Jul. 1, 2012).
Murata et al: "X40 costimulation synergizes with GM-CSF whole-cell vaccination to overcome established CD8+ T cell tolerance to an endogenous tumor antigen", J Immunol. Jan. 15, 2006;176(2):974-83.
Fielding et al. "A hyperfusogenic gibbon apeleukemia envelope glycoprotein: targeting of a cytotoxic gene by ligand display", Hum Gene Ther. Apr. 10, 2000;11(6):817-26.
Ahlers et al: "A push-pull approach to maximize vaccine efficacy: abrogating suppression with an IL-13 inhibitor while augmenting help with granulocyte/macrophage colony-stimulating factor and CD40L", Proc Natl Acad Sci USA, Oct. 1, 2002;99(20):13020-5.
Ahmed et al, Intratumoral expression of a fusogenic membrane glycoprotein enhances the efficacy of replicating adenovirus therapy, 10 Gene Therapy 1663-71 (2003).
Allison et al., "For Their Discovery of Cancer Therapy by Inhibition of Negative Immune in Physiology of Medicine Regulation"; The Nobel Assembly at Karolinska Institutet; 2018 Nobel Prize.
Altschul, S F et al (1990) J Mol Biol 215:403-10.
Altschul, S.F. (1993) J Mol Evol 36:290-300.
Asada, Treatment of Human Cancer with Mumps Virus, 34(6) Cancer 1907-28 (Dec. 1974).
Assal et al: "Emerging targets in cancer immunotherapy: beyond CTLA-4 and PD-1", Immunotherapy. 2015;7 (11): 1169-86.
Balvay et al. Translational control of retroviruses, 5 Nature Reviews Microbiology 128-140 (Feb. 2007).
Bateman et al. Cancer Res. Mar. 15, 2000;60(6): 1492-7.
Bateman et al. Cancer Res. Nov. 15, 2002;62(22):6566-78.
Bauzon and Hermiston, 2014. Front. Immunol., 5(74): 1-10.
Belsham and Sonenberg, RNA-protein interactions in regulation of picornavirus RNA translation, 60(3) Microbiological Reviews 499-511 (Sep. 1996).
Bett et al. Packaging capacity and stability of human adenovirus type 5 vectors, 67(10) J. Virol. 5911-21 (Oct. 1993).
Blast analysis (publicly available through the National Centre for Biotechnology Information—http://www.ncbi.nlm.nih.gov/).
Blechacz et al. Engineered Measles Virus as a Novel Oncolytic Viral Therapy System for Hepatocellular Carcinoma, 44 (6) HEPATOLOGY 1465-77 (Dec. 2006).
Brochu-Lafontaine and Lemay, Addition of exogenous polypeptides on the mammalian reovirus outer capsid using reverse genetics, 179 J. Virol. Methods 342-350 (2012).
Capece et al: "Targeting costimulatory molecules to improve anti-tumor immunity", J Biomed Biotechnol, 2012; 2012:926321.
Carter et al. Identification of an overprinting gene in Merkel cell polyomavirus provides evolutionary insight into the birth of viral genes, 110(31) Proceedings of the National Academy of Sciences 12744-49 (Jul. 2013).
Cell Signaling Technology; Immune Checkpoint Signaling in the Tumor Microenvironment1; Mar. 2018.
Chen et al., "Dual silencing of Bcl-2 and Survivin by HSV-1 vector shows better antitumor efficacy in higher PKR phosphorylation tumor cells in vitro and in vivo", Cancer Gene Ther 22, 380-386; 2015.
Choi et al. Polymeric oncolytic adenovirus for cancer gene therapy, 219 Journal of Controlled Release 181-191 (2015).
Choi et al., "Concurrent delivery of GM-CSF and B7-1 using an oncolytic adenovirus elicits potent antitumor effect", Gene Therapy (2006) 13, 1010-1020 & 2006 Nature Publishing Group.
Choi et al., "Strengthening of antitumor immune memory and prevention of thymic atrophy mediated by adenovirus expressing IL-12 and GM-CSF", Gene Therapy (2012) 19, 711-723 & 2012 Macmillan Publishers.
Chou et al., "Mapping of Herpes Simplex Virus-1 Neurovirulence to ?134.5, a Gene Nonessential for Growth in Culture," Science, 1990, 250(4985):1262-1266.
Compilation of Virus Information from Swiss Institute of Bioinformatics retrieved on Nov. 3, 2021, available at https://viralzone.expasy.org/.
Croyle et al. PEGylation of a Vesicular Stomatitis Virus G Pseudotyped Lentivirus Vector Prevents Inactivation in Serum, 78(2) Journal of Virology 912-921 (Jan. 2004).
Danthinne and Imperiale, Production of first generation adenovirus vectors: a review, 7 Gene Therapy 1707-14 (2000).
Declaration of Dr. Sylvia D. Hall-Ellis dated Nov. 29, 2021 and Curriculum vitae.
Declaration of John C. Bell, Ph.D. dated Dec. 14, 2021 and Curriculum vitae.
Deguchi et al. Combination of the Tumor Angiogenesis Inhibitor Bevacizumab and Intratumoral Oncolytic Herpes Virus Injections as

(56) References Cited

OTHER PUBLICATIONS a Treatment Strategy for Human Gastric Cancers, 59(118) Hepatogastroenterology 1844-50 (Sep. 2012).
Devereux et al (1984) Nucleic Acids Research 12, p. 387-395.
Dias et al., 2012. Gene Ther., 19: 988-998.
Diefenbach et al., "Oncolytic virotherapy using herpes simplex virus: how far have we come?" Oncolytic Virotherapy, Nov. 1, 2015 (Nov. 1, 2015), p. 207.
Dikstein, The unexpected traits associated with core promoter elements, 2(5) Transcription 201-206 (Sep. 2011).
Documents filed on Jul. 9, 2018 in U.S. Appl. No. 16/068,830, including original application, preliminary amendment, application data sheet, search report, and transmittal form.
Donovan-Banfield et al. Deep splicing plasticity of the human adenovirus type 5 transcriptome drives virus evolution, 3 Communications Biology (2020) 124.
Du et al. "Tumor-specific oncolytic adenoviruses expressing granulocyte macrophage colony-stimulating factor or anti-CTLA4 antibody for the treatment of cancers", Cancer Gene Therapy, vol. 21, No. 8, Jul. 18, 2014 (Jul. 18, 2014), pp. 340-348.
Ebert et al. Syncytia Induction Enhances the Oncolytic Potential of Vesicular Stomatitis Virus in Virotherapy for Cancer, 64 Cancer Research 3265-3270 (May 2004).
Engeland et al. CTLA-4 and PD-L1 Checkpoint Blockade Enhances Oncolytic Measles Virus Therapy, 22(11) Molecular Therapy 1949-59 (Nov. 2014).
Excerpts from S. Baron (Ed.), Medical Microbiology, 4th. Ed. University of Texas Medical Branch at Galveston (1996).
Fu et al. Expression of a Fusogenic Membrane Glycoprotein by an Oncolytic Herpes Simplex Virus Potentiates the Viral Antitumor Effect, 7(6) Molecular Therapy 748-754 (Jun. 2003).
Fukuhara et al. Triple Gene-Deleted Oncolytic Herpes Simplex Virus Vector Double-Armed with Interleukin 18 and Soluble B7-1 Constructed by Bacterial Artificial Chromosome-Mediated System, 65(23) Cancer Res. 10663-68 (Dec. 2005).
Gangi et al., "The safety of talimogene laherparepvec for the treatment of advanced melanoma", Expert Opinion on Drug Safety, Dec. 28, 2016 (Dec. 28, 2016), pp. 1-5.
Gao et al: "Recombinant vesicularm stomatitis virus targeted to Her2/neu combined with anti-CTLA4 antibody eliminates implanted mammary tumors", Cancer Gene Ther. Jan. 2009;16(1):44-52.
Gibney et al., "Preliminary results from a phase 'A study of INCB024360 combined with ipilimumab (ipi) in patients (pts) with melanoma." 2014 ASCO Annual Meeting, No. 3010.
Grandi, et al., Cancer Gene Therapy (2010) 17, 655-663 (Year: 2010).
Gri et al: "X40 ligand-transduced tumor cell vaccine synergizes with GM-CSF and requires CD40-Apc signaling to boost the host T cell antitumor response", J Immunol. Jan. 1, 2003;170(1):99-106.
Guedan et al. GALVexpression enhances the therapeutic efficacy of an oncolytic adenovirus by inducing cell fusion and enhancing virus distribution, 19 Gene Therapy 1048-57 (2012).
Gómez-Treviño et al. Effects of adenovirus-mediated SV5 fusogenic glycoprotein expression on tumor cells, 5 J. Gene Med. (2003) 483-492.
Haswell et al Eur J Immunol 2001 31 3094-3100.
Nakamori et al. Potent Antitumor Activity After Systemic Delivery of a Doubly Fusogenic Oncolytic Herpes Simplex Virus Against Metastatic Prostate Cancer, 60 The Prostate 53-60 (2004).
Nakano et al., Journal of Japan Surgical Society, 2001, 102, Extra Issue, p. 82, No. SF4e-4.
Office Action issued in European Patent Application No. 1770385, dated May 21, 2019.
Oliveira et al. Poxvirus Host Range Genes and Virus-Host Spectrum: A Critical Review, 9(11) Viruses 2017 331 (Nov. 7, 2017).
Output from antibodies-online.com search for CTLA-4 Antibodies (performed Nov. 24, 2021), available at https://www.antibodies-online.eom/search.php#5qk9.
Output from Antibodypedia search for CTLA-4 Antibodies (performed Nov. 24, 2021), available at https://www.antibodYPedia.eom/gene/l 9961/CTLA4.
Output from Biocompare search for CTLA-4 Antibodies (performed Nov. 24, 2021), available at https://www.biocompare.com/Search-Antibodies/?search=CTLA-4&said=0.
Output from the National Institutes of Health (NIH) National Center for Biotechnology Information (NCBI) Taxonomy Browser searches for "herpesviridae", "poxviridae", "adenovirdae", "retroviridae", "rhabdoviridae", "paramyxoviridae", and "reoviridae" (performed Nov. 3, 2021), available at: https://www.ncbi.nlm.nih.gov/Taxonomy/Browser/wwwtax.cgi7mode =Root.
Patentee's response to EPO communication dtd Sep. 25, 2009, EP No. 17701910.6.
Pentcheva-Hoang et al. B7-1 and B7-2 Selectively Recruit CTLA-4 and CD28 to the Immunological Synapse, 21 Immunity 401-413 (Sep. 2004).
Petition for Post-Grant Review of U.S. Pat. No. 10,947,513, filed Dec. 15, 2021 with the TTAB, Petitioner—Transgene and Bioinvent International AB.
Piasecki et al., "Talilmogene laherparepvec increases the anti-tumor efficacy of the anti-PD-1 Abstract, Apr. 19, 2015 Immune checkpoint blockade," AACR Annual Meeting Presentation.
Reese, "Abstract IA24: New frontiers in oncolytic virus therapy," Cancer Immunology Research, 2016, 4 (11):1A24-1A24.
Reoviridae Information from Virus Pathogen Resource (ViPR) retrieved on Nov. 4, 2021, available at https://www.viprbrc.org/brc/aboutPathogen.spg?decorator=reo.
Ribas, Clinical Development of the Anti-CTLA-4 Antibody Tremelimumab, 37(5) Seminars in Oncology 450-454 (Oct. 2010).
Riedel et al. Components and Architecture of the Rhabdovirus Ribonucleoprotein Complex, 12(9) Viruses 2020 959 (Aug. 2020).
Robbins et al; "Viral Vectors for Gene Therapy"; Pharmacol, Ther.; vol. 80, No. 1; pp. 35-47; 1998.
Robinson et al, "Novel Immunocompetent Murine Tumor Model for Evaluation of Conditionally Replication-Competent (Oncolytic) Murine Adenoviral Vectors," Journal of Virology, 2009, 83(8):3450-3462.
Rojas et al. Defining Effective Combinations of Immune Checkpoint Blockade and Oncolytic Virotherapy, 21(24) Clin. Cancer Res. 5543-51 (Dec. 2015).
Saha et al. The Adenovirus Genome Contributes to the Structural Stability of the Virion, 6(9) Viruses 2014 3563-3583 (Sep. 24, 2014).
Salzberg, Open questions: How many genes do we have? 16 BMC Biology 94 (Aug. 20, 2018).
Schirrmann et al., "Transient Production of scFv-Fc Fusion Proteins in Mammalian Cells", Antibody Engineering, 2010, vol. 2; Chapter 30, p. 387-398, © Springer-Verlag Berlin Heidelberg.
Senzer et al., "Phase II Clinical Trial of a Granulocyte-Macrophage Colony-Stimulating Factor-Encoding, Second-Generation Oncolytic herpesvims in Patients with Unresectable Metastatic Melanoma" Journal of Clinical Oncology, 2009, 27(34):5763-5771.
Shan et al., "Characterization of scFv-Ig Constructs Generated from the Anti-CD20 mAb 1F5 Using Linker Peptides of Varying Lengths", Journal of Immunology, 1999, 162:6589-6595.
Sharp and Li, The codon adaptation index—a measure of directional synonymous codon usage bias, and its potential applications, 15(3) Nucleic Acids Research 1281-95 (1987).
Simpson et al., "Combination of a Fusogenic Glycoprotein, Prodrug activation, and Oncolytic Herpes Simplex Virus for Enhanced Local Tumor Control," Cancer Research, 2006, 66(9):4835-4842.
Singh et al. Oncolytic viruses & their specific targeting to tumour cells, 136 Indian J. Med. Res. 571-584 (Oct. 2012).
Sinkovics and Horvath, Natural and genetically engineered viral agents for oncolysis and gene therapy of human cancers, 56 Arch. Immunol. Ther. Exp. 3-59 (2008).
Smith et al. Studies on the Use of Viruses in the Treatment of Carcinoma of the Cervix, 9(6) Cancer 1211-18 (Nov.-Dec. 1956).
Sokolowski et al., "Oncolytic virotherapy using herpes simplex vims: how far have we come?" Oncolytic Virotherapy, 2015, 4:207-219.

(56) References Cited

OTHER PUBLICATIONS

Species list extracted from International Committee on Taxonomy of Viruses (ICTY) Master Species List (Jul. 20, 2021), available at: https://talk.ictvonline.org/taxonomy/vmr/.
Statement of Grounds of Opposition from the Opponent, Margaret Dixon Limited, dated Jun. 7, 2021, EP3400293 (EP Appl. No. 17701910.6).
Study Details for Clinical Trial NCT02272855 "A Study of Combination Treatment With HF10 and Ipilimumab in Patients With Unresectable or Metastatic Melanoma", last updated Sep. 26, 2018, available at: https://clinicaltrials.gov/ct2/show/NCT02272855.
Study Details for Clinical Trial NCT02620423 "Study of Pembrolizumab with REOLYSIN® and Chemotherapy in Patients With Advanced Pancreatic Adenocarcinoma", last updated Sep. 13, 2018, available at: https://clinicaltrials.gov/ct2/show/NCT02620423.
Sumimoto et al.: "GM-CSF and B7-1 (CD80) co-stimulatory signals co-operate in the induction of effective anti-tumor Immunity in syngeneic mice", Int J Cancer. Nov. 14, 1997;73(4):556-61.
Summary of Characteristics of Commercial Viral Vectors from ThermoFisher Scientific, retrieved Nov. 4, 2021, available at https://www.thermofisher.com/us/en/home/references/gibco-cell-culture-basics/transfection-basics/gene-delivery-technologies/viral-delivery/viral-vectors.html.
Tan et al. Combination therapy of oncolytic herpes simplex virus HF10 and bevacizumab against experimental model of human breast carcinoma xenograft, 136 Int. J. Cancer 1718-30 (2015).
Terada K. et al., "Development of a rapid method to generate multiple oncolytic HSV vectors Gene Therapy, vol. 13, No. 8, (Apr. 1, 2006), pp. 705-714 and their in vivo evaluation using syngeneic mouse tumor models".
Tesfay et al. PEGylation of Vesicular Stomatitis Virus Extends Virus Persistence in Blood Circulation of Passively Immunized Mice, 87(7) Journal of Virology 3752-59 (Apr. 2013).
Third Party Submission submitted in Related U.S. Appl. No. 16/068,816, dated Jul. 16, 2019.
Third Party Submission submitted in Related U.S. Appl. No. 16/068,823, dated Jul. 18, 2019.
Third Party Submission submitted in Related U.S. Appl. No. 16/068,826, dated Aug. 7, 2019.
Third Party Submission submitted in Related U.S. Appl. No. 16/068,830, dated Jul. 18, 2019.
Todo, Tomoki, Armed oncolytic herpes simplex viruses for brain tumor therapy, 208-213, Cell Adhesion* Migration 2:3, Jul./Aug./Sep. 2008.
Van den Wollenberg et al. Replicating reoviruses with a transgene replacing the codons for the head domain of the viral spike, 22 Gene Therapy 267-279 (2015).
Wennier et al. Bugs and Drugs: Oncolytic Virotherapy in Combination with Chemotherapy, 13(9) Curr. Pharm. Biotechnol. 1817-33 (Jul. 2012).
Wertz et al. Adding genes to the RNA genome of vesicular stomatitis virus: positional effects on stability of expression, 76(15) J. Virol. 7642-50 (Aug. 2002).
Willemsen and Zwart, On the stability of sequences inserted into viral genomes, 5(2) Virus Evolution vez045 (Jul. 2019).
Yan et al., "Developing Novel Oncolytic Adenoviruses through Bioselection," Journal of Virology, 2003, 77 (4):2640-2650.
Yang et al. Cascade regulation of vaccinia virus gene expression is modulated by multistage promoters, 447(1-2) Virology 213-220 (Dec. 2013).
EPO Opposition "Opponent's Response in opposition proceedings against Replimune's European Patent EP 3400291", provided by the European Patent Office on May 4, 2023.
Fonteneau et al., "Oncolytic immunotherapy: The new clinical outbreak", OncoImmunology, 2016, 5:1,e1066961.
Japanese Notice of Rejection mailed Feb. 28, 2023 during examination of related JP Patent Appl. No. 2019-537074.
Marcos et al., "Mapping of the RNA promoter of Newcastle disease virus", Virology, vol. 331, Issue 2, 2005, pp. 396-406.
Noton and Fearns, "Initiation and regulation of paramyxovirus transcription and replication", Virology, 2015, 479-480, 545-554.
Yen et al. Vaccinia virus infection & temporal analysis of virus gene expression: Part 2, 2009(26) J. Vis. Exp. 1169 (Apr. 2009).
Yi et al.Cancer Res 2007, 67 20 10027-10037.
Yo, Y-T et al.: "Coexpression of Flt3 ligand and GM-CSF genes modulates immune responses induced by HER2/neu DNA vaccine", Cancer Gene Ther. Nov. 2007; 14(11):904-17.
Alekseenko et al: "Therapeutic properties of a vector carrying the HSV thymidine kinase and GM-CSF genes and delivered as a complex with a cationic copolymer", Journal of Translational Medicine (2015) 13:78.

* cited by examiner

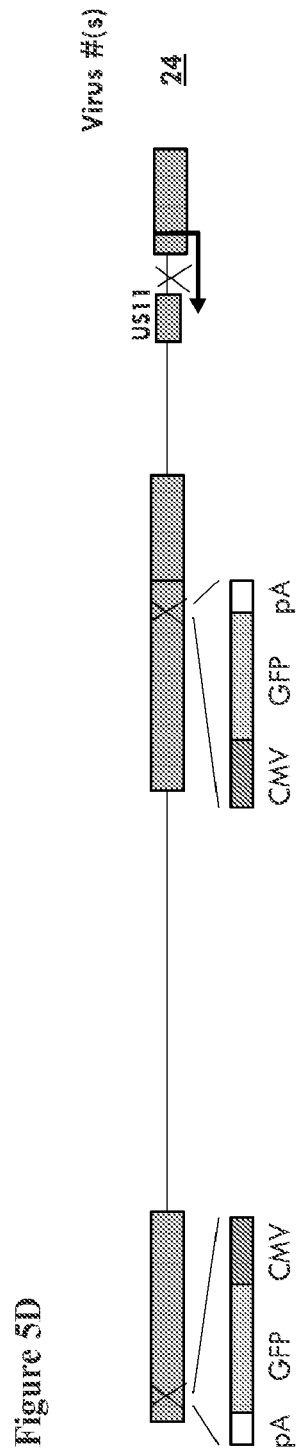

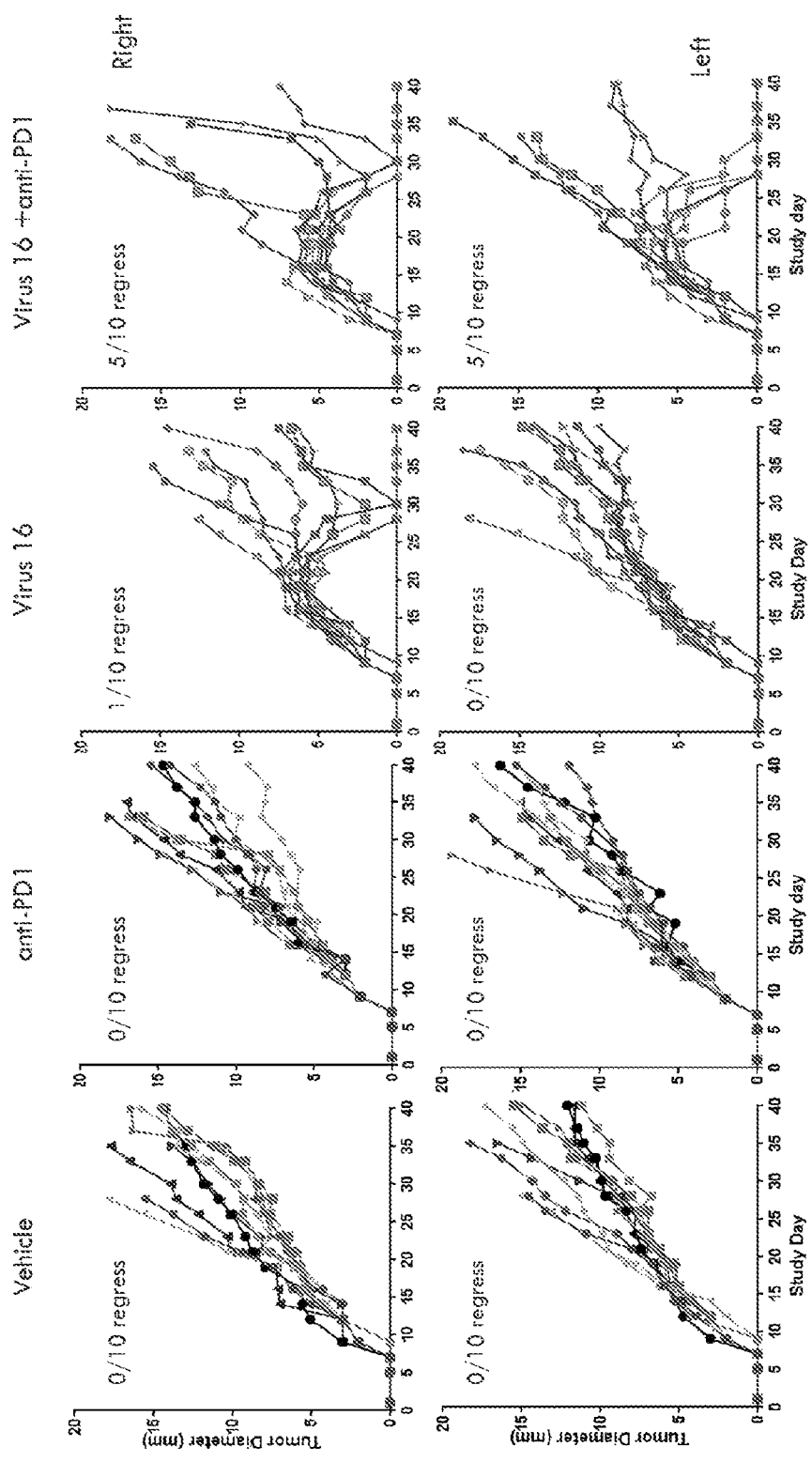

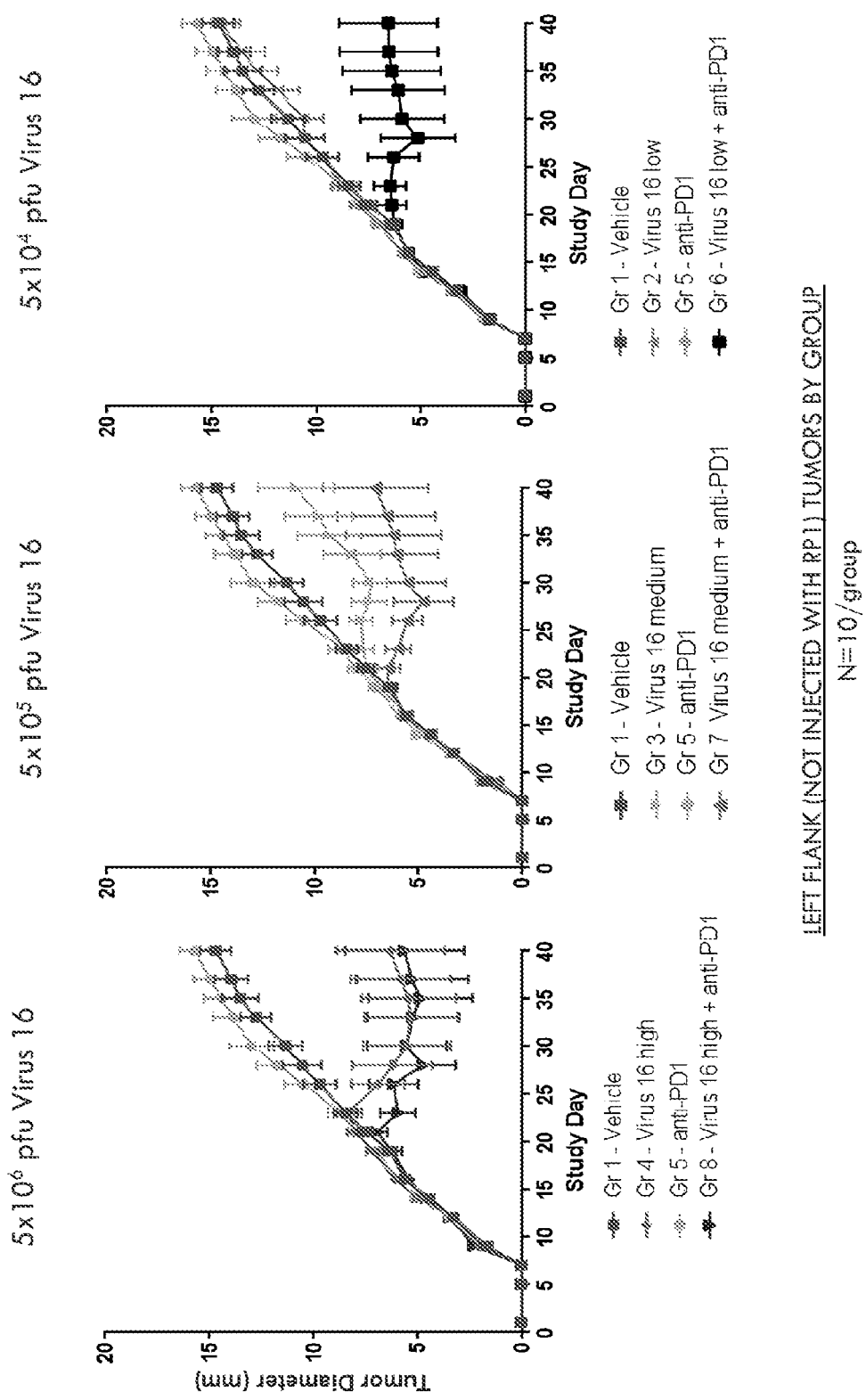

SEQUENCE LISTING

```
Sequence total quantity: 45
SEQ ID NO: 1           moltype = DNA  length = 426
FEATURE                Location/Qualifiers
source                 1..426
                       mol_type = genomic DNA
                       organism = Mus musculus
```

```
SEQUENCE: 1
atgtggctgc agaatttact tttcctgggc attgtggtct acagcctctc agcacccacc    60
cgctcaccca tcactgtcac ccggccttgg aagcatgtag aggccatcaa agaagccctg   120
aacctcctgg atgacatgcc tgtcacattg aatgaagagg tagaagtcgt ctctaacgag   180
ttctccttca agaagctaac atgtgtgcag acccgcctga agatattcga gcagggtcta   240
cggggcaatt tcaccaaaact caagggcgcc ttgaacatga cagccagcta ctaccagaca   300
tactgccccc caactccgga aacggactgt gaaacacaag ttaccaccta tgcggatttc   360
atagacagcc ttaaaacctt tctgactgat atcccctttg aatgcaaaaa accagtccaa   420
aaatga                                                               426

SEQ ID NO: 2              moltype = DNA   length = 426
FEATURE                   Location/Qualifiers
source                    1..426
                          mol_type = other DNA
                          organism = Mus musculus
SEQUENCE: 2
atgtggctcc agaacctcct cttcctcggt atcgtcgtgt attcactctc cgcacctact    60
cgctcaccta tcactgtcac cagacccctgg aagcacgtgg aggccatcaa ggaggctctg   120
aacctgctgg acgatatgcc agtgaccctg aacgaggagg tggaggtggt gagcaacgag   180
ttctccttta gaagctgac ctgcgtgcag acaaggctga agatcttcga gcagggcctg    240
agaggaaact ttaccaagct gaagggcgcc ctgaacatga ccgcttctta ctaccagaca   300
tactgccccc ctcccccga cacagactgt gagacacagg tgaccacata cgccgacttc   360
attgatagcc tgaaaacatt cctgaccgac attccatttg agtgtaagaa gccccgtccag  420
aagtaa                                                              426

SEQ ID NO: 3              moltype = DNA   length = 435
FEATURE                   Location/Qualifiers
source                    1..435
                          mol_type = genomic DNA
                          organism = Homo sapiens
SEQUENCE: 3
atgtggctgc agagcctgct gctcttgggc actgtggcct gcagcatctc tgcacccgcc    60
cgctcgccca gccccagcac gcagccctgg gagcatgtga atgccatcca ggaggcccgg   120
cgtctcctga acctgagtag agacactgct gctgagatga atgaaactgt agaagtcatc   180
tcagaaatgt ttgacctcca ggagccgacc tgcctacaga cccgcctgga gctgtacaag   240
cagggcctgc ggggcagcct caccaagctc aagggcccct tgaccatgat ggccagccac   300
tacaagcagc actgccctcc aaccccggaa cttcctgtg caaccagat atcaccttt    360
gaaagtttca agagaaacct gaaggacttt ctgcttgtca tcccctttga ctgctgggag   420
ccagtccagg agtga                                                    435

SEQ ID NO: 4              moltype = DNA   length = 435
FEATURE                   Location/Qualifiers
source                    1..435
                          mol_type = other DNA
                          organism = Homo sapiens
SEQUENCE: 4
atgtggctgc agtccctgct gctgctgggc accgtcgcct gttctatttc cgcacccgca    60
aggtcaccaa gtccatctac tcagccttgg gagcacgtga acgcaatcca ggaggcacgg   120
cggctgctga acctgagccg ggacaccgcc gccgagatga acgagacagt ggaagtgatc   180
agcgagatgt tcgatctgca ggagcccacc tgcctgcaga aggctgga gctgtacaag   240
cagggcctgc gcggctctct gaccaagctg aagggcccac tgacaatgat ggccagccac   300
tataagcagc actgcccccc tacccccgag acaagctgtg ccacccagat catcacattc   360
gagtcccttta aggagaacct gaaggatttt ctgctggtca ttccatttga ttgttgggag   420
cccgtccagg agtaa                                                    435

SEQ ID NO: 5              moltype = AA    length = 141
FEATURE                   Location/Qualifiers
source                    1..141
                          mol_type = protein
                          organism = Mus musculus
SEQUENCE: 5
MWLQNLLFLG IVVYSLSAPT RSPITVTRPW KHVEAIKEAL NLLDDMPVTL NEEVEVVSNE    60
FSFKKLTCVQ TRLKIFEQGL RGNFTKLKGA LNMTASYYQT YCPPTPETDC ETQVTTYADF   120
IDSLKTFLTD IPFECKKPVQ K                                             141

SEQ ID NO: 6              moltype = AA    length = 144
FEATURE                   Location/Qualifiers
source                    1..144
                          mol_type = protein
                          organism = Homo sapiens
SEQUENCE: 6
MWLQSLLLLG TVACSISAPA RSPSPSTQPW EHVNAIQEAR RLLNLSRDTA AEMNETVEVI    60
SEMFDLQEPT CLQTRLELYK QGLRGSLTKL KGPLTMMASH YKQHCPPTPE TSCATQIITF   120
ESFKENLKDF LLVIPFDCWE PVQE                                          144

SEQ ID NO: 7              moltype = DNA   length = 2010
FEATURE                   Location/Qualifiers
source                    1..2010
                          mol_type = genomic DNA
```

```
                        organism = Gibbon ape leukemia virus
SEQUENCE: 7
atggtattgc tgcctgggtc catgcttctc acctcaaacc tgcaccacct tcggcaccag    60
atgagtcctg ggagctggaa aagactgatc atcctcttaa gctgcgtatt cggcggcggc   120
gggacgagtc tgcaaaataa gaaccccac  cagcccatga ccctcacttg gcaggtactg   180
tcccaaactg gagacgttgt ctgggataca aaggcagtcc agcccccttg gacttggtgg   240
cccacactta aacctgatgt atgtgccttg gcggctagtc ttgagtcctg ggatatcccg   300
ggaaccgatg tctcgtcctc taaacgagtc agacctccgg actcagacta tactgccgct   360
tataagcaaa tcacctgggg agccataggg tgcagctacc ctcgggctag gactagaatg   420
gcaagctcta ccttctacgt atgtccccgg gatggccgga cccttcaga  agctagaagg   480
tgcgggggc  tagaatccct atactgtaaa gaatgggatt gtgagaccac ggggaccggt   540
tattggctat ctaaatcctc aaaagacctc ataactgtaa aatgggacca aaatagcgaa   600
tggactcaaa aatttcaaca gtgtcaccag accggctggt gtaaccccct aaaatagat   660
ttcacagaca aaggaaaatt atccaaggac tggataaagg gaaaacctg  gggattaaga   720
ttctatgtgt ctggacatcc aggcgtacga ttccaccattc gcttaaaaat caccaacatg   780
ccagctgtgg cagtaggtcc tgacctcgtc cttgtggaac aaggacctcc tagaacgtcc   840
ctcgctctcc cacctcctct tccccaagg  gaagcgccac cgccatctct ccccgactct   900
aactccacag ccctggcgac tagtgcacaa actcccacgg tgagaaaaac aattgttacc   960
ctaaacactc cgcctcccac cacaggcgac agacttttg  atcttgtgca gggggccttc  1020
ctaaccttaa atgctaccaa cccagggcc  actgagtctt gctggctttg tttggccatg  1080
ggcccccctt attatgaagc aatagcctca tcaggagagg tcgcctactc caccgacctt  1140
gaccggtgcc gctgggggac ccaaggaaag ctcaccctca ctggttctgtc aggacacggg  1200
ttgtgcatag aaaaggtgcc ctttacccat cagcatctct gcaatcagac cctatccatc  1260
aattcctccg gagaccatca gtatctgctc ccctccaacc atagctgtg  ggcttgcagc  1320
actgcctca  ccccttgcct ctccacctca gttttaatc  agactagaga tttctgtatc  1380
caggtccagc tgattcctcg catctattac atcctgcagg aagtttttgtt acaggcctat  1440
gacaattctc accccaggac taaaagagag gctgtctcac ttaccctagc tgtttttactg  1500
gggttgggaa tcacgcgggg aataggtact ggttcaactg ccttaattaa aggacctata  1560
gacctccagc aaggcctgac aagcctccag atcgccatag atgctgacct ccgggccctc  1620
caagactcag tcagcaagtt agaggactca ctgacttccc tgtccgaggt agtgctccaa  1680
aataggagag gccttgactt gctgtttcta aaagaaggtg gcctctgtgc ggccctaaag  1740
gaagagtgct gtttttacat agaccactca ggtgcagtac gggactccat gaaaaaactc  1800
aaagaaaaac tggataaaag acagttagag cgccagaaaa gccaaactg  gtatgaagga  1860
tggttcaata actcccccttg gttcactacc ctgctatcaa ccatcgctgg gcccctatta  1920
ctcctccttc tgttgctcat cctcgggcca tgcatcatca taagttagt  tcaattcatc  1980
aatgatagga taagtgcagt taaaatttaa                                    2010
SEQ ID NO: 8           moltype = DNA  length = 2013
FEATURE                Location/Qualifiers
source                 1..2013
                       mol_type = other DNA
                       organism = Gibbon ape leukemia virus
SEQUENCE: 8
accatggtcc tgctgcctgg gtctatgctg ctgacttcta acctgcacca cctgcgacac    60
cagatgtctc ccggctcatg gaaacggctg atcatcctgc tgagctgcgt gttcggagga   120
ggaggcacct ccctgcagaa caagaatcct caccagccaa tgaccctgac atggcaggtg   180
ctgtcccaga caggcgacgt ggtgtggat  accaaggcag tgcagccacc ttggacatgg   240
tggcccaccc tgaagcctga cgtgtgcgcc ctggccgcct ccctggagtc ttgggacatc   300
cccggcacag acgtgagcag cagcaagagg gtgagaccac ccgactctga ttatacagcc   360
gcctacaagc agatcacctg gggcgccatc ggctgtagct atcctcgggc cgcacaagg   420
atggccagct ccaccttta  cgtgtgccca cgcgacggaa gaccctgtc  tgaggcaagg   480
agatgtggcg gcctggagag cctgtattgc aaggagtggg attgtgagac cacaggcaca   540
ggctactggc tgtctaagtc tagcaaggac ctgatcaccg tgaagtggga tcagaacagc   600
gagtggcacag agagttcca  gcagtgccac cagaccggct ggtgtaatcc cctgaagatc   660
gactttacag ataagggcaa gctgtccaag gactggataa ccggcaagac atgggggctg   720
agattctacg tgtctggcca ccctggcgtg cagtttacaa tccggctgaa gatcaccaac   780
atgccagcag tggcagtggg accagacctg gtgctggtgg agcagggacc tccacgcacc   840
tccctggccc tgccccctcc actgcccct  agggaggccc cacccctag  cctgcccgat   900
tctaacagca cagccctggc cacctccgcc cagaccccta cagtcgcaa  gaccatcgtg   960
acactgaata cccccacccc taccacaggc gacaggctgt tcgatctggt gcagggcgcc  1020
tttctgacac tgaacgccac caatcctggc gcaaccgaga gctgctggct gtgcctggct  1080
atgggcccac cctactatga ggcaatcgcc tcctctggag aggtggcata ttccacagac  1140
ctggatagat gcagatgggg caccccaggc aagctgaccc tgacagaggt gtctggccac  1200
ggcctgtgca tcggcaaggt gccattcaca caccagcagc tgtgcaacca tgtgaggtt   1260
atcaatagct ccggcgacca ccagtacctg ctgccaagca accactcctg gtgggcatgc  1320
tccacaggac tgaccccatg tctgagcacc agcgtgttca accagaccag agactttgtg  1380
atccaggtgc agctgatccc tcggatctac tattacccag aggaggtgct gctgcaggcc  1440
tatgataatt cccacccaag aacaaagagg gaggccgtgt ctctctgctt ggccgtgctg  1500
ctgggactgg gaatcacagc aggaatcggc acaggcagca ccgccctgat caagggacca  1560
atcgacctgc agcagggact gacctccctg cagatcgcca tcgacgccga tctgagagcc  1620
ctgcaggaca gcgtgtccaa gctggaggat tctctgacct ctctgagcga ggtggtgctg  1680
cagaacagga ggggcctgga cctgctgttc ctgaaggagg aggactgtg  cgccgccctg  1740
aaggaggagt gctgttttta tatcgaccac tctggccgcg tgcgggatag catgaagaag  1800
ctgaaggaga agctggataa gcgccagctg gagaggcaga ttggtacgag  1860
ggctggttca acaattcccc ctggtttacc acactgctgt ctaccatcgc aggacctctg  1920
ttattactgc tgctgctgct gatcctgggc ccatgtatca tcaacaagct ggtgcagttt  1980
atcaacgacc gaatctccgc agtgaaaatc taa                                2013
SEQ ID NO: 9           moltype = AA  length = 669
```

```
FEATURE                 Location/Qualifiers
source                  1..669
                        mol_type = protein
                        organism = Gibbon ape leukemia virus
SEQUENCE: 9
MVLLPGSMLL  TSNLHHLRHQ  MSPGSWKRLI  ILLSCVFGGG  GTSLQNKNPH  QPMTLTWQVL   60
SQTGDVVWDT  KAVQPPWTWW  PTLKPDVCAL  AASLESWDIP  GTDVSSSKRV  RPPDSDYTAA  120
YKQITWGAIG  CSYPRARTRM  ASSTFYVCPR  DGRTLSEARR  CGGLESLYCK  EWDCETTGTG  180
YWLSKSSKDL  ITVKWDQNSE  WTQKFQQCHQ  TGWCNPLKID  FTDKGKLSKD  WITGKTWGLR  240
FYVSGHPGVQ  FTIRLKITNM  PAVAVGPDLV  LVEQGPPRTS  LALPPPLPPR  EAPPPSLPDS  300
NSTALATSAQ  TPTVRKTIVT  LNTPPPTTGD  RLFDLVQGAF  LTLNATNPGA  TESCWLCLAM  360
GPPYYEAIAS  SGEVAYSTDL  DRCRWGTQGK  LTLTEVSGHG  LCIGKVPFTH  QHLCNQTLSI  420
NSSGDHQYLL  PSNHSWWACS  TGLTPCLSTS  VFNQTRDFCI  QVQLIPRIYY  YPEEVLLQAY  480
DNSHPRTKRE  AVSLTLAVLL  GLGITAGIGT  GSTALIKGPI  DLQQGLTSLQ  IAIDADLRAL  540
QDSVSKLEDS  LTSLSEVVLQ  NRRGLDLLFL  KEGGLCAALK  EECCFYIDHS  GAVRDSMKKL  600
KEKLDKRQLE  RQKSQNWYEG  WFNNSPWFTT  LLSTIAGPLL  LLLLLLILGP  CIINKLVQFI  660
NDRISAVKI                                                                669

SEQ ID NO: 10           moltype = DNA  length = 759
FEATURE                 Location/Qualifiers
source                  1..759
                        mol_type = other DNA
                        organism = Homo sapiens
SEQUENCE: 10
atgatcgaga  cctacaatca  gacaagccca  cggtccgccg  caaccggact  gcctatcagc   60
atgaagatct  tcatgtacct  gctgaccgtg  tttctgatca  cacagatgat  cggctccgcc  120
ctgttcgccg  tgtatctgca  caggagactg  gacaagatcg  aggatgagcg  caatctgcac  180
gaggacttcg  tgtttatgaa  gaccatccag  cggtgcaaca  caggcgagag  gagcctgtct  240
ctgctgaatt  gtgaggagat  caagtcccag  ttcgagggct  tgtgtaagga  tatcatgctg  300
aacaaggagg  agacaaagaa  ggacgaggat  ccacagatcg  ccgcacacgt  ggtgtccgag  360
gcaaactcta  atgccgccag  cgtgctgcag  tgggccaaga  agggctacta  taccatgaag  420
tctaacctgg  tgacactgga  aatggcaagc  agctgaccg   tgaagaggca  gggcctgtac  480
tatatctatg  cccaggtgac  attctgctct  aacagagagg  caagctccca  ggcacccttc  540
atcgtgggac  tgtggctgaa  gccctctagc  ggcagcgaga  ggatcctgct  gaaggccgcc  600
aataccccact  cctctagcca  gctgtgcgag  cagcagtcca  tccacctggg  aggcgtgttc  660
gagctgcagc  ctggagccag  cgtgttcgtg  aacgtgacag  acccatctca  ggtgagccac  720
ggcaccggct  tcacaagctt  tggcctgctg  aagctgtga                            759

SEQ ID NO: 11           moltype = AA  length = 252
FEATURE                 Location/Qualifiers
source                  1..252
                        mol_type = protein
                        organism = Homo sapiens
SEQUENCE: 11
MIETYNQTSP  RSAATGLPIS  MKIFMYLLTV  FLITQMIGSA  LFAVYLHRRL  DKIEDERNLH   60
EDFVFMKTIQ  RCNTGERSLS  LLNCEEIKSQ  FEGFVKDIML  NKEETKKDED  PQIAAHVVSE  120
ANSNAASVLQ  WAKKGYYTMK  SNLVTLENGK  QLTVKRQGLY  YIYAQVTFCS  NREASSQAPF  180
IVGLWLKPSS  GSERILLKAA  NTHSSSQLCE  QQSIHLGGVF  ELQPGASVFV  NVTDPSQVSH  240
GTGFTSFGLL  KL                                                          252

SEQ ID NO: 12           moltype = DNA  length = 1416
FEATURE                 Location/Qualifiers
source                  1..1416
                        mol_type = other DNA
                        organism = Homo sapiens
SEQUENCE: 12
atgctgccct  ttctgagcat  gctggtgctg  ctggtgcagc  tctgggaaa   cctgggagcc   60
gagatgaaga  gcctgtccca  gagatctgtg  cctaacacct  gcacactggt  catgtgcagc  120
cccaccgaga  tggactgcc   tggaagggac  ggaagggatg  gaagggaggg  ccctcggggc  180
gagaagggcg  acccaggact  gcctggacca  atggactgca  gcggactgca  gggaccaaca  240
ggacctgtgg  gaccaaaggg  agagaacgga  tccgccggag  agccaggccc  taagggcgag  300
aggggcctgt  ctggcccccc  tggcctgcca  ggcatcccag  gccccgccgg  caaggagggc  360
ccatccggca  agcagggcaa  tatcggcccc  cagggcaagc  tgggccccaa  gggcgaggca  420
ggaccaaagg  gagaagtggg  agcacctggc  atgcagggat  ccaccgagca  aaagggatct  480
acaggaccaa  agggcgagcg  cggcgcccca  ggcgtgcagg  cgcccccgg   caatgcagga  540
gcagcaggac  cagcaggacc  tgcaggccca  cagggcgccc  ctggctctag  ggccccaccc  600
ggcctgaagg  gcgacagggg  agtgcctggc  gataggggca  tcaagggaga  gagcggactg  660
ccagattccg  ccgccctgag  gcagcagatg  gaggccctga  agggcaagct  gcagaggctg  720
gaggtggcct  tctcccacta  ccagaaggcc  gcctgtttc   cagacggcca  caggagactg  780
gacaagatcg  aggatgagcg  caacctgcac  gaggatttcg  tgtttatgaa  gaccatccag  840
agatgcaaca  caggcgagcg  gtctctgagc  ctgctgaatt  gtgaggagat  caagtctcag  900
ttcgagggct  tgtgtaagga  catcatgctg  aacaaggagg  agaccaagaa  ggagaatagc  960
ttcgagatgc  agaagggcga  tcagaatccc  cagatcgcag  cacacgtgat  cagcgaggca 1020
agctcccaaga  ccacatccgt  gctgcagtgg  gccaagaagg  gctactatac  gatgtccaac 1080
aatctggtga  cactggagaa  cggcaagcag  ctgaccgtga  agagacaggg  cctgtactat 1140
atctatgccc  aggtgacatt  ctgctctaat  cgggaggcct  ctagccaggc  ccctttatc  1200
gcctctctgt  gcctgaagag  cccaggcaga  ttcgagcgga  tcctgctgag  ggccgccaac 1260
acccactcct  ctgccaagcc  atgcggacag  cagagcatcc  acctgggagg  cgtgttcgag 1320
ctgcagccag  gagcctccgt  gtttgtgaat  gtgacagacc  catcccaggt  gtctcacgga 1380
```

```
accggcttca catcctttgg cctgctgaag ctgtga                              1416
```

SEQ ID NO: 13           moltype = AA    length = 471
FEATURE                 Location/Qualifiers
source                  1..471
                        mol_type = protein
                        organism = Homo sapiens
SEQUENCE: 13

```
MLPFLSMLVL LVQPLGNLGA EMKSLSQRSV PNTCTLVMCS PTENGLPGRD GRDGREGPRG   60
EKGDPGLPGP MGLSGLQGPT GPVGPKGENG SAGEPGPKGE RGLSGPPGLP GIPGPAGKEG  120
PSGKQGNIGP QGKPGPKGEA GPKGEVGAPG MQGSTGAKGS TGPKGERGAP GVQGAPGNAG  180
AAGPAGPAGP QGAPGSRGPP GLKGDRGVPG DRGIKGESGL PDSAALRQQM EALKGKLQRL  240
EVAFSHYQKA ALFPDGHRRL DKIEDERNLH EDFVFMKTIQ RCNTGERSLS LLNCEEIKSQ  300
FEGFVKDIML NKEETKKENS FEMQKGDQNP QIAAHVISEA SSKTTSVLQW AEKGYYTMSN  360
NLVTLENGKQ LTVKRQGLYY IYAQVTFCSN REASSQAPFI ASLCLKSPGR FERILLRAAN  420
THSSAKPCGQ QSIHLGGVFE LQPGASVFVN VTDPSQVSHG TGFTSFGLLK L           471
```

SEQ ID NO: 14           moltype = DNA    length = 1412
FEATURE                 Location/Qualifiers
source                  1..1412
                        mol_type = other DNA
                        organism = Mus musculus
SEQUENCE: 14

```
atgctgccct tcctgagcat gctggtgctg ctggtgcagc ctctgggcaa tctgggcgcc   60
gagatgaagt ccctgtctca gaggagcgtg ccaaacacct gcacactggt catgtgctct  120
ccaaccgaga atggactgcc aggaagggac ggaagagatg gaagggaggg accaaggga   180
gagaagggcg accctggact gcctggacca atgggactgt ccggactgca gggaccaaca  240
ggccctgtgg gaccaaaggg agagaatgga agcgccggag agccaggacc taagggagag  300
aggggcctgt ccggcccccc tggcctgcct ggcatcccag gccccgccgg caaggagggc  360
ccttctggca gcagggcaa catcggacca cagggcaagc ctgggaaggg agagggaca   420
ggaccaaagg gagaagtggg agcaccggc atgcaggga gcaccggagc aaagggatcc  480
accggcccta agggagagag aggagcacct ggagtgcagg gcgcccagg caatgcagga  540
gcagcaggac cagcaggacc tgcaggccca cagggcgccc caggcagccg ggcccacccc  600
ggcctgaagg gcgacagggg agtgccaggc gataggggga tcaagggaga gtccggactg  660
ccagactctg ccgcctgag gcagcagatg gaggccctga agggcaagct gcagaggctg  720
gaggtggcct tctcccacta ccagaaggcc gccctgtttc cagacggaca caggagactg  780
gataaggtgg aggaggaggt gaacctgcac gaggatttcg tgttcatcaa gaagctgaag  840
aggtgcaaca agggcgaggg cagcctgtcc ctgctgaatt gtgaggagat gcggcgccag  900
ttcgaggacc tggtgaagga tatcacctg aacaaggagg agaagaagga gaattctttt  960
gagatgcaga ggggcgacga ggatcctcag atcgcagcac acgtggtgtc cgaggcaaac 1020
tctaatgccg ccagcgtgct gcagtgggcc aagaagggct actataccat gaagtctaac 1080
ctggtcatgc tggagaatgg caagcagctg acagtgaaga gagggcct gtactacgtg 1140
tacacccagg tgacattctg cagcaacaga gagcccagcc cccagcggcc ttttatcgtg 1200
ggcctgtggc tgaagccctc tatcggaagc gagaggatcc tgctgaaggc agccaatacc 1260
cactctagct cccagcgtgtg cgagcagcag tccgtgcacc tgggaggcgt gttcgagctg 1320
caggcaggag caagcgtgtt cgtgaacgga cagaggccag ccaggtcatc cacagagtgg 1380
gcttctctag ctttggcctg ctgaagctgt ga                               1412
```

SEQ ID NO: 15           moltype = AA    length = 470
FEATURE                 Location/Qualifiers
source                  1..470
                        mol_type = protein
                        organism = Mus musculus
SEQUENCE: 15

```
MLPFLSMLVL LVQPLGNLGA EMKSLSQRSV PNTCTLVMCS PTENGLPGRD GRDGREGPRG   60
EKGDPGLPGP MGLSGLQGPT GPVGPKGENG SAGEPGPKGE RGLSGPPGLP GIPGPAGKEG  120
PSGKQGNIGP QGKPGPKGEA GPKGEVGAPG MQGSTGAKGS TGPKGERGAP GVQGAPGNAG  180
AAGPAGPAGP QGAPGSRGPP GLKGDRGVPG DRGIKGESGL PDSAALRQQM EALKGKLQRL  240
EVAFSHYQKA ALFPDGHRRL DKVEEEVNLH EDFVFIKKLK RCNKGEGSLS LLNCEEMRRQ  300
FEDLVKDITL NKEEKKENSF EMQRGDEDPQ IAAHVVSEAN SNAASVLQWA KKGYYTMKSN  360
LVMLENGKQL TVKREGLYYV YTQVTFCSNR EPSSQRPFIV GLWLKPSIGS ERILLKAANT  420
HSSSQLCEQQ SVHLGGVFEL QAGASVFVNV TEASQVIHRV GFSSFGLLKL            470
```

SEQ ID NO: 16           moltype = DNA    length = 786
FEATURE                 Location/Qualifiers
source                  1..786
                        mol_type = other DNA
                        organism = Homo sapiens
SEQUENCE: 16

```
atgatcgaaa catacaacca aacttctccc cgatctgcgg ccactggact gcccatcagc   60
atgaaaattt ttatgtattt acttactgtt tttcttatca cccagatgat tgggtcagca  120
cttttttgctg tgtatcttca tagaaggttg gacaagatag aagatgaaag gaatcttcat  180
gaagattttg tattcatgaa aacgatacag agatgcaaca caggagaaag atccttatcc  240
ttactgaact gtgaggcgat taaaagccag tttgaaggct ttgtgaagga tataatgtta  300
aacaaagagg agacgaagaa agaaaacagc tttgaaatgc aaaaaggtga tcagaatcct  360
caaattgcgg cacatgtcat aagtgaggcc agcagtaaaa caacatctgt gttacagtgg  420
gctgaaaaag gatactacac catgagcaac aacttggtaa ccctgaaaaa tgggaaacag  480
ctgaccgtta aaagacaagg actctattat atctatgccc aagtcacctt ctgttccaat  540
cgggaagctt cgagtcaagc tccattata gccagcctc gcctaaagtc ccccggtaga  600
```

```
ttcgagagaa tcttactcag agctgcaaat acccacagtt ccgccaaacc ttgcgggcaa    660
caatccattc acttgggagg agtatttgaa ttgcaaccag gtgcttcggt gtttgtcaat    720
gtgactgatc caagccaagt gagccatggc actggcttca cgtcctttgg cttactcaaa    780
ctctga                                                               786

SEQ ID NO: 17           moltype = AA   length = 261
FEATURE                 Location/Qualifiers
source                  1..261
                        mol_type = protein
                        organism = Homo sapiens
SEQUENCE: 17
MIETYNQTSP RSAATGLPIS MKIFMYLLTV FLITQMIGSA LFAVYLHRRL DKIEDERNLH     60
EDFVFMKTIQ RCNTGERSLS LLNCEEIKSQ FEGFVKDIML NKEETKKENS FEMQKGDQNP    120
QIAAHVISEA SSKTTSVLQW AEKGYYTMSN NLVTLENGKQ LTVKRQGLYY IYAQVTFCSN    180
REASSQAPFI ASLCLKSPGR FERILLRAAN THSSAKPCGQ QSIHLGGVFE LQPGASVFVN    240
VTDPSQVSHG TGFTSFGLLK L                                              261

SEQ ID NO: 18           moltype = DNA   length = 783
FEATURE                 Location/Qualifiers
source                  1..783
                        mol_type = other DNA
                        organism = Mus musculus
SEQUENCE: 18
atgatagaaa catacagcca accttccccc agatccgtgg caactggact tccagcgagc     60
atgaagattt ttatgtattt acttactgtt ttccttatca cccaaatgat tggatctgtg    120
cttttgctg tgtatcttca tagaagattg gataaggtcg aagaggaagt aaaccttcat    180
gaagatttg tattcataaa aaagctaaag agatgcaaca aaggagaagg atctttatcc    240
ttgctgaact gtgaggagat gagaaggcaa tttgaagacc ttgtcaagga tataacgtta    300
aacaaagaag agaaaaaaga aacagctttt gaaatgcaaa gaggtgatga ggatcctcaa    360
attgcagcac acgttgtaag cgaagccaac agtaatgcag catccgttct acagtgggcc    420
aagaaaggat attataccat gaaaagcaac ttggtaatgc ttgaaaatgg gaaacagctg    480
acggttaaaa gagaaggact ctattatgtc tacactcaag tcaccttctg ctctaatcgg    540
gagccttcga gtcaacgccc attcatcgtc ggcctctggc tgaagcccag cagtggatct    600
gagagaatct tactcaaggc ggcaaatacc cacagttcct cccagctttg cgagcagcag    660
tctgttcact gggcggagt gtttgaatta caagctggtg cttctgtgtt tgtcaacgtg    720
actgaagcaa gccaagtgat ccacagagtt ggcttctcat cttttggctt actcaaactc    780
tga                                                                  783

SEQ ID NO: 19           moltype = AA   length = 260
FEATURE                 Location/Qualifiers
source                  1..260
                        mol_type = protein
                        organism = Mus musculus
SEQUENCE: 19
MIETYSQPSP RSVATGLPAS MKIFMYLLTV FLITQMIGSV LFAVYLHRRL DKVEEEVNLH     60
EDFVFIKKLK RCNKGEGSLS LLNCEEMRRQ FEDLVKDITL NKEEKKENSF EMQRGDEDPQ    120
IAAHVVSEAN SNAASVLQWA KKGYYTMKSN LVMLENGKQL TVKREGLYYV YTQVTFCSNR    180
EPSSQRPFIV GLWLKPSSGS ERILLKAANT HSSSQLCEQQ SVHLGGVFEL QAGASVFVNV    240
TEASQVIHRV GFSSFGLLKL                                                260

SEQ ID NO: 20           moltype = DNA   length = 930
FEATURE                 Location/Qualifiers
source                  1..930
                        mol_type = other DNA
                        organism = Mus musculus
SEQUENCE: 20
atggatcagc acacactgga cgtggaggat accgctgacg ctaggcaccc agctggcacc     60
tcctgccctt ctgatgccgc tctgctgcgc gacacaggac tgctggccga tgccgctctg    120
ctgtctgaca cagtgcggcc aaccaacgcc gctctgccaa gcatgctgc ttaccctgct    180
gtgaacgtga gggacagaga ggctgcttgg ccacctgccc tgaacttctg cagccgccac    240
cctaagctgt acggcctggt ggccctggtg ctgctgctgc tgatcgctgc ttgcgtgcca    300
atctttaccc ggacagagcc acgcccgct ctgacaatca ccacatcccc caacctgggc    360
accagggaga caacgccga tcaggtgaca ccagtgtctc acatcggctg ccccaacacc    420
acacagcagg gaagcccagt gttcgccaag ctgctggctg agaaccaggc cagctggaca    480
aacaccacac tgaactggca cagccaggac ggagctggaa gctcctacct gtcccagggc    540
ctgagatacg aggaggataa gaaggagctg gtggtggact ccctggact gtactacgtg    600
ttcctggagc tgaagctgtc tccaaccctt acaaacaccg gccacaaggt gcagggatgg    660
gtgtctctgg tgctgcaggc taagcccag gtggacgatt tcgataacct ggccctgacc    720
gtgggagctg ttccttgtag catggagaac aagtcggtct caaggtcttg ggcagctgtg    780
ctgctgctga aggctggcca caggctgtcc gtgggactga gagcctacct ggcacgcgcc    840
caggatgctt acagagactg ggagctgagc taccctaaca ccacatcctt cggactgttt    900
ctggtgaagc ctgacaaccc atgggagtga                                     930

SEQ ID NO: 21           moltype = DNA   length = 765
FEATURE                 Location/Qualifiers
source                  1..765
                        mol_type = other DNA
                        organism = Homo sapiens
SEQUENCE: 21
```

-continued

```
atggagtacg cctctgacgc cagcctggat ccagaggccc cttggccacc tgcaccaagg    60
gcccgcgcct gccgcgtgct gccctgggcc ctggtggccg gcctgttatt actgctgctg   120
ctggccgccg cctgcgccgt gttcctggca tgtccttggg ccgtgagcgg agccagagcc   180
tccccaggct ctgccgccag ccctcggctg agagagggac cagagctgtc cccagacgat   240
ccagcaggcc tgctggacct gaggcaggga atgtttgccc agctggtggc ccagaacgtg   300
ctgctgatcg acggcccct gtcctggtac tctgatcctg gcctggccgg cgtgtctctg   360
accggcggcc tgagctataa ggaggataca aaggagctgg tggtggccaa ggccggcgtg   420
tactacgtgt tcttccagct ggagctgagg agagtggtgg caggagaggg ctctggaagc   480
gtgtccctgg ccctgcacct gcagccctg cggagcgccg caggagccgc cgccctggcc   540
ctgaccgtgg acctgccacc agccagctcc gaggcaagga attccgcctt cggctttcag   600
ggcagactgc tgcacctgtc tgccggacag aggctgggag tgcacctgca caccgaggcc   660
agggcccgcc acgcatggca gctgacccag ggagcaacag tgctgggcct gttccgcgtg   720
acacctgaga tcccagcagg cctgcctagc ccacggtccg agtga                   765

SEQ ID NO: 22          moltype = DNA    length = 1389
FEATURE                Location/Qualifiers
source                 1..1389
                       mol_type = other DNA
                       organism = Mus musculus
SEQUENCE: 22
atgctgcctt tcctgtccat gctggtgctg ctggtgcagc cactgggcaa cctgggagcc    60
gagatgaagt ctctgagcca gcgcagcgtg cctaacactg cacactggt catgtgctcc   120
cctacagaga acggcctgcc aggaaaggac ggaagagatg aaggagggg accaagggga   180
gagaagggcg accccggact gcctggacca atgggactga gcggcctgca gggaccaacc   240
ggccccgtgg acctaaggg agagaacgga tccgctggag agccaggacc taaggagag   300
agaggactgt ctggaccacc tggactgcca ggaatcccga gccagctgca caggagggga   360
ccatccggca agcagggaaa catcggacca cagggaaagc ctggaccaaa gggagaggct   420
ggacctaagg gagaagtggg cgccccagga atgcagggct ctacaggagc taagggcagc   480
accggaccaa agggagagag gggagccccc ggagtgcagg gagcccctgg caacgctgga   540
gccgctggcc cagccggacc cgctggccct cagggagccc ccggctctag gggaccacca   600
ggcctgaagg gagacagagg cgtgcccgga gatcggggca tcaagggaga gagcggcctg   660
cctgactccg ccgctctgag acagcagatg gaggctctga agccaagct gcagcggctg   720
gaggtggcct ctcccactaa ccagaaggcc gctctgtttc tgacggaag acagagccc   780
aggcctgctc tgaccatcac cacatctcca aacctgggca caagagagaa caacgccgat   840
caggtgaccc ccgtgtctca catcggatgc cctaacacca cacagcaggg cagccccgtg   900
tttgccaagc tgctggctaa gaaccaggcc agcctgtgca acaccacact gaactggcac   960
tcccaggatg gcgccggaag ctcctacctg tctcagggcc tgcggtacga ggaggacaag  1020
aaggagctgg tggtggatag cccaggcctg tactacgtgt tcctggagct gaagctgtcc  1080
cccaccttta caaacaccgg acacaaggtg cagggatggg tgagcctggt gctgcaggct  1140
aagcccaggg tggacgattt cgacaacctg gccctgaccg tggagctgtt tccttgctct  1200
atggagaaca agctggtgga tagatcctgg agccagctgc tgctgctgaa ggctggacac  1260
cgcctgagcg tgggcctgag gcttacctg cacgagctc aggacgctta cagggattgg  1320
gagctgtcct acccaccac cacatctttc ggcctgtttc tggtgaagcc agacaacccc  1380
tgggagtga                                                          1389

SEQ ID NO: 23          moltype = DNA    length = 1389
FEATURE                Location/Qualifiers
source                 1..1389
                       mol_type = other DNA
                       organism = Homo sapiens
SEQUENCE: 23
atgctgctgt tcctgctgtc cgccctggtg ctgctgaccc agcctctggg ctacctggag    60
gccgagatga agacctattc tcaccggaca atgccaagcg cctgcacact ggtcatgtgc   120
agcagcgtga gtctggcct gccaggaagg acgcgaaggg atggaaggga gggacctaga   180
ggcgagaagg gcgaccctgg cctgccagga gcagcaggaa caggagaat gcccggccaa   240
gccggccccg tgggacctaa gggcgacaac ggaagcgtgg gagagccagg accaaagggc   300
gataccggcc cttccggacc acctggacca ccaggcgtgc ctggcccagc cggcaggag   360
ggccctctgg gcaagcaggg caatatcggc ccacagggca gcccggccc taagggcgag   420
gccggccca agggcgaagt gggcgcccct ggcatgcagg gaagcgccgg agccgcggc   480
ctggccggac ctaagggcga gagggcgtg ctggagaga gggcgtgcc aggaaacaca   540
ggcgcagcag gatctgccgg agcaatggga cccaggca gcctggcgc caggggccct   600
ccaggcctga gggcgacaa ggcatccca ggcgataagg gagcaagggg agagagcggc   660
ctgccagatg tggcctccct cgccagcag gtggaggccc tgcagggcca ggtgcagcac   720
ctgcagggcc ccttctctca gtacaagaag gtggagctgt ttccaaacgg cgctgcccc   780
tgggccgtga gcgagcccg gcctccccca ggctctgccg ccagcctag ctgcgcgag   840
ggaccagagc tgagccaga cgatccagca ggcctgctgg acctgagaca gggaatgttc   900
gcccagctgg tggcccagaa tgtgctgctg atcgacggcc cactgtcctg gtactctgat   960
ccaggcctgg ccggcgtgtc cctgaccggc ggcctgtctt ataaggagga tacaaaggag  1020
ctggtggtgg ccaaggccgg cgtgtactac gtgttcttcc agctggagct gaggagagtg  1080
gtggcaggag agggatccgg atctgtgagc ctgccctgc acctgcagcc cctgcgtcc  1140
gccgcaggag ccgccgccct ggccctgacc gtggacctgc cacctgcctc tagcgaggca  1200
cgcaattccg ccttcggctt tcagggccgg ctgctgcacc tgtctgccgg acagagactg  1260
ggagtgcacc tgcacaccga ggcccgggcc agacacgcct ggcagctgac ccaggagca  1320
acagtgtggg gcctgtttag ggtgacacct gagatccag ccggcctgcc aagcccccgc  1380
tccgagtga                                                          1389

SEQ ID NO: 24          moltype = DNA    length = 522
FEATURE                Location/Qualifiers
source                 1..522
```

```
                        mol_type = other DNA
                        organism = Mus musculus
SEQUENCE: 24
atggaggaga tgcctctgag ggagagctcc ccacagaggg ccgagagatg caagaagagc    60
tggctgctgt gcatcgtggc tctgctgctg atgctgctgt gctctctggg caccctgatc   120
tacacaagcc tgaagccaac cgccatcgag tcctgtatgg tgaagttcga gctgtctagc   180
tccaagtggc acatgacatc ccccaagcct cactgcgtga acaccacatc tgacggaaag   240
ctgaagatcc tgcagagcgg cacctacctg atctacggac aggtcatccc cgtggacaag   300
aagtacatca aggataacgc ccctttcgtg gtgcagatct acaagaagaa cgacgtgctg   360
cagacactga tgaacgattt tcagatcctg cccatcggcg gagtgtacga gctgcacgct   420
ggcgacaaca tctacctgaa gttcaactcc aaggatcaca tccagaagac caacacatac   480
tggggaatca tcctgatgcc agatctgccc tttatctctt ga                      522

SEQ ID NO: 25           moltype = DNA  length = 600
FEATURE                 Location/Qualifiers
source                  1..600
                        mol_type = other DNA
                        organism = Homo sapiens
SEQUENCE: 25
atgaccctgc acccaagccc catcacatgc gagttcctgt tttctaccgc cctgatcagc    60
ccaaagatgt gcctgagcca cctggagaat atgcccctgt cccactctcg gacacaggga   120
gcccagagaa gctcctggaa gctgtggctg ttctgctcta tcgtgatgct gctgttcctg   180
tgcagctttt cctggctgat cttcatcttt ctgcagctgg agacagccaa ggagccttgc   240
atggccaagt ttggccctct gccatccaag tggcagatgg cctctagcga gcccccttgc   300
gtgaacaagg tgagcgactg gaagctggag atcctgcaga acggcctgta cctgatctat   360
ggccaggtgg cccccaacgc caattacaac gacgtgggcc ctttcgaggt ggcctgtat    420
aagaacaagg atatgatcca gaccctgaca aataagtcta agatccagaa cgtgggcggc   480
acatacgagc tgcacgtggg cgacaccatc gacctgatct tcaacagcga gcaccaggtg   540
ctgaagaaca atacatattg gggcatcatc ctgctggcca cccccagtt tatctcctga   600

SEQ ID NO: 26           moltype = DNA  length = 1164
FEATURE                 Location/Qualifiers
source                  1..1164
                        mol_type = other DNA
                        organism = Mus musculus
SEQUENCE: 26
atgctgcctt tcctgtctat gctggtgctg ctggtgcagc cactgggcaa cctgggagcc    60
gagatgaaga gcctgtccca gagatccgtg cccaacacct gcacactggt catgtgctct   120
cctaccgaga acggcctgcc aggaagggac ggaagagatg gaaggaggg acctcgggga   180
gagaagggcg acccaggact gcctggacca atgggactga gcggcctgca gggaccaaca   240
ggccccgtgg gacctaaggg agagaacgga agcgccggag agccaggacc taagggagag   300
agggggactgt ccgaccacc tggactgcct ggaatcccag accagctgg caaggaggga   360
ccatcggaca gcagggaaa catcggacca cagggaagcc ctggaccaaa gggagagggct   420
ggaccaaagg gagaagtggg cgctcctgga atgcagggct ccaccggagc caagggctct   480
acaggaccaa aggagagag gggagctccc ggagtgcagg gagcccctgg caacgctgga   540
gccgctggcc cagccggacc cgctggccct cagggagccc caggcagcag gggaccaccc   600
ggcctgcaggg gcgacagggg cgtgccagga gatagggcca tcaagggaga gtctgccctg   660
ccagacagcg ccgctctgag acagcagatg gaggccctga agcaagct gcagcggctg   720
gaggtggctt ctcccacta ccagaaggcc gctctgtttc cagatggcag cctgaagccc   780
accgccatcg agtcctgcat ggtgaagttt gagctgagct cctctaagtg gcacatgaca   840
tctcccaagc ctcactgcgt gaacaccaca tctgacggca gctgaagct cctgcagagc   900
ggcacctacc tgatctacgg ccaggtcatc cccgtggaca agaagtacat caaggataac   960
gcccctttcg tggtgcagat ctacaagaag aacgacgtgc tgcagacact gatgaacgat  1020
tttcagatcc tgccaatcgg cggagtgtac agctgcacg ctggcgacaa catctacctg  1080
aagttcaact ctaaggatca catccagaag accaacacat actggggcat catcctgatg  1140
ccagatctgc cctttatcag ctga                                         1164

SEQ ID NO: 27           moltype = DNA  length = 1152
FEATURE                 Location/Qualifiers
source                  1..1152
                        mol_type = other DNA
                        organism = Homo sapiens
SEQUENCE: 27
atgctgctgt tcctgctgtc tgccctggtg ctgctgaccc agccactggg ctacctggag    60
gccgagatga gacctattc ccaccgcaca atgccttctg cctgcacact ggtcatgtgc   120
agcagcgtgg agagcggcct gccaggaagg acggaagag atgaaggga ggaacccaga    180
ggcgagaagg gcgaccctgg cctgccagga gcagcaggac aggcaggaat gccaggccag   240
gccggccccg tgggccctaa gggcgacaat ggatccgtgg gagagccagg accaaagggc   300
gataccgcc cttctggacc acctggacca cagccgctgg ctggaccagg aggaagagag   360
ggacctctgg gcaagcaggg aaacatcgga ccacagggca gccaggccc taagggcgag   420
gccgccccca gggcgaagt gggcgcccct gcatgcaggg atccgccgg agccagggc   480
ctggccggac taagggcga gcgcggcgtg cctggagaga gggcgtgcc aggaaatca   540
ggcgcagcag gatctgccgg agcaatggga ccacagggca gcccggcgc cagagccct   600
ccaggcctga agggcgacaa gggaatccct gccgataagg gagcaaagg agagagccga   660
ctgccagacct ggcctccct gaggcagcag gtgaggccc tgcagggaca ggtgcagcac   720
ctgcaggccg ccttcagcca gtacaagaag gtggagctgt tccaaatgg cgagacagcc   780
aaggagccct gcatgccaa gttcggccca ctgccagca gtggcagat ggcctctagc   840
gagccccctt gcgtgaacaa ggtgagcgat tggaagctgg atatcctgca gaacggcctg   900
tacctgatct atgccaggt ggcccccaac gccaattaca acgacgtggc ccctttgag   960
```

```
gtgcggctgt ataagaacaa ggatatgatc cagaccctga caaataagtc taagatccag  1020
aacgtgggag gcacctacga gctgcacgtg ggcgacacaa tcgacctgat cttcaacagc  1080
gagcaccagg tgctgaagaa caatacatat tggggcatca tcctgctggc caaccccag   1140
tttatctcct ga                                                      1152

SEQ ID NO: 28           moltype = DNA  length = 597
FEATURE                 Location/Qualifiers
source                  1..597
                        mol_type = other DNA
                        organism = Mus musculus
SEQUENCE: 28
atggagggcg agggagtgca gcccctggat gagaacctgg agaacggctc ccggcctcgc   60
ttcaagtgga agaagaccct gcggctggtg gtgtctggaa tcaagggcgc cggaatgctg  120
ctgtgcttta tctacgtgtg cctgcagctg agctcctctc ccgccaagga tcccctct    180
cagaggctga gaggagctgt gaccaggtgc gaggacggaa agctgttcat cagctcctac  240
aagaacgagt accagacaat ggaggtgcag aacaacagcg tggtcatcaa gtgtgatggc  300
ctgtacatca tctacctgaa gggatccttc tttcaggagg tgaagatcga cctgcactt   360
cgggaggatc acaacccaat ctctatcccc atgctgaacg acggcaggag aatcgtgttc  420
acagtggtgg ccagcctggc tttaaggac aaggtgtacc tgaccgtgaa cgccccagat   480
acactgtgcg agcacctgca gatcaacgac ggagagctga tcgtggtgca gctgacccct  540
ggctactgtg ctccagaggg atcttaccac agcacagtga accaggtgcc cctgtga     597

SEQ ID NO: 29           moltype = DNA  length = 552
FEATURE                 Location/Qualifiers
source                  1..552
                        mol_type = other DNA
                        organism = Homo sapiens
SEQUENCE: 29
atggagaggg tgcagccct ggaggagaac gtgggaaatg ccgcccggcc tagattcgag    60
aggaacaagc tgctgctggt ggcctctgtg atccaggcc tgggcctgct gctgtgcttc   120
acctacatct gtctgcactt ttctgccctg caggtgagcc acagataccc ccgcatccag  180
agcatcaagt gcagttcac cgagtataag aaggagaagg gctttatcct gacatcccag   240
aaggaggacg agatcatgaa ggtgcagaac aattctgtga tcatcaactg cgatggcttc  300
tacctgatct ccctgaaggg ctatttttct caggagtga atatcagcct gcactatcag  360
aaggacgagg agccactgtt tcagctgaag aaggtgcgga gcgtgaattc cctgatgctg  420
gccagcctga cctacaagga caaggtgtat ctgaacgtga ccacagataa tacatccctg  480
gacgatttcc acgtgaacgg cggcgagctg atcctgatcc accagaatcc cggcgagttt  540
tgcgtgctgt ga                                                      552

SEQ ID NO: 30           moltype = DNA  length = 1215
FEATURE                 Location/Qualifiers
source                  1..1215
                        mol_type = other DNA
                        organism = Mus musculus
SEQUENCE: 30
atgctgccct tcctgtccat gctggtgctg ctggtgcagc tctgggcaa cctgggagcc    60
gagatgaagt ctctgagcca gagatccgtg ccaaacacct gcacactggt catgtgctct  120
cccaccgaga acggcctgcc tggaagggac ggaagagatg gaaggagggg acccgggga   180
gagaagggcg atcctggact gccaggacct atgggactga gcggcctgca gggaccaaca  240
ggccccgtgg gacctaaggg agagaacgga agcgccggag agccaggacc aaagggagag  300
aggggactgt ccggcccacc tggactgcct ggaatccctg gaccagctgg caaggaggga  360
ccttccggca agcagggaaa catcggacca cagggaaagc caggacctaa gggagaggct  420
ggaccaaagg gagaagtggg cgctccagga atgcagggct ctaccggagc caagggcagc  480
acaggaccta gggagagag gggagctcca ggagtgcagg gagcccccgg caacgctgga  540
gctgctggac cagctggacc agctgggcct cagggagccc caggctctag gggaccacca  600
ggcctgaagg gcgacagggg cgtgccagga gataggggca tcaagggaga gagcggcctg  660
ccagattccg ccgctctgag acagcagatg gaggccctga gggcaagct gcagcggctg  720
gaggtggctt tcagccacta ccagaaggcc gctctgtttc ctgacggcag ctcctctcca  780
gccaaggatc ctccaatcca gcggctgcgc ggagctgtga ccaggtgcga ggatggccag  840
ctgttcatca gctcctacaa gaacgagtac cagacaatgg aggtcagaa caactctgtg  900
gtcatcaagt gtgacggcct gtacatcatc tacctgaagg gcagcttctt tcaggaggtg  960
aagatcgacc tgcactttag agaggatcac aacccaatct ccatcccat gctgaacgac   1020
ggcaggagaa tcgtgttcac cgtggtggcc tctctggctt taaggacaa ggtgtacctg  1080
accgtgaacg cccccgatac actgtgcgag cacctgcaga tcaacgacgg cgagctgatc  1140
gtggtgcagc tgaccctggg atactgtgct ccagagggct cctaccactc tacagtgaac  1200
caggtgcctc tgtga                                                   1215

SEQ ID NO: 31           moltype = DNA  length = 1170
FEATURE                 Location/Qualifiers
source                  1..1170
                        mol_type = other DNA
                        organism = Homo sapiens
SEQUENCE: 31
atgctgctgt tcctgctgag cgccctggtg ctgctgaccc agccactggg ctacctggag    60
gccgagatga gaacctattc ccacagaaca atgcccttctg cctgcacact ggtcatgtgc  120
agcagcgtgg agtccggcct gccaggaagg gacggcagag atggcaggga gggccccag   180
ggcgagaagg gcgaccccgg cctgcctgga gcagcaggcc aggccggcat gccaggccag  240
gccgcccag tgggccccaa gggcgacaac ggcagcgtgg gcgagcccgg ccctaagggc  300
gataccggcc cctccggccc ccctggccca ccggcgtgc aggaccagc aggaagggag  360
```

```
ggaccactgg gcaagcaggg caatatcgga cctcagggca agcctggacc aaagggagag    420
gcaggaccaa agggagaagt gggcgcccct ggcatgcagg gatctgccgg agcccgggc     480
ctggccggcc ccaagggcga gagaggcgtg cccggcgaga ggggcgtgcc tgcaacaca     540
ggcgccgccg gctccgccgg cgccatggga cctcagggct ctccaggagc cagaggccct   600
ccaggcctga agggcgacaa gggaatccct ggcgataagg gagcaaaggg agagagcggc   660
ctgccagacg tggcctccct gcggcagcag gtgaggcccc tgcagggcca ggtgcagcac   720
ctgcaggcc ccttcagcca gtacaagaag gtggagctgt ttcctaatgg cgtgtctcac    780
cgctaccacc ggatccagag catcaaggtg cagttcaccg agtataagaa ggagaagggc   840
tttatcctga catctcagaa ggaggacgag atcatgaagt gcagaacaa tagcgtgatc    900
atcaactgcg atggcttcta cctgatcagc ctctgaagggct attttcccca ggaagtgaat  960
atctctctgc actatcagaa ggatgaggag cctctgtttc agctgaagaa ggtgagatct  1020
gtgaacagcc tgatggtggc ctccctgacc tacaaggaca aggtgtatct gaacgtgacc  1080
acagataata catctctgga cgatttccac gtgaacggcg gcgagctgat cctgatccac  1140
cagaatcccg gcgagttttg cgtgctgtga                                   1170

SEQ ID NO: 32         moltype = DNA   length = 969
FEATURE               Location/Qualifiers
source                1..969
                      mol_type = other DNA
                      organism = Mus musculus
SEQUENCE: 32
atgcagctga agtgtccatg cttcgtgtcc ctgggaacaa gacagcccgt ctggaagaaa    60
ctgcacgtga gctccggctt ctttagcggc ctggggctgt ttctgctgct gctgtctagt   120
ctgtgcgccg cttccgcaga gactgaagtc ggagccatgg tgggcagtaa cgtggtcctg   180
tcatgcatcg acccacaccg acggcatttc aacctgtctg gcctgtacgt gtattggcag   240
attgagaatc ccgaagtgtc agtcacctac tatctgcctt acaagagcc agggatcaac    300
gtggactcaa gctataaaaa taggggcac ctgtccctgg attctatgaa gcagggaaac    360
ttcagcctgt acctgaaaaa tgtgaccct caggacacac aggagttcac ttgtcgcgtc   420
tttatgaaca ctgcaaccga actggtgaag attctggagg aagtggtccg gctgagagtc   480
gcagccaact ttagcactcc tgtgatctct accagtgatt cctctaatcc aggccaggag   540
cggacatata cttgcatgtc taagaacgga tacccgaac ctaatctgta ttggatcaac    600
accacagaca atagtctgat tgataccgct ctgcagaaca atacagtcta cctgaacaag   660
ctggggctgt atgacgtgat ctctactctg cggctgccat ggaccagtag aggagatgtg   720
ctgtgctgcg tggagaacgt ggcctgcac cagaatatca cctcaattag ccaggctgag    780
tcctttaccg gcaacaatac aaagaatcct caggagacac ataacaatga actgaaagtg   840
ctggtgccag tgctgccgt cctggctgca gcagctttcg tgtcttttat catctacaga    900
aggacccgcc ctcaccgctc atacactgga cctaagaccg tgcagctgga actgacagac   960
catgcttga                                                          969

SEQ ID NO: 33         moltype = DNA   length = 909
FEATURE               Location/Qualifiers
source                1..909
                      mol_type = other DNA
                      organism = Homo sapiens
SEQUENCE: 33
atgcgtctgg gttcacctgg tctgctgttt ctgctgtttt caagtctgcg tgctgatact    60
caggagaagg aagtccggc tatggtcgga agtgacgtgg agtgtcatg cgctttgtccc   120
gaagggtccc ggttcgacct gaacgatgtc tacgtgtatt ggcagacctc tgagagtaag   180
accgtggtca cataccacat ccctcagaac tccagcctgg aaatgtggaa ttcaaggtat   240
cggaacagag ccctgatgtc ccctgctggc atgctgcggg gagacttctc tctgagactg   300
tttaatgtga caccacagga tgagcagaaa ttccattgcc tggtcctgtc acagtccctg   360
ggatttcagg aggtgctgag tgtcgaagtg actctgcacg tcgccgctaa tttctccgtg   420
cctgtggtca gcgcaccaca tagcccctct caggacgagc tgacctttac atgtacttcc   480
atcaacggct accccgcc taacgtgtac tggattaaca agactgacaa tagcctgctg    540
gatcaggcac tgcagaacga caccgtgttt ctgaatatgc aggacgtaca cgatgtggtc   600
agcgtcctgc gtattgccag gaccccatct gtgaacatcg ggtgctgtat tgaacgtgc    660
ctgctgcagc agaatctgac agtggggagc cagactggta atgacatcgg cgagagggat   720
aagattaccg aaaaccccgt gagtacaggc gagaagaacg cagccacatg gtcaatcctg   780
gctgtgctgt cctgctggt ggtcgtggct gtcgcaattg ctgggtgtg ccgcgatcgg    840
tgtctgcagc actcttatgc cggtgcttgg gcagtgagtc cagagactga actgaccggc   900
catgtctaa                                                          909

SEQ ID NO: 34         moltype = DNA   length = 1574
FEATURE               Location/Qualifiers
source                1..1574
                      mol_type = other DNA
                      organism = Mus musculus
SEQUENCE: 34
cttaagatgg aaactgatac tctgctgctc tgggtgctgc tcctctgggt gcctggttca    60
actggggaca ttcgacgggc tgacattgtg atgacccaga ccacactgag cctgcccgtg   120
tccctgggcg accaggccag catctcctgc cggagctccc agtctatcgt gcacagcaac   180
ggaaacacat acctggagtg gtatctgcag aagcctggcc agtccccaaa gctgctgatc   240
tacaaggtgt ccaacaggtt cagcggcgtg cctgaccgct tttctggaag cggctccgga   300
acagatttca cccctgaagat cagcagggtg gaggctgaag acctgggcgt gtactactgc   360
ttccagggat cccacgtgcc ttacaccttt ggcggaggca aaagctggaa gatcaagaga   420
gccgatgctg ctccaaccgt gtctggaagc ggaggcgggg ttctggagg cggtgggagc   480
ggtggcggag gtctgaggc taagctgcag gagagcggcc ccgtgctggt gaagcctgga   540
gccagcgtga agatgtcctg taaggcttct ggatacacct tcacagacta ctacatgaac   600
tgggtgaagc agagccacgg caagtccctg agtggatcg gagtgatcaa cccttacaac   660
```

```
ggcgacacct cttacaacca gaagtttaag ggcaaggcca ccctgacagt ggataagtct    720
agctccaccg cttacatgga gctgaacagc ctgacatccg aggattctgc cgtgtactac    780
tgtgctaggt actacggaag ctggttcgcc tactggggcc agggaacact gatcaccgtg    840
tccacagcca agaccacacc ccctagcgtg tacccctggc tcctaggtc tagcagaggc     900
tgcaaggcat gcatctgtac cgtgcccgag gtgagcagcg tgttcatctt tccacccaag    960
cccaaggacg tgctgaccat cacactgacc cctaaggtga catgcgtggt ggtggatatc   1020
agcaaggacg atccagaggt gcagttctcc tggtttgtgg acgatgtgga ggtgcacacc   1080
gcccagacac agccaaggga ggagcagttc aactccacct ttagatccgt gtctgagctg   1140
cccatcatgc accaggactg gctgaacgga aggagttca agtccgggt gaactccgcc    1200
gcttttcctg ctccaatcga gaagaccatc tctaagacaa agggccgccc aaaggctcca   1260
caggtgtaca ccatccctcc acccaaggag cagatggcta aggataaggt gagcctgacc   1320
tgtatgatca cagacttctt tcccgaggat atcacagtgg agtggcagtg aacggacag   1380
cctgccgaga actacaagaa cacccagcca atcatggaca cagatggctc ttacttcgtg   1440
tacagcaagc tgaacgtgca gaagtctaac tgggaggctg caacaccttc acctgcagc   1500
gtgctgcacg aaggtctcca taatcaccac accgaaaaga gcctcagtca cagccctggg   1560
aaatgaggcg cgcc                                                    1574

SEQ ID NO: 35          moltype = DNA  length = 1484
FEATURE                Location/Qualifiers
source                 1..1484
                       mol_type = other DNA
                       organism = Homo sapiens
SEQUENCE: 35
cttaagatgg aaactgacac cctgctgctg tgggtcctgc tgctgtgggt gcctggatcc     60
accggcgata tcgtgctgac ccagtctcct ggcacactga gtctgtcacc aggggagcga   120
gcaacactgt cttgtagagc cagccagtct gtgggaagct cctacctggc ttggtatcag   180
cagaagccag gccaggcacc caggctgctg atctactacga gccttcagccg ggccactggc  240
attccagaca ggttctctgg aagtggctca gggaccgact tcaccctgac catcagccga   300
ctggagcccg aagacttcgc cgtgtactat tgccagcagt acggctctag tccttggact   360
tttggacagg gcaccaaagt ggagatcaag gcggcggtcgg gaggctctgg gggaggcggg   420
agtggaggcg gggatcaca ggtccagctg gtggaaagcg gcggggagt ggtccagcca     480
ggccggagcc tgcggctgag ctgcgccgct tcaggattca cattttcaag ctataccatg   540
cactgggtcc ggcaggcacc agggaaggga ctggagtggg tgaccttcat cagctatgac   600
ggcaacaaca gtattacgc tgattccgtg aaagggaggt ttaccattag ccgcgacaac    660
tccaaaaata cactgtacct gcagatgaac agcctgcggg ccgaggatac tgctatctac   720
tattgcgcaa gaaccgggtg gctgggaccc ttcgactatt ggggccaggg gactctggtc   780
accgtgtcct ctgataagac acacacatgc cctccctgtc ctgcaccaga gctgctgggc   840
gggccatccg tgttcctgtt tccacccaag cctaaagaca ccctgatgat cagccggaca   900
cctgaagtca cttgcgtggt cgtggacgtg agtcacgagg atccagaagt caagtttaac   960
tggtacgtgg atggcgtcga ggtgcataat gccaagacca aacctcgcga ggaacagtac  1020
aatagcacat atcgagtcgt gtccgtcctg actgtgctgc atcaggattg gctgaacggc   1080
aaagagtata gtgcaaagt gagcaataag gcactgcctg ccccaatcga gaaacaatt    1140
tccaaggcta aaggcagcc cagggaacct caggtgtaca ctctgcctcc aagtcgcgag   1200
gaaatgacca gaaccaggt gagcctgacc tgtctggtga aagggttcta tccatcagac   1260
attgcagtgg agtgggaaag caatggacag cccgaaaaca attacaagac cacccccct   1320
gtgctggaca gcgatggctc cttctttctg tattctaagc tgactgtgga taaaagtcgc   1380
tggcagcagg ggaacgtctt tagctgttcc gtgatgcatg aggctctgca caatcattac   1440
acacgaagt ctctgagtct gtcacccggc aaatgaggcg cgcc                    1484

SEQ ID NO: 36          moltype = DNA  length = 632
FEATURE                Location/Qualifiers
misc_feature           1..632
                       note = CMV promoter
source                 1..632
                       mol_type = other DNA
                       organism = synthetic construct
SEQUENCE: 36
gttgacattg attattgact agttattaat agtaatcaat tacggggtca ttagttcata     60
gcccatatat ggagttccgc gttacataac ttacggtaaa tggcccgcct ggctgaccgc   120
ccaacgaccc ccgcccattg acgtcaataa tgacgtatgt tcccatagta acgccaatag   180
ggactttcca ttgacgtcaa tgggtggagt atttacggta aactgcccac ttggcagtac   240
atcaagtgta tcatatgcca agtacgcccc ctattgacgt caatgacggt aaatggcccg   300
cctggcatta tgcccagtac atgaccttat gggactttcc tacttggcag tacatctacg   360
tattagtcat cgctattacc atggtgatgc ggttttggca gtacatcaat gggcgtggat   420
agcggtttga ctcacgggga tttccaagtc tccaccccat tgacgtcaat gggagtttgt   480
tttggcacca aaatcaacgg gactttccaa aatgtcgtaa caactccgcc ccattgacgc   540
aaatgggcgg taggcgtgta cggtgggagg tctatataag cagagctctc tggctaacta   600
gagaacccac tgcttactgg cttatcgaaa tt                                 632

SEQ ID NO: 37          moltype = DNA  length = 394
FEATURE                Location/Qualifiers
misc_feature           1..394
                       note = RSV promoter
source                 1..394
                       mol_type = other DNA
                       organism = synthetic construct
SEQUENCE: 37
tgtacgggcc agatatacgc gtatctgagg ggactagggt gtgtttaggc gaaaagcggg     60
gcttcggttg tacgcggtta ggagtcccct caggatatag tagtttcgct tttgcatagg   120
```

```
gaggggggaaa tgtagtctta tgcaatacac ttgtagtctt gcaacatggt aacgatgagt    180
tagcaacatg ccttacaagg agagaaaaag caccgtgcat gccgattggt ggaagtaagg    240
tggtacgatc gtgccttatt aggaaggcaa cagacaggtc tgacatggat tggacgaacc    300
actgaattcc gcattgcaga gataattgta tttaagtgcc tagctcgata caataaacgc    360
catttgacca ttcaccacat tggtgtgcac ctcc                               394

SEQ ID NO: 38              moltype = DNA   length = 188
FEATURE                    Location/Qualifiers
misc_feature               1..188
                           note = BGH polyA
source                     1..188
                           mol_type = other DNA
                           organism = synthetic construct
SEQUENCE: 38
ctgtgccttc tagttgccag ccatctgttg tttgcccctc ccccgtgcct tccttgaccc    60
tggaaggtgc cactcccact gtcctttcct aataaaatga ggaaattgca tcgcattgtc    120
tgagtaggtg tcattctatt ctggggggtg ggtggggca ggacagcaag ggggaggatt    180
gggaagac                                                            188

SEQ ID NO: 39              moltype = DNA   length = 249
FEATURE                    Location/Qualifiers
misc_feature               1..249
                           note = SV40 late polyA
source                     1..249
                           mol_type = other DNA
                           organism = synthetic construct
SEQUENCE: 39
gacatgataa gatacattga tgagtttgga caaaccacaa ctagaatgca gtgaaaaaaa    60
tgctttattt gtgaaatttg tgatgctatt gctttatttg tgaaatttgt gatgctattg    120
ctttatttgt aaccattata agctgcaata aacaagttaa caacaacaat tgcattcatt    180
ttatgtttca ggttcagggg gaggtgtggg aggttttttta aagcaagtaa aacctctaca    240
aatgtggta                                                           249

SEQ ID NO: 40              moltype = DNA   length = 345
FEATURE                    Location/Qualifiers
misc_feature               1..345
                           note = SV40 enhancer promoter
source                     1..345
                           mol_type = other DNA
                           organism = synthetic construct
SEQUENCE: 40
gctgtggaat gtgtgtcagt tagggtgtgg aaagtcccca ggctcccag caggcagaag    60
tatcaaagc atgcatctca attagtcagc aaccaggtgt ggaaagtccc caggctcccc    120
agcaggcaga agtatgcaaa gcatgcatct caattagtca gcaaccatag tcccgcccct    180
aactccgccc atcccgcccc taactccgcc cagttccgcc cattctccgc cccatggctg    240
actaattttt tttatttatg cagaggccga ggccgcctcg gcctctgagc tattccagaa    300
gtagtgagga ggcttttttg gaggcctagg cttttgcaaa aagct                   345

SEQ ID NO: 41              moltype = DNA   length = 99
FEATURE                    Location/Qualifiers
misc_feature               1..99
                           note = Rabbit beta-globin polyA
source                     1..99
                           mol_type = other DNA
                           organism = synthetic construct
SEQUENCE: 41
gacctctggc taataaagga aatttatttt cattgcaata gtgtgttgga attttttgtg    60
tctctcactc ggaaggacat atgggagggc aaatcattt                           99

SEQ ID NO: 42              moltype = DNA   length = 723
FEATURE                    Location/Qualifiers
misc_feature               1..723
                           note = GFP
source                     1..723
                           mol_type = other DNA
                           organism = synthetic construct
SEQUENCE: 42
accatggtga gcaagggcga ggagctgttc accggggtgg tgcccatcct ggtcgagctg    60
gacggcgacg taaacggcca caagttcagc gtgtccggcg agggcgaggg cgatgccacc    120
tacggcaagc tgaccctgaa gttcatctgc accaccggca agctgcccgt gccctggccc    180
accctcgtga ccaccctgac ctacggcgtg cagtgcttca gccgctaccc cgaccacatg    240
aagcagcacg acttcttcaa gtccgccatg cccgaaggct acgtccagga gcgcaccatc    300
ttcttcaagg acgacggcaa ctacaagacc cgcgccgagg tgaagttcga gggcgacacc    360
ctggtgaacc gcatcgagct gaagggcatc gacttcaagg aggacggcaa catcctgggg    420
cacaagctgg agtacaacta caacagccac aacgtctata tcatggccga caagcagaag    480
aacggcatca aggtgaactt caagatccgc cacaacatcg aggacggcag cgtgcagctc    540
gccgaccact accagcagaa cacccccatc ggcgacggcc ccgtgctgct gcccgacaac    600
cactacctga gcacccagtc cgccctgagc aaagacccca acgagaagcg cgatcacatg    660
gtcctgctgg agttcgtgac cgccgccggg atcactctcg gcatggacga gctgtacaag    720
```

```
                                                         taa                                                    723

SEQ ID NO: 43           moltype = DNA  length = 454
FEATURE                 Location/Qualifiers
misc_feature            1..454
                        note = MoMuLV LTR
source                  1..454
                        mol_type = other DNA
                        organism = synthetic construct
SEQUENCE: 43
ttaattaagt aacgccattt tgcaaggcat ggaaaaatac ataactgaga atagagaagt   60
tcagatcaag gtcaggaaca gatggaacag ctgaatatgg gccaaacagg atatctgtgg  120
taagcagttc ctgccccggc tcagggccaa gaacagatgg aacagctgaa tatgggccaa  180
acaggatatc tgtggtaagc agttcctgcc ccggctcagg ccaagaaca gatggtcccc   240
agatgcggtc cagccctcag cagtttctag aaaccatca gatgtttcca gggtgcccca   300
aggacctgaa atgaccctgt gccttatttg aactaaccaa tcagttcgct tctcgcttct  360
gttcgcgcgc ttctgctccc cgagctcaat aaaagagccc acaacccctc actcggggcg  420
ccagtcctcc gattgactga gtcgcccgct taag                              454

SEQ ID NO: 44           moltype = DNA  length = 1349
FEATURE                 Location/Qualifiers
misc_feature            1..1349
                        note = EF1alpha promoter
source                  1..1349
                        mol_type = other DNA
                        organism = synthetic construct
SEQUENCE: 44
ttaattaaga gtaattcata caaaaggact cgcccctgcc ttggggaatc ccagggaccg   60
tcgttaaact cccactaacg tagaacccag agatcgctgc gttccgcc cctcacccgc    120
ccgctctcgt catcactgag gtggagaaga gcatgcgtga ggctccggtg cccgtcagtg  180
ggcagagcgc acatcgccca cagtccccga aagttggggg gaggggtcg gcaattgaac   240
cggtgcctag agaaggtggc gcggggtaaa ctgggaaagt gatgtcgtgt actggctccg  300
ccttttcccc gagggtgggg gagaaccgta tataagtgca gtagtcgccg tgaacgttct  360
ttttcgcaac gggtttgccg ccagaacaca ggtaagtgcc gtgtgtggtt cccgcgggcc  420
tggcctcttt acgggttatg gcccttgcgt gccttgaatt acttccacgc ccctggctgc  480
agtacgtgat tcttgatccc gagcttcggg ttggaagtgg gtgggagagt tcgaggcctt  540
gcggttaagg agcccttcg cctcgtgctt gagttgaggc ctggcttggg cgctggggcc   600
gccgcgtgcg aatctggtgg caccttcgcg cctgtctcgc tgctttcgat aagtctctag  660
ccatttaaaa ttttttgatga cctgctgcga cgctttttttt ctggcaagat agtcttgtaa  720
atgcgggcca agatctgcac actggtattt cggttttttgg ggccgcgggc ggcgacgggg  780
cccgtgcgtc ccagcgcaca tgttcggcga ggcggggcct gcgagcgcgg ccaccgagaa  840
tcggacgggg gtagtctcaa gctggccggc ctgctctggt gcctggcctc gcgccgccgt  900
gtatcgcccc gccctgggcg gcaaggctgg cccggtcggc accagttgcg tgagcggaaa  960
gatggccgct tccggccct gctgcaggga gctcaaaatg gaggacgcgg cgctcggag   1020
agcgggcggt gagtcaccc acacaaagga aaagggcctt tccgtcctca gccgtcgctt  1080
catgtgactc cacggagtac cgggcgccgt ccaggcacct cgattagttc tcgagctttt  1140
ggagtacgtc gtctttaggt tgggggggagg ggttttatgc gatggagttt ccccacactg  1200
agtgggtgga gactgaagtt aggccagctt ggcacttgat gtaattctcc ttggaatttg  1260
cccttttttga gtttggatct tggttcattc tcaagcctca gacagtggtt caaagttttt  1320
ttcttccatt tcaggtgtcg tgacttaag                                    1349

SEQ ID NO: 45           moltype = DNA  length = 481
FEATURE                 Location/Qualifiers
misc_feature            1..481
                        note = HGH polyA
source                  1..481
                        mol_type = other DNA
                        organism = synthetic construct
SEQUENCE: 45
gacgggtggc atccctgtga cccctcccca gtgcctctcc tggccctgga agttgccact   60
ccagtgccca ccagccttgt cctaataaaa ttaagttgca tcattttgtc tgactaggtg  120
tccttctata atattatggg gtggaggggg gtggtatgga gcaagggca agttgggaag   180
acaacctgta gggcctgcgg ggtctattgg gaaccaagct ggagtgcagt ggcacaatct  240
tggctcactg caatctccgc ctcctgggtt caagcgattc tcctgcctca gcctcccgag  300
ttgttgggat tccaggcatg catgaccagg ctcagctaat ttttgttttt ttggtagaga  360
cggggtttca ccatattggc caggctggtc tccaactcct aatctcaggt gatctaccca  420
ccttggcctc ccaaattgct gggattacag gcgtgaacca ctgctccctt ccctgtcctt  480
t                                                                  481
```

ONCOLYTIC VIRUS STRAIN

CROSS-REFERENCE TO RELATED APPLICATIONS

This application is a continuation of U.S. patent application Ser. No. 16/740,203 filed Jan. 10, 2020, which is a continuation of U.S. patent application Ser. No. 16/068,826 filed Jul. 9, 2018, issued Feb. 25, 2020 as U.S. Pat. No. 10,570,377, which is a national phase application under 35 U.S.C. § 371 that claims priority to International Application No. PCT/GB2017/050037 filed Jan. 9, 2017, which claims priority to Great Britain Patent Application Nos. 1600380.8, 1600381.6 and 1600382.4 filed Jan. 8, 2016, all of which are incorporated herein by reference in their entirety.

INCORPORATION OF SEQUENCE LISTING

The instant application contains a Sequence Listing, named "SeqLst_KEMPP0085USC2" (78,228 bytes; created Dec. 20, 2022) which has been submitted electronically in XML format and is hereby incorporated by reference in its entirety.

FIELD OF THE INVENTION

The invention relates to an oncolytic immunotherapeutic agent and to the use of the oncolytic immunotherapeutic agent in treating cancer.

BACKGROUND TO THE INVENTION

Viruses have a unique ability to enter cells at high efficiency. After entry into cells, viral genes are expressed and the virus replicates. This usually results in the death of the infected cell and the release of the antigenic components of the cell as the cell ruptures as it dies. As a result, virus mediated cell death tends to result in an immune response to these cellular components, including both those derived from the host cell and those encoded by or incorporated into the virus itself.

Viruses also engage with various mediators of the innate immune response as part of the host response to the recognition of a viral infection through e.g. toll-like receptors and cGAS/STING signalling resulting in the activation of interferon responses and inflammation which are also immunogenic signals to the host. These immune responses may result in the immunogenic benefit to cancer patients such that immune responses to tumor antigens provide a systemic overall benefit resulting in the treatment of tumors which have not been infected with the virus, including micro-metastatic disease, and providing vaccination against relapse.

The combined direct ('oncolytic') effects of the virus, and immune responses against tumor antigens (including non-self 'neo-antigens', i.e. derived from the particular mutated genes in individual tumors) is termed 'oncolytic immunotherapy'.

Viruses may also be used as delivery vehicles ('vectors') to express heterologous genes inserted into the viral genome in infected cells. These properties make viruses useful for a variety of biotechnology and medical applications. For example, viruses expressing heterologous therapeutic genes may be used for gene therapy. In the context of oncolytic immunotherapy, delivered genes may include those encoding specific tumor antigens, genes intended to increase the immunogenicity of antigens released following virus replication and cell death, to increase the general immune activation status of the tumor, or to increase the direct oncolytic properties (i.e. cytotoxic effects) of the virus.

It has been demonstrated that a number of viruses including herpes simplex virus (HSV) have utility in the oncolytic treatment of cancer. HSV for use in the oncolytic treatment of cancer must be disabled such that it is no longer pathogenic, but can still enter into and kill tumor cells. A number of disabling mutations to HSV, including disruption of the genes encoding ICP34.5, ICP6, and/or thymidine kinase, have been identified which do not prevent the virus from replicating in culture or in tumor tissue in vivo, but which prevent significant replication in normal tissue. HSVs in which only the ICP34.5 genes have been disrupted replicate in many tumor cell types in vitro, and replicate selectively in tumor tissue, but not in surrounding tissue, in mouse tumor models. Clinical trials of ICP34.5 deleted, or ICP34.5 and ICP6 deleted, HSV have also shown safety and selective replication in tumor tissue in man.

As discussed above, an oncolytic virus, including HSV, may also be used to deliver a therapeutic gene in the treatment of cancer. An ICP34.5 deleted virus of this type additionally deleted for ICP47 and encoding a heterologous gene for GM-CSF has also been tested in clinical trials, including a phase 3 trial in melanoma in which safety and efficacy in man was shown. The trial data demonstrated that tumor responses could be seen in injected tumors, and to a lesser extent in uninjected tumors. Responses tended to be highly durable (months-years), and a survival benefit appeared to be achieved in responding patients. Each of these indicated engagement of the immune system in the treatment of cancer in addition to the direct oncolytic effect. However, this and other data with oncolytic viruses generally showed that not all tumors respond to treatment and not all patients achieve a survival advantage. Thus, improvements to the art of oncolytic therapy and oncolytic immunotherapy are clearly needed. These may serve to increase the direct oncolytic effects of therapy, the anti-tumor immune stimulating effects of the therapy, or both of these effects together.

Recently it has been shown that oncolytic immunotherapy can result in additive or synergistic therapeutic effects in conjunction with immune checkpoint blockade (i.e. inhibition or 'antagonism' of immune checkpoint pathways), also referred to as immune co-inhibitory pathway blockade. Checkpoint (immune co-inhibitory pathway) blockade is intended to block host immune inhibitory mechanisms which usually serve to prevent the occurrence of auto-immunity. However, in cancer patients these mechanisms can also serve to inhibit or block the potentially beneficial effects of any immune responses induced to tumors. Alternatively, immune responses may not be fully potentiated due to a lack of activation or lack of full activation of immune potentiating pathways. Therefore, drugs which alleviate these blocks or stimulate immune potentiating pathways (i.e. which activate, or are 'agonists' of these immune potentiating pathways) are attractive for testing and developing cancer treatments. Targets for such approved or experimental drugs include CTLA-4, PD-1. PD-L1, LAG-3. TIM-3. VISTA, CSF1R, IDO, CEACAM1, GITR, 4-1-BB, KIR, SLAMF7, OX40, CD40, ICOS or CD47.

For these approaches to be successful, pre-existing immune responses to tumors are needed, i.e. so that a pre-existing immune response can be potentiated or a block to an anti-tumor immune response can be relieved. The presence of an inflamed tumor micro-environment, which is indicative of such an ongoing response, is also needed.

Pre-existing immune responses to tumor neo-antigens appear to be particularly important for the activity of immune co-inhibitory pathway blockade and related drugs. Only some patients may have an ongoing immune response to tumor antigens including neoantigens and/or an inflamed tumor microenvironment, both of which are required for the activity of these drugs. Therefore, oncolytic agents which can induce immune responses to tumor antigens, including neoantigens, and/or which can induce an inflamed tumor microenvironment are attractive for use in combination with immune co-inhibitory pathway blockade and immune potentiating drugs. This likely also explains the promising combined anti-tumor effects of oncolytic agents and immune co-inhibitory pathway blockade in mice and humans that have so far been observed.

The indoleamine 2,3-dioxygenase (IDO) pathway contributes to tumor-induced tolerance by creating a tolerogenic environment in the tumor and the tumor-draining lymph nodes, both by direct suppression of T cells and enhancement of local regulatory T cell (Treg)-mediated immunosuppression. IDO catalyses the rate-limiting step of tryptophan degradation along the kynurenine pathway, and both the reduction in local tryptophan concentration and the production of immunomodulatory tryptophan metabolites contribute to the immunosuppressive effects of IDO. IDO is chronically activated in many cancer patients with IDO activation correlating with more extensive disease. It can also function as an antagonist to other activators of antitumor immunity. Therefore, inhibitors of the IDO pathway are being developed as anticancer agents, particularly in combination with checkpoint blockade agents such as those which target CTLA-4, PD-1 or PDL-1. IDO inhibitors may also be synergistic with oncolytic immunotherapy, including together with drugs targeting other immune checkpoint or immune co-stimulatory pathways.

SUMMARY OF THE INVENTION

The invention provides improved oncolytic viruses. The improved oncolytic viruses have improved direct oncolytic effects. The improved direct oncolytic effects provided by the viruses of the invention will also lead to improved systemic anti-tumor immune effects. The improved direct oncolytic effects provided by the viruses of the invention will also lead to improved therapeutic effects in patients. Enhanced replication in and killing of tumor cells will result in enhanced tumor antigen release and enhanced systemic immune responses to the released antigens. The expression levels of any genes inserted to augment the direct oncolytic effects and/or immune stimulation will also be increased.

Virus species naturally exist in a range of variants (strains) within the natural population which may differ by a small or larger number of nucleotides while still retaining the antigenic characteristics and sufficient sequence identity to still be recognized as the same virus species. These strains, due to their differing sequences, may exhibit a range of differing properties, including properties which have been selected for by natural selection in their natural host or hosts (for example the ability to infect or replicate in the target cell types of the virus in question, spread between these cells, or to evade the host innate or adaptive immune system, or to spread between infected individuals of the host species) and properties which have not been specifically selected for (e.g. the ability to replicate in and kill or spread between cell types which are not the natural targets of the virus in question, including tumor or other non-target cell types or tissues). The inventors have recognised that sampling a range of viral strains of a particular viral species which are present in the natural host population (in the case of viruses infecting humans, here termed 'clinical isolates') and comparing these to each other to select for the strain with the best properties for the intended purpose for which it is to be used (e.g. infection and killing of tumor cells) can be used to identify a virus (i.e. a virus strain) with optimal properties for that purpose. The optimal properties may be properties that offer the best starting point for development to produce a virus that can be used as a therapeutic. A virus identified by this approach is likely to have more optimal properties for the intended purpose than a 'prototype' or 'laboratory' virus strain or a clinical strain which has not been selected for the required property or properties from a broad group of viral strains. This is because the full biological complexity in the natural population, particularly with respect to the particular desirable property or properties, is unlikely to have been sampled through taking a narrow approach to screening for the desired property or properties, bearing in mind the degree of sequence variation present in natural virus populations. In particular, these may vary in sequence within an infected host (as is often the case with RNA or retroviral populations where so-called quasi-species are often present), between individual infected hosts, or between different geographically separated viral populations.

Viruses of the invention have therefore been selected by sampling a range of viral strains present in the natural population of a particular viral species and testing these against each other for the desired property or properties (e.g. the ability to infect and kill tumor cells). The virus strain or strains with the best properties for the intended purpose are used for further development.

Where the intended use is oncolytic viral therapy, taking such an approach provides an improved starting point for development of an oncolytic agent, which may require further manipulation of the advantageous virus strains. Such manipulation includes the deletion of viral genes to provide, for example, tumor selectivity, and/or the insertion of exogenous genes to improve oncolytic or immune potentiating properties further.

The viruses of the invention therefore include novel clinical isolates of a viral species that have better anti-tumor effects than the other clinical isolates to which they were compared and through which comparison they were identified. In particular, the clinical isolates of the invention kill tumor cell lines in vitro more quickly and/or at a lower dose than these reference clinical isolates of the same virus type. Typically, a clinical isolate of the invention will have been identified through comparison of >5 clinical isolates of a viral species for the required property or properties, preferably through comparison of >10 clinical isolates of the viral species, and more preferably through comparison of >20 clinical isolates of the viral species. A clinical isolate of the invention typically shows better tumor cell killing activity than $3/5$, $6/10$ or $11/20$ths, preferably better than $4/5$, $8/10$ or $17/20$ths, more preferably better than $9/10$ or $19/20$ths of the viral strains tested.

Typically, a clinical isolate of the invention can kill two or more tumor cell lines in vitro within 24 to 48 hours after infection at a multiplicity of infection (MOI) of 0.01 to 0.001 or less.

The clinical isolates of the invention may be modified to further enhance their anti-tumor effects. The genome of a clinical isolate of the invention may be modified to delete or alter expression of one or more viral genes, and/or the genome of the clinical isolate may be modified to express one or more heterologous genes, such as genes encoding a fusogenic protein and/or an immune stimulatory molecule or molecules.

Oncolytic viruses of the invention provide improved treatment of cancer through improved direct oncolytic effects, viral replication and spread through tumors, which (i) increases the amount of tumor antigens, including neoantigens, which are released for the induction of an anti-tumor immune response; and (ii) enhances the expression of the virus-encoded immune stimulatory molecule(s). Expression of immune stimulatory molecule(s) by the virus can further enhance and potentiate the anti-tumor immune effect. Expression of fusogenic protein(s) by the virus can further enhance viral spread through tumors. Expression of fusogenic protein(s) by the virus can further enhance tumor cell killing.

Anti-tumor efficacy of an oncolytic virus of the invention is achieved when the virus is used as a single agent and also when the virus is used in combination with other anti-cancer modalities, including chemotherapy, treatment with targeted agents, radiation, immune checkpoint blockade (i.e. administration of one or more antagonist of an immune co-inhibitory pathway) and/or immune potentiating drugs (e.g. one or more agonists of an immune co-stimulatory pathway). The improved direct oncolytic effects (i.e. virus replication in, spread between, and direct killing of tumor cells) and improved systemic anti-tumor immune effects of the viruses of the invention improve on the combined benefits of oncolytic therapy and immune co-inhibitory pathway blockade and/or immune co-stimulatory pathway activation.

Accordingly, the present invention provides an oncolytic virus which is, or is derived from, a clinical isolate which has been selected by comparing the abilities of a panel of three or more clinical isolates of the same viral species to kill tumor cells of two or more tumor cell lines in vitro and selecting a clinical isolate which is capable of killing cells of two or more tumor cell lines more rapidly and/or at a lower dose in vitro than one or more of the other clinical isolates in the panel. The clinical isolate may be modified. A modified clinical isolate may have mutations, such as deletions in the viral genome and/or may express one or more heterologous genes.

The virus may be a strain of any virus species which may be used for the oncolytic treatment of cancer, including strains of herpes virus, pox virus, adenovirus, retrovirus, rhabdovirus, paramyxovirus or reovirus. The virus is preferably a herpes simplex virus (HSV), such as HSV1. The HSV typically does not express functional ICP34.5 and/or functional ICP47 and/or expresses the US11 gene as an immediate early gene.

The virus may comprise (i) a fusogenic protein-encoding gene; and/or (ii) an immune stimulatory molecule or an immune stimulatory molecule-encoding gene. The virus may encode more than one fusogenic protein and/or more than one immune stimulatory molecule. The fusogenic protein is preferably the glycoprotein from gibbon ape leukemia virus (GALV) and has the R transmembrane peptide mutated or removed (GALV-R-). The immune stimulatory molecule is preferably GM-CSF and/or an agonist of an immune co-stimulatory pathway including GITRL, 4-1-BBL, OX40L, ICOSL or CD40L or a modified version in each case thereof, or a protein capable of blocking signaling through CTLA-4, for example an antibody or a fragment thereof which binds CTLA-4.

The invention also provides:
a pharmaceutical composition comprising a virus of the invention and a pharmaceutically acceptable carrier or diluent;
the virus of the invention for use in a method of treating the human or animal body by therapy;
the virus of the invention for use in a method of treating cancer, wherein the method optionally comprises administering a further anti-cancer agent;
a product of manufacture comprising a virus of the invention in a sterile vial, ampoule or syringe;
a method of treating cancer, which comprises administering a therapeutically effective amount of a virus or a pharmaceutical composition of the invention to a patient in need thereof, wherein the method optionally comprises administering a further anti-cancer agent;
use of a virus of the invention in the manufacture of a medicament for use in a method of treating cancer, wherein the method optionally comprises administering a further anti-cancer agent, which is optionally an antagonist of an immune co-inhibitory pathway, or an agonist of an immune co-stimulatory pathway;
a method of treating cancer, which comprises administering a therapeutically effective amount of an oncolytic virus, an inhibitor of the indoleamine 2,3-dioxygenase (IDO) pathway and a further antagonist of an immune co-inhibitory pathway, or agonist of an immune co-stimulatory pathway to a patient in need thereof; and
a method of selecting an oncolytic virus, the method comprising:
(i) comparing the abilities of a panel of three or more clinical isolates of the same viral strain to kill tumor cells of two or more tumor cell lines in vitro;
(ii) scoring the abilities of each of the panel of viruses to kill tumor cells; (iii) selecting a virus which has one of the best scores;
(iv) optionally modifying the virus to inactivate one or more viral genes; and/or
(v) optionally modifying the virus to express one or more immune stimulatory molecule encoding genes and/or one or more fusogenic protein-encoding genes.

The further anti-cancer agent may be an antagonist of an immune co-inhibitory pathway or an agonist of an immune co-stimulatory pathway

BRIEF DESCRIPTION OF THE FIGURES

FIG. 1 also shows similar exemplary viruses of the invention expressing only a GALV-R-encoding gene (second panel), or only a GM-CSF-encoding gene (third panel) Also shown is an exemplary virus in which the ICP34.5 gene and the ICP47 gene are deleted.

FIGS. 5A-5K depict structures of HSV1 viruses modified by the deletion of ICP34.5 and ICP47 such that the US11 gene is under control of the ICP457 immediate early promoter and containing heterologous genes in the ICP34.5 locus. The viruses were constructed using the RH018A strain unless otherwise stated in the Figure.

FIG. 11A shows that using Virus 16 and anti-PD1 in combination has a better anti-tumor effect than using either anti-PD1 or the virus alone. FIG. 11B shows that the anti-tumor effect of Virus 16 in combination with anti-CTLA-4 was better than the anti-tumor effect of either Virus 16 or anti-CTLA-4 alone. FIG. 11C shows that enhanced tumor reduction was observed using Virus 16 together with both anti-PD1 and IDO inhibition as compared to anti-PD1 and 1-MT inhibition in the absence of the virus.

FIGS. 12A-12D show the enhanced anti-tumor activity of Virus 16 in combination with immune checkpoint blockade in mouse A20 tumors in both flanks of Balb/c mice as compared to either virus alone or checkpoint blockade alone (anti-PD1).

BRIEF DESCRIPTION OF THE SEQUENCE LISTING

Figure 1:
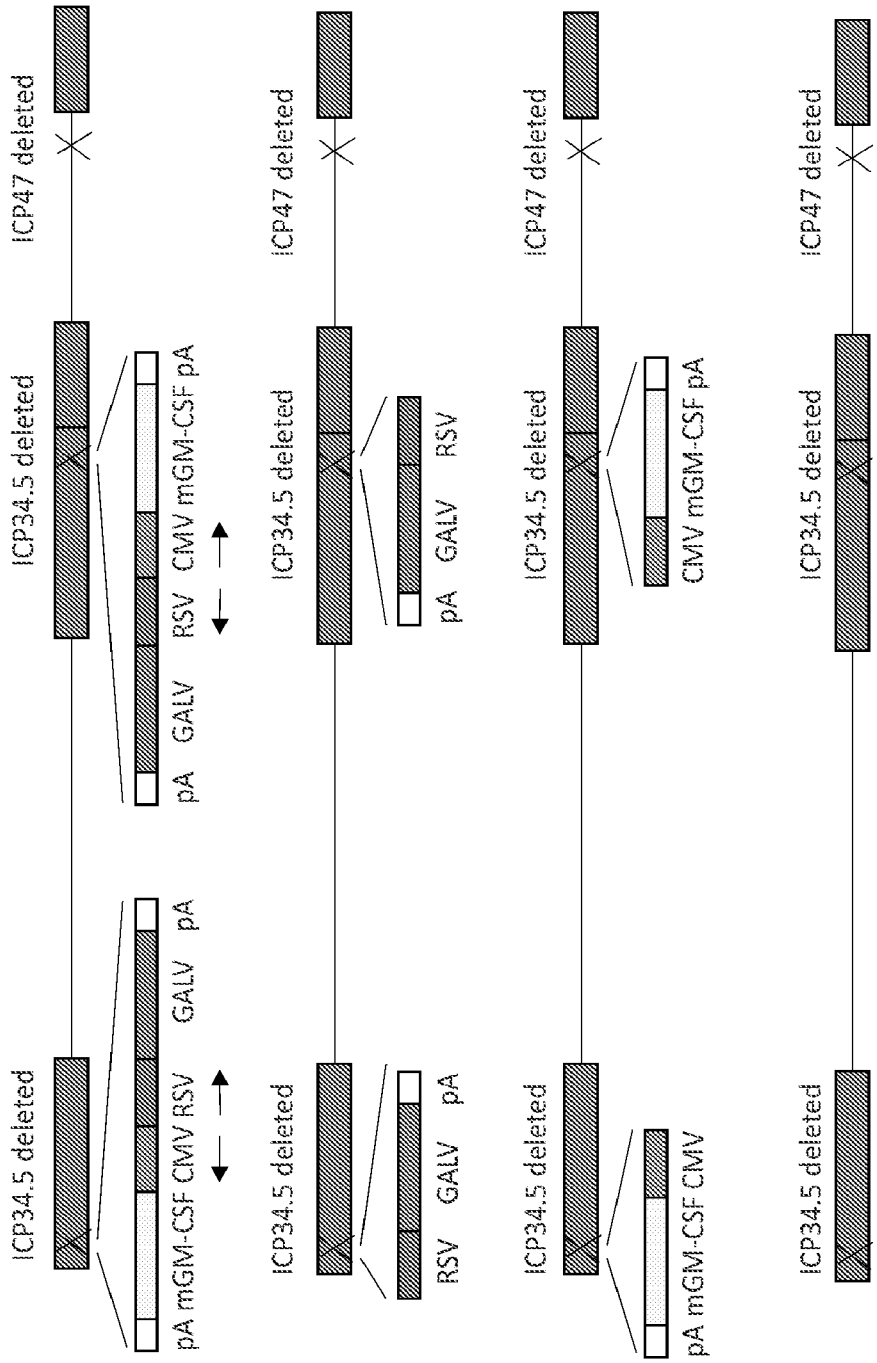
FIG. 1 depicts the structure of an exemplary virus of the invention that comprises a gene encoding GALV-R- and a gene encoding GM-CSF inserted into the ICP34.5 gene locus, and in which the ICP47 gene is deleted such that the US11 gene is under the control of the ICP47 immediate early promoter (top panel).
Figure 2:
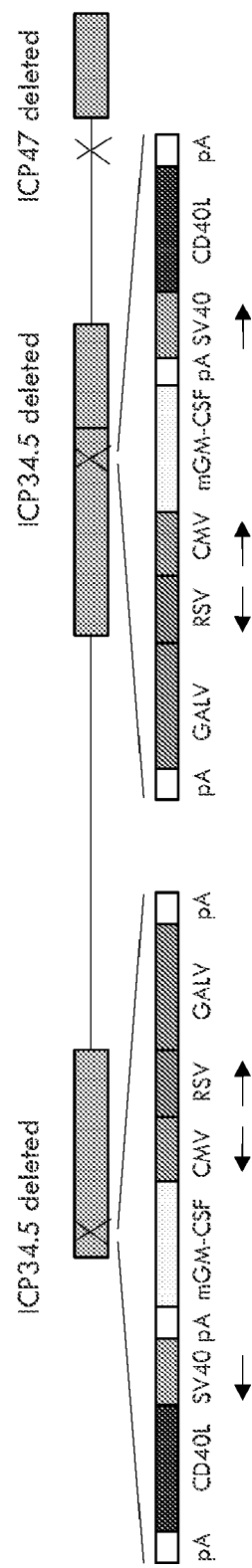
FIG. 2 depicts the structure of an exemplary virus of the invention that comprises a gene encoding GALV-R-, a gene encoding GM-CSF and a gene encoding CD40L.

SEQ ID NO: 1 is the nucleotide sequence of mouse GM-CSF.

SEQ ID NO: 2 is the nucleotide sequence of a codon optimized version of mouse GM-CSF.

SEQ ID NO: 3 is the nucleotide sequence of human GM-CSF.

SEQ ID NO: 4 is the nucleotide sequence of a codon optimized version of human GM-CSF.

SEQ ID NO: 5 is the amino acid sequence of mouse GM-CSF.

SEQ ID NO: 6 is the amino acid sequence of human GM-CSF.

SEQ ID NO: 7 is the nucleotide sequence of GALV-R-.

SEQ ID NO: 8 is the nucleotide sequence of a codon optimized version of GALV-R- (the first three nucleotides are optional).

SEQ ID NO: 9 is the amino acid sequence of GALV-R-.

SEQ ID NO: 10 is the nucleotide sequence of a codon optimized version of a human membrane bound version of CD40L.

SEQ ID NO: 11 is the amino acid sequence of a human membrane bound version of CD40L.

SEQ ID NO: 12 is the nucleotide sequence of a codon optimized version of a multimeric secreted version of human CD40L.

SEQ ID NO: 13 is the amino acid sequence of a multimeric secreted version of human CD40L.

SEQ ID NO: 14 is the nucleotide sequence of a codon optimized version of a multimeric secreted version of mouse CD40L.

SEQ ID NO: 15 is the amino acid sequence of a multimeric secreted version of mouse CD40L.

SEQ ID NO: 16 is a codon optimized version of the nucleotide sequence of wild-type human CD40L.

SEQ ID NO: 17 is the amino acid sequence of wild-type human CD40L.

SEQ ID NO: 18 is a codon optimized version of the nucleotide sequence of wild-type mouse CD40L.

SEQ ID NO: 19 is the amino acid sequence of wild-type mouse CD40L.

SEQ ID NO: 20 is the nucleotide sequence of a codon optimized version of murine 4-1BBL.

SEQ ID NO: 21 is the nucleotide sequence of a codon optimized version of human 4-1BBL.

SEQ ID NO: 22 is the nucleotide sequence of a codon optimized version of secreted mouse 4-1BBL.

SEQ ID NO: 23 is the nucleotide sequence of a codon optimized version of human secreted 4-1BBL.

SEQ ID NO: 24 is the nucleotide sequence of a codon optimized version of murine GITRL.

SEQ ID NO: 25 is the nucleotide sequence of a codon optimized version of human GITRL.

SEQ ID NO: 26 is the nucleotide sequence of a codon optimized version of secreted murine GITRL.

SEQ ID NO: 27 is the nucleotide sequence of a codon optimized version of secreted human GITRL.

SEQ ID NO: 28 is the nucleotide sequence of a codon optimized version of murine OX40L.

SEQ ID NO: 29 is the nucleotide sequence of a codon optimized version of human OX40L.

SEQ ID NO: 30 is the nucleotide sequence of a codon optimized version of secreted murine OX40L.

SEQ ID NO: 31 is the nucleotide sequence of a codon optimized version of secreted human OX40L.

SEQ ID NO: 32 is the nucleotide sequence of a codon optimized version of murine ICOSL.

SEQ ID NO: 33 is the nucleotide sequence of a codon optimized version of human ICOSL.

SEQ ID NO: 34 is the nucleotide sequence of a murine scFv CTLA-4 antibody. The first six and last eight nucleotides are restriction sites added for cloning purposes.

SEQ ID NO: 35 is the nucleotide sequence of a murine scFv CTLA-4 antibody. The first six and last eight nucleotides are restriction sites added for cloning purposes.

SEQ ID NO: 36 is the nucleotide sequence of the CMV promoter.

SEQ ID NO: 37 is the nucleotide sequence of the RSV promoter.

SEQ ID NO: 38 is the nucleotide sequence of BGH polyA.

SEQ ID NO: 39 is the nucleotide sequence of SV40 late polyA.

SEQ ID NO: 40 is the nucleotide sequence of the SV40 enhancer promoter.

SEQ ID NO: 41 is the nucleotide sequence of rabbit beta-globulin (RBG) polyA.

SEQ ID NO: 42 is the nucleotide sequence of GFP.

SEQ ID NO: 43 is the nucleotide sequence of the MoMuLV LTR promoter.

SEQ ID NO: 44 is the nucleotide sequence of the EF1a promoter.

SEQ ID NO: 45 is the nucleotide sequence of HGH polyA.

DETAILED DESCRIPTION OF THE INVENTION

Oncolytic Virus

The virus of the invention is oncolytic. An oncolytic virus is a virus that infects and replicates in tumor cells, such that the tumor cells are killed. Therefore, the virus of the invention is replication competent. Preferably, the virus is selectively replication competent in tumor tissue. A virus is selectively replication competent in tumor tissue if it replicates more effectively in tumor tissue than in non-tumor tissue. The ability of a virus to replicate in different tissue types can be determined using standard techniques in the art.

The virus of the invention may be any virus which has these properties, including a herpes virus, pox virus, adenovirus, retrovirus, rhabdovirus, paramyxovirus or reovirus, or any species or strain within these larger groups. Viruses of the invention may be wild type (i.e. unaltered from the parental virus species), or with gene disruptions or gene additions. Which of these is the case will depend on the virus species to be used. Preferably the virus is a species of herpes virus, more preferably a strain of HSV, including strains of HSV1 and HSV2, and is most preferably a strain of HSV1. The virus of the invention is based on a clinical isolate of the virus species to be used. The clinical isolate is selected on the basis of it having particular advantageous properties for the treatment of cancer. The virus of the invention has surprisingly good anti-tumor effects compared to other strains of the same virus isolated from other patients, wherein a patient is an individual harbouring the virus species to be tested. The virus strains used for comparison to identify viruses of the invention may be isolated from a patient or an otherwise healthy (i.e. other than harboring the virus species to be tested) volunteer, preferably an otherwise healthy volunteer. HSV1 strains used to identify a virus of the invention are typically isolated from cold sores of individuals harboring HSV1, typically by taking a swab using e.g. Virocult (Sigma) brand swab/container containing transport media followed by transport to the facility to be used for further testing.

After isolation of viruses to be compared from individuals, stocks of the viruses are typically prepared, for example by growing the isolated viruses on BHK or vero cells. Preferably, this is done following no more than 3 cycles of freeze thaw between taking the sample and it being grown on, for example, BHK or vero cells to prepare the virus stock for further use. More preferably the virus sample has undergone 2 or less than 2 cycles of freeze thaw prior to preparation of the stock for further use, more preferably one cycle of freeze thaw, most preferably no cycles of freeze thaw. Lysates from the cell lines infected with the viruses prepared in this way after isolation are compared, typically by testing for the ability of the virus to kill tumor cell lines in vitro. Alternatively, the viral stocks may be stored under suitable conditions, for example by freezing, prior to testing. Viruses of the invention have surprisingly good anti-tumor effects compared to other strains of the same virus isolated from other individuals, preferably when compared to those isolated from >5 individuals, more preferably >10 other individuals, most preferably >20 other individuals.

The stocks of the clinical isolates identified as viruses of the invention (i.e. having surprisingly good properties for the killing of tumor cells as compared to other viral strains to which they were compared) may be stored under suitable conditions, before or after modification, and used to generate further stocks as appropriate.

A clinical isolate is a strain of a virus species which has been isolated from its natural host. The clinical isolate has preferably been isolated for the purposes of testing and comparing the clinical isolate with other clinical isolates of that virus species for a desired property, in the case of viruses of the invention that being the ability to kill human tumor cells. Clinical isolates which may be used for comparison also include those from clinical samples present in clinical repositories, i.e. previously collected for clinical diagnostic or other purposes. In either case the clinical isolates used for comparison and identification of viruses of the invention will preferably have undergone minimal culture in vitro prior to being tested for the desired property, preferably having only undergone sufficient culture to enable generation of sufficient stocks for comparative testing purposes. As such, the viruses used for comparison to identify viruses of the invention may also include deposited strains, wherein the deposited strain has been isolated from a patient, preferably an HSV1 strain isolated from the cold sore of a patient.

The virus of the invention is an oncolytic virus which is, or is derived from, a clinical isolate which has been selected by comparing the abilities of a panel of three or more clinical isolates of the same viral species to kill tumor cells of two or more tumor cell lines in vitro and selecting a clinical isolate which is capable of killing cells of two or more tumor cell lines more rapidly and/or at a lower dose in vitro than one or more of the other clinical isolates in the panel. Thus, the virus is a clinical isolate that kills two or more tumor cell lines more rapidly and/or at a lower dose in vitro than one or more reference clinical isolates of the same species of virus.

Typically, the clinical isolate of the invention will kill two or more tumor cell lines within 72 hours, preferably within 48 hours, more preferably within 24 hours, of infection at multiplicities of infection (MOI) of less than or equal to 0.1, preferably less than or equal to an MOI of 0.01 more preferably less than or equal to an MOI of 0.001. Preferably the clinical isolate will kill a broad range of human tumor cell lines, such as 2, 3, 4, 5, 6, 7 or all of the following cell lines: HT29 (colorectal), MDA-MB-231 (breast), SK-MEL-28 (melanoma), Fadu (squamous cell carcinoma), MCF7 (breast), A549 (lung), MIAPACA-2 (pancreas), HT1080 (fibrosarcoma). Thus, the virus of the invention may be capable of killing cells from two or more, such as 3, 4, 5, 6, 7 or more, different types of tumor such as two or more, such as 3, 4, 5, 6, 7 or more, solid tumors, including but not limited to colorectal tumor cells, prostate tumor cells, breast tumor cells, ovarian tumor cells, melanoma cells, squamous cell carcinoma cells, lung tumor cells, pancreatic tumor cells, sarcoma cells and/or fibrosarcoma cells.

Tumor cell line killing can be determined by any suitable method. Typically, a sample is first isolated from a patient, preferably, in the case of HSV1, from a cold sore, is used to infect BHK cells, or another suitable cell line such as vero cells. Positive samples are typically identified by the presence of a cytopathic effect (CPE) 24-72 hours post infection, such as 48 hours post infection, and confirmed to be the target viral species by, for example, immunohistochemistry or PCR. Viral stocks are then generated from the positive samples. A sample from the viral stock is typically tested and compared to other samples generated in the same way using swabs from different patients. Testing may be carried out by determining the level of CPE achieved at a range of multiplicity of infection (MOI) and at various times post infection.

For example, cell lines at 80% confluency may be infected with the viral sample at MOI of 1, 0.1, 0.01 and 0.001 and duplicate plates incubated for 24 and 48 hours at 37° C., 5% $CO_2$ prior to determination of the extent of viral cell killing. This may be determined by, for example, fixing the cells with glutaraldehyde and staining with crystal violet using standard methods. The level of cell lysis may then be assessed by standard methods such as gross observation, microscopy (cell counts) and photography. The method may be repeated with the cells being incubated for shorter time periods, such as 8, 12 or 16 hours, or longer time periods, such as 72 hours, before cell killing is determined, or at additional MOIs such as 0.0001 or less.

Growth curve experiments may also be conducted to assess the abilities of different clinical isolates to replicate in tumor cell lines in vitro. For example, cell lines at 80% confluency may be infected with the viral sample at MOI of 1, 0.1, 0.01 and 0.001 are incubated at 37° C., 5% $CO_2$ and the cells lysed, typically by freeze/thawing, at 0, 8, 16, 24 and 48 hours post infection prior to determination of the extent of viral cell killing. This may be determined by, for example, assessing viral titres by a standard plaque assay.

A clinical isolate of the invention can kill infected tumor cell lines more rapidly and/or at a lower MOI than the other clinical isolates to which it is compared, preferably 2, 3, 4, 5 or 10 or more, other clinical isolates of the same virus species. The clinical isolates of the invention typically kills a 10%, 25% or 50% greater proportion of the tumor cells present at a particular MOI and time point than at least one, preferably 2, 3, 4, 5 or 10 or more, other clinical isolates of the same virus type at the same MOI and time point to which it was compared. The clinical isolate of the invention typically kills the same or a greater proportion of tumor cells at a MOI that is half or less than half that of the MOI at which one or more, preferably 2, 3, 4, 5, 10 or 15 or more, other clinical isolates of the same virus species used for the comparison at the same time point, typically at 12, 24 and/or 48 hours, kills the same proportion of tumor cells. Preferably, a clinical isolate of the invention typically kills the same or a greater proportion of tumor cells at a MOI that is 5 or 10 times lower than the MOI at which one or more, preferably 2, 3, 4, 5, 10 or 15 or more, other clinical isolates of the same virus used for the comparison at the same time point, typically at 12, 24 and/or 48 hours kills the same proportion of tumor cells. The improved tumor cell killing abilities of a virus of the invention are typically achieved compared to at least 50%, 75% or 90% of the other clinical isolates of the same viral species used for the comparison. The virus is preferably compared to at least 4 other virus strains, such as, for example, 7, 9, 19, 39 or 49 other virus strains of the same species.

The isolated strains may be tested in batches, for example of 4-8 viral strains at a time, on, for example, 4-8 of the tumor cell lines at a time. For each batch of experiments, the degree of killing achieved is ranked on each cell line for the best (i.e. least surviving cells at each time point/MOI) to the worst (i.e. most surviving cells for each time point/MOI) for the viruses being compared in that experiment. The virus strains from each experiment which perform the best across the range of tumor cell line tested (i.e. that consistently ranked as one of the best at killing the cell lines) may then be compared head to head in further experiments using other clinical isolates and/ore other tumor cell lines to identify the best virus strains in the total of, for example, >20 virus strains sampled. Those ranked as the best overall are the viruses of the invention.

In a preferred embodiment, the virus of the invention is a strain selected from:
  strain RH018A having the provisional accession number ECCAC 16121904;
  strain RH004A having the provisional accession number ECCAC 16121902;
  strain RH031A having the provisional accession number ECCAC 16121907;
  strain RH040B having the provisional accession number ECCAC 16121908;
  strain RH015A having the provisional accession number ECCAC 16121903;
  strain RH021 A having the provisional accession number ECCAC 16121905;
  strain RH023A having the provisional accession number ECCAC 16121906; and
  strain RH047A having the provisional accession number ECCAC 16121909.

More preferably, the virus of the invention is a strain selected from:
  strain RH018A having the provisional accession number ECCAC 16121904;
  strain RH004A having the provisional accession number ECCAC 16121902;
  strain RH031 A having the provisional accession number ECCAC 16121907;
  strain RH040B having the provisional accession number ECCAC 16121908; and
  strain RH015A having the provisional accession number ECCAC 16121903;

Most preferably, the virus of the invention is strain RH018A having the accession number EACC 16121904.

An HSV of the invention is capable of replicating selectively in tumors, such as human tumors. Typically, the HSV replicates efficiently in target tumors but does not replicate efficiently in non-tumor tissue. This HSV comprises one or more mutations in one or more viral genes that inhibit replication in normal tissue but still allow replication in tumors. The mutation may, for example, be a mutation that prevents the expression of functional ICP34.5, ICP6 and/or thymidine kinase by the HSV.

In one preferred embodiment, the ICP34.5-encoding genes are mutated to confer selective oncolytic activity on the HSV. Mutations of the ICP34.5-encoding genes that prevent the expression of functional ICP34.5 are described in Chou et al. (1990) Science 250:1262-1266, Maclean et al. (1991) J. Gen. Virol. 72:631-639 and Liu et al. (2003) Gene Therapy 10:292-303, which are incorporated herein by reference. The ICP6-encoding gene and/or thymidine kinase-encoding gene may also be inactivated, as may other genes provided that such inactivation does not prevent the virus infecting or replicating in tumors.

The HSV may contain a further mutation or mutations which enhance replication of the HSV in tumors. The resulting enhancement of viral replication in tumors not only results in improved direct 'oncolytic' tumor cell killing by the virus, but also enhances the level of heterologous (i.e. a gene inserted into the virus, in the case of viruses of the invention genes encoding fusogenic protein(s) and an immune modulatory molecule(s)) gene expression and increases the amount of tumor antigen released as tumor cells die, both of which may also improve the immunogenic properties of the therapy for the treatment of cancer. For example, in a preferred embodiment of the invention, deletion of the ICP47-encoding gene in a manner that places the US11 gene under the control of the immediate early promoter that normally controls expression of the ICP47 encoding gene leads to enhanced replication in tumors (see Liu et al., 2003, which is incorporated herein by reference).

Other mutations that place the US11 coding sequence, which is an HSV late gene, under the control of a promoter that is not dependent on viral replication may also be introduced into a virus of the invention. Such mutations allow expression of US11 before HSV replication occurs and enhance viral replication in tumors. In particular, such mutations enhance replication of an HSV lacking functional ICP34.5-encoding genes.

Accordingly, in one embodiment the HSV of the invention comprises a US11 gene operably linked to a promoter, wherein the activity of the promoter is not dependent on viral replication. The promoter may be an immediate early (IE) promoter or a non-HSV promoter which is active in mammalian, preferably human, tumor cells. The promoter may, for example, be a eukaryotic promoter, such as a promoter derived from the genome of a mammal, preferably a human. The promoter may be a ubiquitous promoter (such as a promoter of β-actin or tubulin) or a cell-specific promoter, such as tumor-specific promoter. The promoter may be a viral promoter, such as the Moloney murine leukaemia virus long terminal repeat (MMLV LTR) promoter or the human or mouse cytomegalovirus (CMV) IE promoter. HSV immediate early (IE) promoters are well known in the art. The HSV IE promoter may be the promoter driving expression of ICP0, ICP4, ICP22, ICP27 or ICP47.

The genes referred to above may be rendered functionally inactive by any suitable method, for example by deletion or substitution of all or part of the gene and/or control sequence of the gene or by insertion of one or more nucleic acids into or in place of the gene and/or the control sequence of the gene. For example, homologous recombination methods, which are standard in the art, may be used to generate the virus of the invention.

As used herein, the term "gene" is intended to mean the nucleotide sequence encoding a protein, i.e. the coding sequence of the gene. The various genes referred to above may be rendered non-functional by mutating the gene itself or the control sequences flanking the gene, for example the promoter sequence. Deletions may remove one or more portions of the gene, the entire gene or the entire gene and all or some of the control sequences. For example, deletion of only one nucleotide within the gene may be made, resulting in a frame shift. However, a larger deletion may be made, for example at least about 25%, more preferably at least about 50% of the total coding and/or non-coding sequence. In one preferred embodiment, the gene being rendered functionally inactive is deleted. For example, the entire gene and optionally some of the flanking sequences may be removed from the virus. Where two or more copies of the gene are present in the viral genome both copies of the gene are rendered functionally inactive.

A gene may be inactivated by substituting other sequences, for example by substituting all or part of the endogenous gene with a heterologous gene and optionally a promoter sequence. Where no promoter sequence is substituted, the heterologous gene may be inserted such that it is controlled by the promoter of the gene being rendered non-functional. In an HSV of the invention it is preferred that the ICP34.5 encoding-genes are rendered non-functional by the insertion of a heterologous gene or genes and a promoter sequence or sequences operably linked thereto, and optionally other regulatory elements such as polyadenylation sequences, into each the ICP34.5-encoding gene loci.

A virus of the invention may be used to express a fusogenic protein and/or an immune stimulatory protein in tumors. This is typically achieved by inserting a heterologous gene encoding the fusogenic protein and/or a heterologous gene encoding the immune stimulatory protein in the genome of a selectively replication competent virus wherein each gene is under the control of a promoter sequence. As replication of such a virus will occur selectively in tumor tissue, expression of the fusogenic protein and/or immune stimulatory protein by the virus is also enhanced in tumor tissue as compared to non-tumor tissue in the body. Enhanced expression occurs where expression is greater in tumors as compared to other tissues of the body. Accordingly, the invention provides benefits of expression of both a fusogenic protein and/or an immune stimulatory protein selectively in tumors combined with the anti-tumor effect provided by oncolytic virus replication.

Fusogenic Protein

The virus of the invention may comprise a gene encoding a fusogenic protein. The fusogenic protein may be any heterologous protein capable of promoting fusion of a cell infected with the virus of the invention to another cell. A fusogenic protein, preferably a wild type or modified viral glycoprotein (i.e. modified to increase its fusogenic properties), is a protein which is capable in inducing the cell to cell fusion (syncitia formation) of cells in which it is expressed. Examples of fusogenic glycoproteins include VSV-G, syncitin-1 (from human endogenous retrovirus-W (HERV-W)) or syncitin-2 (from HERVFRDE1), paramyxovirus SV5-F, measles virus-H, measles virus-F, RSV-F, the glycoprotein from a retrovirus or lentivirus, such as gibbon ape leukemia virus (GALV), murine leukemia virus (MLV), Mason-Pfizer monkey virus (MPMV) and equine infectious anemia virus (EIAV) with the R transmembrane peptide removed (R-versions). In a preferred embodiment the fusogenic protein is from GALV and has the R-peptide removed (GALV-R-).

The virus of the invention may comprise multiple copies of the fusogenic protein-encoding gene, preferably 1 or 2 copies. The virus may comprise two or more different fusogenic proteins, including any of the fusogenic proteins listed above.

The fusogenic protein or proteins expressed by a virus of the invention may be identical to a naturally occurring protein, or may be a modified protein.

The fusogenic protein-encoding gene (fusogenic gene) may have a naturally occurring nucleic acid sequence or a modified sequence. The sequence of the fusogenic gene may, for example, be modified to increase the fusogenic properties of the encoded protein, or to provide codon optimisation and therefore increase the efficiency of expression of the encoded protein.

Immune Stimulatory Molecule

The virus of the invention may comprise one or more immune stimulatory molecules and/or one or more genes encoding an immune stimulatory molecule. Immune stimulatory molecules include proteins which may aid in the induction of an immune response, proteins which may relieve inhibitory signals to the induction or effectiveness of an immune response and RNA molecules (e.g. shRNA, antisense RNA, RNAi or micro RNA) which inhibit the expression of immune inhibitory molecules.

Examples of immune stimulatory molecules include IL-2, IL12, IL-15, IL-18, IL-21, IL-24, CD40 ligand, GITR ligand, 4-1-BB ligand, OX40 ligand, ICOS ligand, flt3 ligand, type I interferons, including interferon alpha and interferon beta, interferon gamma, type III interferon (IL-28, IL-29), other cytokines such as TNF alpha or GM-CSF, TGF beta or immune checkpoint antagonists. Immune checkpoint antagonists include antibodies, single chain antibodies and RNA1/siRNA/microRNA/antisense RNA knockdown approaches. Agonists of immune potentiating/co-stimulatory pathways include mutant or wild type, soluble, secreted and/or membrane bound ligands, and agonistic antibodies including single chain antibodies. With regard to the targeting of immune co-inhibitory or immune co-stimulatory pathways, proteins or other molecules (agonistic or antagonistic depending on the case) targeting CTLA-4 (antagonist). PD-1 (antagonist), PD-L1 (antagonist), LAG-3 (antagonist), TIM-3 (antagonist). VISTA (antagonist), CSF1R (antagonist), IDO (antagonist), CEACAM1 (antagonist). GITR (agonist), 4-1-BB (agonist), KIR (antagonist), SLAMF7 (antagonist), OX40 (agonist), CD40 (agonist), ICOS (agonist) or CD47 (antagonist) are particularly preferred. Viruses of the invention therefore preferably encode one or more of these molecules. More preferably viruses of the invention encode GM-CSF and/or a wild type or modified version of CD40L, ICOSL, 4-1-BBL, GITRL or OX40L, most preferably GM-CSF.

The inhibitor of a co-inhibitory pathway may be a CTLA-4 inhibitor. The CTLA-4 inhibitor is typically a molecule such as a peptide or protein that binds to CTLA-4 and reduces or blocks signaling through CTLA-4, such as by reducing activation by B7. By reducing CTLA-4 signalling, the inhibitor reduces or removes the block of immune stimulatory pathways by CTLA-4.

The CTLA-4 inhibitor is preferably an antibody or an antigen binding fragment thereof. The term "antibody" as referred to herein includes whole antibodies and any antigen binding fragment (i.e., "antigen-binding portion") or single chains thereof. An antibody refers to a glycoprotein comprising at least two heavy (H) chains and two light (kappa) (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The variable regions of the heavy and light chains contain a binding domain that interacts with an antigen. The VH and VL regions can be further subdivided into regions of hypervariability, termed complementarity determining regions (CDR), interspersed with regions that are more conserved, termed framework regions (FR). The constant regions of the antibodies may mediate the binding of the immunoglobulin to host tissues or factors, including various cells of the immune system (e.g., effector cells) and the first component (Clq) of the classical complement system.

The antibody is typically a monoclonal antibody. The antibody may be a chimeric antibody. The antibody is preferably a humanised antibody and is more preferably a human antibody.

The term "antigen-binding fragment" of an antibody refers to one or more fragments of an antibody that retain the ability to specifically bind to CTLA-4. The antigen-binding fragment also retains the ability to inhibit CTLA-4 and hence to reduce or remove the CTLA-4 blockade of a stimulatory immune response. Examples of suitable fragments include a Fab fragment, a F(ab')2 fragment, a Fab' fragment, a Fd fragment, a Fv fragment, a dAb fragment and an isolated complementarity determining region (CDR). Single chain antibodies such as scFv and heavy chain antibodies such as VHH and camel antibodies are also intended to be encompassed within the term "antigen-binding portion" of an antibody. In a preferred embodiment, the antibody is an scFv. Examples of suitable scFv molecules are disclosed in, for example, WO2007/123737 and WO2014/066532, which are incorporated herein by reference. The scFv may be encoded by the nucleotide sequence shown in SEQ ID NO: 34 the nucleotide sequence shown in SEQ ID NO: 35.

Viruses of the invention may encode one or more immune stimulatory molecules, preferably 1, 2, 3 or 4 immune stimulatory molecules, more preferably 1 or 2 immune stimulatory molecules.

The sequence of the gene encoding the immune stimulatory molecule may be codon optimized so as to increase expression levels of the respective proteins in target cells as compared to if the unaltered sequence is used.

Modification of Virus Strains

Modified viruses of the invention are modified versions of such clinical isolates identified as having advantageous properties for killing tumor cells as compared to other virus strains used for the comparison. Modified viruses of the invention are constructed using methods well known in the art. For example plasmids (for smaller viruses and single and multiple genome component RNA viruses) or BACS (for larger DNA viruses including herpes viruses) encoding the viral genome to be packaged, including any genes encoding fusogenic and/or immune stimulating molecules under appropriate regulatory control, can be constructed by standard molecular biology techniques and transfected into permissive cells from which recombinant viruses can be recovered.

Alternatively, in a preferred embodiment plasmids containing DNA regions flanking the intended site of insertion can be constructed, and then co-transfected into permissive cells with viral genomic DNA such that homologous recombination between the target insertion site flanking regions in the plasmid and the same regions in the parental clinical isolate occur. Recombinant viruses can then be selected and purified through the loss or addition of a function inserted or deleted by the plasmid used for modification, e.g. insertion or deletion of a marker gene such as GFP or lacZ from the parental virus at the intended insertion site. In a most preferred embodiment the insertion site is the ICP34.5 locus of HSV, and therefore the plasmid used for manipulation contains HSV sequences flanking this insertion site, between which are an expression cassette encoding a fusogenic protein and an immune stimulatory molecule. In this case, the parental clinical isolate may contain a cassette encoding GFP in place of ICP34.5 and recombinant virus plaques are selected through the loss of expression of GFP. In a most preferred embodiment the US11 gene of HSV is also expressed as an IE gene. This may be accomplished through deletion of the ICP47-encoding region, or by other means.

Fusogenic protein encoding sequences and immune stimulatory molecule encoding sequences may be inserted into the viral genome under appropriate regulatory control. This may be under the regulatory control of natural promoters of the virus species of the invention used, depending on the species and insertion site, or preferably under the control of heterologous promoters. Suitable heterologous promoters include mammalian promoters, such as the IEF2a promoter or the actin promoter. More preferred are strong viral promoters such as the CMV IE promoter, the RSV LTR, the MMLV LTR or promoters derived from SV40. Preferably each exogenous gene (i.e. encoding the fusogenic protein and immune modulatory molecule) will be under separate promoter control, but may also be expressed from a single RNA transcript, for example through insertion of an internal ribosome entry sites (IRES) between protein coding sequences. RNA derived from each promoter is typically terminated using a polyadenylation sequence (e.g. mammalian sequences such as the bovine growth hormone (BGH) poly A sequence, synthetic polyadenylation sequences, or viral sequences such as the SV40 early or late polyadenylation sequence).

The invention also provides a virus, such as a pox virus or a HSV, preferably HSV1, which expresses at least three heterologous genes, wherein each of the three heterologous genes is driven by a different promoter selected from the CMV promoter, the RSV promoter, the EF1a promoter, the SV40 promoter and a retroviral LTR promoter. The virus may, for example, express four heterologous genes, wherein each of the four heterologous genes is driven by a different promoter selected from the CMV promoter, the RSV promoter, the EF1a promoter, the SV40 promoter and a retroviral LTR promoter. The retroviral LTR is preferably from MMLV (SEQ ID NO:43), also known as MoMuLV. The heterologous genes may be terminated by poly adenylation sequences. The poly adenylation sequences may be the same or different. Preferably each heterologous gene is terminated by a different poly adenylation sequence, which is preferably selected from the BGH, SV40, HGH and RBG poly adenylation sequences.

The invention also provides a virus, such as a pox virus or a HSV, preferably HSV1, which expresses at least three heterologous genes, wherein each of the three heterologous genes is terminated by a different poly adenylation sequence selected from the BGH, SV40, HGH and RBG poly adenylation sequences. The virus may, for example, express four heterologous genes terminated by each of the BGH, SV40, HGH and RBG poly adenylation sequences, respectively.

Pharmaceutical Compositions

The invention provides a pharmaceutical composition comprising a virus of the invention and a pharmaceutically acceptable carrier or diluent. Suitable carriers and diluents include isotonic saline solutions, for example phosphate-buffered saline. The composition may further comprise other constituents such as sugars or proteins to improve properties such as stability of the product. Alternatively a lyophilized formulation may be used, which is reconstituted in a pharmaceutically acceptable carrier or diluent before use.

The choice of carrier, if required, is frequently a function of the route of delivery of the composition. Within this invention, compositions may be formulated for any suitable route and means of administration. Pharmaceutically acceptable carriers or diluents are those used in compositions suitable for intra-tumoral administration, intravenous/intraarterial administration, administration into the brain or administration into a body cavity (e.g. bladder, pleural cavity or by intraperitoneal administration). The composition may be administered in any suitable form, preferably as a liquid.

The present invention also provides a product of manufacture comprising a virus of the invention in a sterile vial, ampoule or syringe.

Medical Uses/Methods of Treatment

The invention provides the virus of the invention for use in the treatment of the human or animal body by therapy, particularly for use in a method of treating cancer. The cancer is typically in a mammal, preferably in a human. The virus kills infected tumour cells by virus mediated toxicity, including by lysis, necrosis or apoptosis, preferably by lysis or necrosis. The virus of the invention also elicits a systemic anti-tumor immune response, augmented through the expression of the immune stimulatory molecule, which also kills cancer cells.

The invention also provides a method of treating cancer, the method comprising administering a therapeutically effective amount of the virus of the invention to an individual in need thereof.

The invention additionally provides the use of the virus of the invention in the manufacture of a medicament for treating cancer.

The virus of the invention is particularly useful in treating any solid tumor including any adenocarcinoma, carcinoma or sarcoma. For example, the virus of the invention is useful in treating head and neck, prostate, breast, ovarian, lung, liver, endometrial, bladder, gall bladder, pancreas, colon, kidney, stomach/gastric, esophageal, or cervical cancers, mesothelioma, melanoma or other skin cancer, lymphoma, glioma or other cancer of the nervous system, or sarcomas such as soft tissue sarcoma.

The virus of the invention may be used to treat malignant tumors, including tumors that have metastasised from the site of the original tumor. In this embodiment, the virus may be administered to the primary tumor or to one or more secondary tumors.

The virus of the invention may be administered in combination with other therapeutic agents, including chemotherapy, targeted therapy, immunotherapy (including immune co-inhibitory pathway blockade or immune co-stimulatory pathway activation) and/or in combination with radiotherapy and/or in combination with any combination of these. The therapeutic agent is preferably an anti-cancer agent.

The virus of the invention may be administered in combination with a second virus, such as a second oncolytic virus.

For example, the therapeutic agent may comprise an immunogen (including a recombinant or naturally occurring antigen, including such an antigen or combination of antigens delivered as DNA or RNA in which it/they are encoded), to further stimulate an immune response, such as a cellular or humoral immune response, to tumor cells, particularly tumor neoantigens. The therapeutic agent may be an agent intended to increase or potentiate an immune response, such as a cytokine, an agent intended to inhibit an immune checkpoint pathway or stimulate an immune potentiating pathway or an agent which inhibits the activity of regulatory T cells (Tregs).

The therapeutic agent may be an agent known for use in an existing cancer therapeutic treatment. The therapeutic agent may be radiotherapy or a chemotherapeutic agent. The therapeutic agent may be selected from cyclophosmamide, alkylating-like agents such as cisplatin or melphalan, plant alkaloids and terpenoids such as vincristine or paclitaxel (Taxol), antimetabolites such as 5-fluorouracil, topoisomerase inhibitors type I or II such as camptothecin or doxorubicin, cytotoxic antibiotics such as actinomycin, anthracyclines such as epirubicin, glucocorticoids such as triamcinolone, inhibitors of protein, DNA and/or RNA synthesis such as methotrexate and dacarbaxine, histone deacetylase (HDAC) inhibitors, or any other chemotherapy agent.

The therapeutic agent may be one, or a combination of: immunotherapeutics or immunomodulators, such as TLR agonists; agents that down-regulate T-regulatory cells such as cyclophosphamide; or agents designed to block immune checkpoints or stimulate immune potentiating pathways, including but not limited to monoclonal antibodies, such as a CTLA-4 inhibitor, a PD-1 inhibitor, a PD-L1 inhibitor, a LAG-3 inhibitor, a TIM-3 inhibitor, a VISTA inhibitor, a CSF1R inhibitor, an IDO inhibitor, a CEACAM1 inhibitor, a GITR agonist, a 4-1-BB agonist, a KIR inhibitor, a SLAMF7 inhibitor, an OX40 agonist, a CD40 agonist, an ICOS agonist or a CD47 inhibitor. In a preferred embodiment, the therapeutic agent is a CTLA-4 inhibitor such as an anti-CTLA-4 antibody, a PD1 inhibitor, such as an anti-PD-1 antibody or a PD-L1 inhibitor such as an anti-PD-L1 antibody. Such inhibitors, agonists and antibodies can be generated and tested by standard methods known in the art.

Immunotherapeutic agents may also include bi-specific antibodies, cell based-therapies based on dendritic cells, NK cells or engineered T cells such CAR-T cells or T cells expressing engineered T cell receptors. Immunotherapeutic agents also include agents that target a specific genetic mutation which occurs in tumors, agents intended to induce immune responses to specific tumor antigens or combinations of tumor antigens, including neoantigens and/or agents intended to activate the STING/cGAS pathway, TLR or other innate immune response and/or inflammatory pathway, including intra-tumoral agents.

For example, a virus of the invention may be used: in combination with dacarbazine, a BRAF inhibitor and or CTLA-4, PD1 or PD-L1 blockade to treat melanoma; in combination with taxol, doxorubicin, vinorelbine, cyclophosphamide and/or gemcitabine to treat breast cancer; in combination with 5-fluorouracil and optionally leucovorin, irinoteacan and/or oxaliplatin to treat colorectal cancer; in combination with taxol, carboplatin, vinorelbine and/or gemcitabine, PD-1 or PD-L1 blockade to treat lung cancer; in combination with cisplatin and/or radiotherapy to treat head and neck cancer.

The therapeutic agent may be an inhibitor of the idoleamine 2,3-dioxygenase (IDO) pathway. Examples of IDO inhibitors include epacadostat (INCB024360), 1-methyl-tryptophan, indoximod (1-methyl-D-tryptophan), GDC-0919 or F001287.

The mechanism of action of IDO in suppressing anti-tumor immune responses may also suppress immune responses generated following oncolytic virus therapy. IDO expression is induced by toll like receptor (TLR) activation and interferon-7 both of which may result from oncolytic virus infection. One embodiment of the use of oncolytic virus therapy for cancer treatment includes combination of an oncolytic virus, including a virus expressing an immune stimulating protein or proteins and/or a fusogenic protein, with an inhibitor of the IDO pathway and optionally one or more further antagonist of an immune co-inhibitory pathway and/or one or more agonist of an immune co-stimulatory pathway, including those targeting CTLA-4, PD-1 and/or PD-L1.

The invention also provides a method of treating cancer, which comprises administering a therapeutically effective amount of an oncolytic virus, an inhibitor of the indoleamine 2,3-dioxygenase (IDO) pathway and a further antagonist of an immune co-inhibitory pathway, and/or an agonist of an immune co-stimulatory pathway to a patient in need thereof.

The oncolytic virus is preferably a modified clinical isolate. The oncolytic virus is preferably a pox virus, more preferably a HSV, such as a HSV1 and/or a HSV rendered functionally inactive for ICP34.5 and/or ICP47. The oncolytic virus may express an immune stimulating molecule, such as GM-CSF, and/or a fusogenic protein, such as the GALV fusogenic glycoprotein with the R sequence mutated or deleted. The further antagonist of an immune co-inhibitory pathway is preferably an antagonist of CTLA-4, an antagonist of PD1 or an antagonist of PD-L1. For example, the further antagonist of an immune co-inhibitory pathway may be an inhibitor of the interaction between PD1 and PD-L1.

Where a therapeutic agent and/or radiotherapy is used in conjunction with a virus of the invention, administration of the virus and the therapeutic agent and/or radiotherapy may be contemporaneous or separated by time. The composition of the invention may be administered before, together with or after the therapeutic agent or radiotherapy. The method of treating cancer may comprise multiple administrations of the virus of the invention and/or of the therapeutic agent and/or radiotherapy. A skilled practitioner will readily be able to determine suitable courses of administration of the virus and the therapeutic agent.

In preferred embodiments, in the case of combination with one or more antagonist of an immune co-inhibitory pathway, one or more agonist of an immune co-stimulatory pathway and/or other immune potentiating agents, the virus of the invention is administered once or multiple times prior to the concurrent administration of the antagonist of an immune co-inhibitory pathway, agonist of an immune co-stimulatory pathway and/or other immune potentiating agent or agents thereafter, or concurrent with the administration of the antagonist of an immune co-inhibitory pathway, agonist of an immune co-stimulatory pathway and/or other immune potentiating agent or agents without prior administration of the virus of the invention.

The virus of the invention may be administered to a subject by any suitable route. Typically, a virus of the invention is administered by direct intra-tumoral injection, including through the use of imaging guidance to target the tumor or tumors. The virus may be administered into a body cavity, for example into the pleural cavity, bladder or by intra-peritoneal administration. The virus may be injected into a blood vessel, preferably a blood vessel supplying a tumor.

Therapeutic agents which may be combined with a virus of the invention can be administered to a human or animal subject in vivo using a variety of known routes and techniques. For example, the composition may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The composition may be administered topically to skin or mucosal tissue, such as nasally, intratracheally, intestinally, sublingually, rectally or vaginally, or provided as a finely divided spray suitable for respiratory or pulmonary administration. In preferred embodiments, the compositions are administered by intravenous infusion, orally, or directly into a tumor.

The virus and/or therapeutic agent may be administered to a subject in an amount that is compatible with the dosage composition that will be therapeutically effective. The administration of the virus of the invention is for a "therapeutic" purpose. As used herein, the term "therapeutic" or "treatment" includes any one or more of the following as its objective: the prevention of any metastasis or further metastasis occurring; the reduction or elimination of symptoms; the reduction or complete elimination of a tumor or cancer, an increase in the time to progression of the patient's cancer; an increase in time to relapse following treatment; or an increase in survival time.

Therapeutic treatment may be given to Stage I, II, III, or IV cancers, preferably Stage II, III or IV, more preferably Stage III or IV, pre- or post-surgical intervention, preferably before surgical intervention (either for resection of primary or recurrent/metastatic disease), i.e. while residual tumor remains.

Therapeutic treatment may be carried out following direct injection of the virus composition into target tissue which may be the tumor, into a body cavity, or a blood vessel. As a guide, the amount of virus administered is in the case of HSV in the range of from $10^4$ to $10^{10}$ pfu, preferably from $10^5$ to $10^9$ pfu. In the case of HSV, an initial lower dose (e.g. $10^4$ to $10^7$ pfu) may be given to patients to seroconvert patients who are seronegative for HSV and boost immunity in those who are seropositive, followed by a higher dose then being given thereafter (e.g. $10^6$ to $10^9$ pfu). Typically up to 20 ml of a pharmaceutical composition consisting essentially of the virus and a pharmaceutically acceptable suitable carrier or diluent may be used for direct injection into tumors, or up to 50 ml for administration into a body cavity (which may be subject to further dilution into an appropriate diluent before administration) or into the bloodstream. However for some oncolytic therapy applications larger or smaller volumes may also be used, depending on the tumor and the administration route and site.

The routes of administration and dosages described are intended only as a guide since a skilled practitioner will be able to determine readily the optimum route of administration and dosage. The dosage may be determined according to various parameters, especially according to the location of the tumor, the size of the tumor, the age, weight and condition of the patient to be treated and the route of administration. Preferably the virus is administered by direct injection into the tumor. The virus may also be administered by injection into a blood vessel or into a body cavity. The optimum route of administration will depend on the location and size of the tumor. Multiple doses may be required to achieve an immunological or clinical effect, which, if required, will be typically administered between 2 days to 12 weeks apart, preferably 3-days to 3 weeks apart. Repeat doses up to 5 years or more may be given, preferably for up to one month to two years dependent on the speed of response of the tumor type being treated and the response of a particular patient, and any combination therapy which may also be being given.

The following Examples illustrate the invention.

Example 1. Clinical Isolates with Improved Anti-Tumor Effects

The virus species used to exemplify the invention is HSV, specifically HSV1. Cold sore swabs were taken from more than 20 otherwise healthy volunteers. A sample of each swab was used to infect BHK cells. Samples containing HSV1 were identified by the presence of a cytopathic effect (CPE) 24-72 hours post infection and by immunohistochemistry and viral stocks of the primary clinical isolates were generated from the positive samples.

The abilities of the primary clinical isolates of HSV1 to kill a panel of human tumor-derived cell lines is tested and the virus strain with the greatest ability to kill a broad range of these rapidly, and at low dose is chosen. Tumor cell lines used for this comparison are HT29 (colorectal), MDA-MB-231 (breast), SK-MEL-28 (melanoma), Fadu (squamous cell carcinoma), MCF7 (breast), A549 (lung), MIAPACA-2 (pancreas), CAPAN-1 (pancreas), HT1080 (fibrosarcoma). The cell lines are used to test for the level of CPE achieved at a range of MOI and times post infection for each of the primary clinical isolates.

More specifically, the tumor cell lines are used to seed multi-well tissue culture plates so that they are about 80% confluent on the day of infection. Representative wells from each tumor cell line are trypsinised and the number of cells in the well determined. These cell counts are used to determine the volume of each clinical isolate required to give an MOI of 1, 0.1, 0.01 and 0.001. Separate wells of a tumor cell line are infected with the clinical isolate at these MOI and overlaid with growth media and carboxymethyl-cellulose. All infections are carried out in quadruplicate. Duplicate wells are incubated for 24 hours and duplicate wells are incubated for 48 hours, both at 37° C., 5% $CO_2$, prior to fixation of the cells with glutaraldehyde and staining with crystal violet. The level of cell lysis is then assessed by gross observation, microscopy (cell counts) and photography or using a metabolic assay such as an MTT assay.

Growth curve experiments are also conducted to assess the abilities of different clinical isolates to replicate in tumor cell lines in vitro. The tumor cell lines are used to seed multi-well tissue culture plates so that they are about 80% confluent on the day of infection. Cell counts are determined as above and used to determine the volume of virus to give MOIs of 1, 0.1, 0.01 and 0.001. The tumor cells are infected in duplicate for MOI and time point. The infected cells are incubated at 37° C., 5% $CO_2$ and the cells lysed by freeze/thawing at 0, 8, 16, 24 and 48 hours post infection. Viral titres are assessed by a standard plaque assay.

Example 2. Modification of Clinical Isolates

In this example the clinical isolate selected in Example 1 (i.e. a virus if the invention) is modified by deletion of ICP47 from the viral genome using homologous recombination with a plasmid containing regions flanking HSV1 nucleotides 145300 to 145582 (HSV1 nucleotides 145300 to 145582 being the sequences to be deleted; HSV1 strain 17 sequence Genbank file NC 001806.2) between which are encoded GFP. GFP expressing virus plaques are selected, and GFP then removed by homologous recombination with the empty flanking regions and plaques which do not express GFP are selected. This results in an ICP47 deleted virus in which US11 is expressed as an IE protein as it is now under the control of the ICP47 promoter. ICP34.5 is then deleted using homologous recombination with a plasmid containing regions flanking HSV1 nucleotides 124953 to 125727 (HSV1 nucleotides 124953 to 125727 being the sequences to be deleted; HSV1 strain 17 sequence Genbank file NC 001806.2) between which GFP is encoded. GFP expressing virus plaques are again selected, and GFP then removed by homologous recombination with the same flanking regions but between which are now an expression cassette comprising a codon optimized version of the mouse GM-CSF sequence and a codon optimized version of the GALV R- sequence driven by the CMV IE promoter and RSV promoter respectively, in a back to back orientation and again selecting virus plaques which do not express GFP. This virus construction is performed using methods which are standard in the art.

The structure of the resulting virus is shown in FIG. 1 (top panel). The mGM-CSF and GALV-R- sequences are shown in SEQ ID NOs 2 and 8 respectively. The structure of the resulting virus is confirmed by restriction digestion and Southern blot, GM-CSF expression is confirmed by ELISA, and GALV-R- expression is confirmed by infection of human HT1080 tumor cells and the observation of syncitial plaques.

Viruses are also constructed using similar procedures which have no insertion into ICP34.5, or which only have inserted the gene for mouse GM-CSF or GALV-R-. The structures of these viruses are also shown in FIG. 1.

For human use, hGM-CSF is used, the sequence for a codon optimised version of which is shown in SEQ ID NO 4.

Example 3. Expression of Two Immune Stimulatory Molecule from a Virus Expressing a Fusogenic Protein A virus similar to the GALV-R- and mGM-CSF expressing virus described above is constructed, but additionally expressing versions of CD40L. Here, instead of using a plasmid containing ICP34.5 flanking regions and an expression cassette comprising GM-CSF and GALV-R- driven by a CMV and an RSV promoter, a plasmid containing ICP34.5 flanking regions and an expression cassette comprising GM-CSF. GALV and CD40L driven by a CMV, an RSV and an SV40 promoter is used for recombination with the virus containing GFP inserted into ICP34.5 and non-GFP expressing plaques again selected.

Example 4. The Effect of the Combined Expression of a Fusogenic Protein and an Immune Stimulatory Molecule from an Oncolytic Virus in Mouse Tumor Models The GALV R- protein causes cell to cell fusion in human cells but not in mouse cells because the PiT-1 receptor required for cell fusion to occur has a sequence in mice which does not allow cell fusion to occur. As a result mouse tumor cells expressing human PiT-1 are first prepared using methods standard in the art. Human PiT-1 is cloned into a lentiviral vector also comprising a selectable marker gene. The vector is transfected into target CT26 mouse colorectal cancer tumor cells and clones resistant to the selectable marker are selected to generate CT26/PiT-1 cells. PiT-1 expression is confirmed by western blotting in untransfected cells and in cells transfected with the PiT-1 expressing lentivirus and by transfection of a plasmid expressing GALV-R- and confirmation that cell fusion occurs.

The utility of the invention is demonstrated by administering CT26/PiT-1 cells into both flanks of Balb/c mice and allowing the CT26/PiT-1 tumors to grow to approximately 0.5 cm in diameter.

The following treatments are then administered to groups of mice (five per group), into one flank of each mouse only 3 times per week for two weeks:
  50 µl of saline (1 group);
  50 µl of $10^5$ pfu/ml, $10^6$ pfu, or $10^7$ pfu/ml of the HSV with no inserted gene (3 groups);
  50 µl of $10^5$ pfu/ml, $10^6$ pfu/ml, or $10^7$ pfu/ml of the HSV with only mouse GM-CSF inserted (3 groups);
  50 µl of $10^5$ pfu/ml, $10^6$ pfu/ml, or $10^7$ pfu/ml of the virus with only GALV-R-inserted (3 groups); or 50p of 105 pfu/ml, 106 pfu/ml, or 107 pfu/ml of the virus with both mouse GM-CSF and GALV-R- inserted (3 groups).

Effects on tumor growth are then observed for up to one month. Superior tumor control and shrinkage in both injected and uninjected tumors with the virus expressing GM-CSF and GALV-R- as compared to the other groups is observed, including through an improved dose response curve.

Example 5. The Effect of Combined Expression of a Fusogenic Protein and an Immune Stimulatory Molecule from an Oncolytic Virus on the Therapeutic Effect of Immune Checkpoint Blockade in Mouse Tumor Models The experiment in Example 3 above is repeated but mice are additionally dosed bi-weekly by the intra-peritoneal route with an antibody targeting mouse PD-1 (10 mg/kg; Bioxcell RMP-1-14 on the same days as virus dosing) or an antibody targeting mouse CTLA-4 (10 mg/kg; Bioxcell 9H10 on the same days as virus dosing). An additional group of mice is added which receive no antibody treatment. More specifically, groups of mice receive (1) saline. (2) HSV with no inserted gene. (3) HSV with both GM-CSF and GALV-R-inserted as in Example 3. (4) PD-1 antibody. (5) CTLA-4 antibody. (6) HSV with no inserted gene plus PD-1 antibody. (7) HSV with no inserted gene plus CTLA-4 antibody. (8) HSV with GM-CSF and GALV-R- and PD-1 antibody or (9) HSV with GM-CSF and GALV-R- and CTLA-4 antibody. Superior tumor control and shrinkage in both injected and uninjected tumors with the virus expressing GM-CSF and GALV-R- together with the anti-PD-1 antibody or the anti-CTLA-4 antibody as compared to the other groups is observed, including through an improved dose response curve.

Example 6. Collection of Clinical Isolates

The virus species used to exemplify the invention is HSV, specifically HSV1. To exemplify the invention, 181 volunteers were recruited who suffered from recurrent cold sores. These volunteers were given sample collection kits (including Sigma Virovult collection tubes), and used these to swab cold sores when they appeared following which these samples were shipped to Replimune. Oxford UK. From June 2015-February 2016, swabs were received from 72 volunteers. A sample of each swab was used to infect BHK cells. Of these 36 live virus samples were recovered following plating out and growth on BHK cells. These samples are detailed in Table 1.

TABLE 1

Details of Tested Swab Samples & Result

| Sample Number | Virus retrieved |
| --- | --- |
| RH001A | No |
| RH001B | |
| RH002A | Yes |
| RH003A | No |
| RH004A | Yes |
| RH004B | |
| RH005A | No |
| RH005B | |
| RH006A | No |
| RH006B | |

TABLE 1-continued

Details of Tested Swab Samples & Result

| Sample Number | Virus retrieved |
| --- | --- |
| RH007A | Yes |
| RH007B | |
| RH007C | |
| RH008A | No |
| RH008B | |
| RH008C | |
| RH009A | No |
| RH009B | |
| RH010A | No |
| RH011A | No |
| RH011B | |
| RH011C | |
| RH012A | No |
| RH013A | No |
| RH014A | Yes |
| RH014B | |
| RH015A | Yes |
| RH016A | No |
| RH016B | |
| RH017A | Yes |
| RH018A | Yes |
| RH018B | |
| RH018C | |
| RH019A | No |
| RH019B | |
| RH019C | |
| RH020A | Yes- RH020A only |
| RH020B | |
| RH020C | |
| RH021A | Yes |
| RH021B | |
| RH022A | Yes |
| RH022B | |
| RH023A | Yes |
| RH024A | No |
| RH025A | Yes -RH025B only |
| RH025B | |
| RH026A | Yes |
| RH027A | No |
| RH027B | |
| RH027C | |
| RH028A | No |
| RH028B | |
| RH028C | |
| RH029A | No |
| RH030A | No |
| RH031A | Yes - RH031A to RH031D |
| RH031B | |
| RH031C | |
| RH031D | |
| RH031E | |
| RH031F | |
| RH032A | No |
| RH033A | No |
| RH033B | |
| RH033C | |
| RH034A | No |
| RH034B | |
| RH034C | |
| RH035A | No |
| RH036A | Yes |
| RH037A | Yes |
| RH038A | Yes |
| RH039A | No |
| RH039B | |
| RH039C | |
| RH040A | Yes |
| RH040B | |
| RH040C | |
| RH041A | Yes |
| RH042A | Yes |
| RH043A | No |
| RH043B | |
| RH043C | |
| RH044A | No |
| RH045A | No |

TABLE 1-continued

Details of Tested Swab Samples & Result

| Sample Number | Virus retrieved |
|---|---|
| RH046A | Yes |
| RH047A | Yes- RH047A and |
| RH047B | RH047C |
| RH047C | |
| RH048A | No |
| RH049A | No |
| RH049B | |
| RH049C | |
| RH050A | No |
| RH051A | Yes |
| RH051B | |
| RH052A | Yes - RH052A only |
| RH052B | |
| RH053A | No |
| RH054A | No |
| RH055A | No |
| RH055B | |
| RH056A | Yes |
| RH057A | No |
| RH058A | Yes |
| RH058B | |
| RH059A | No |
| RH060A | No |
| RH061A | Yes |
| RH062A | No |
| RH063A | No |
| RH064A | Yes |
| RH065A | Yes |
| RH065B | |
| RH066A | No |
| RH067A | No |
| RH067B | |
| RH068A | No - contaminated |
| RH069A | No |
| RH069A | |
| RH070A | Yes |
| RH071A | Yes |
| RH072A | No |
| RH073A | Yes |
| RH073B | |
| RH074A | No |
| RH074B | |
| RH075A | No |
| RH076A | No |
| RH078A | No |
| RH078B | |
| RH079B | Yes |
| RH079B | |
| RH080A | No |
| RH081A | Yes |
| RH082A | No |
| RH082B | |
| RH083A | Yes |
| RH083B | |
| RH084A | Yes |
| RH084B | |
| RH084C | |
| RH085A | No |
| RH086A | No |
| RH087A | Yes - RH078B only |
| RH087B | |

Designations A, B, C etc. indicate multiple swabs from the same volunteer.

Example 7. Identification of Clinical Isolates with Improved Anti-Tumor Effects The abilities of the primary clinical isolates of HSV11 to kill a panel of human tumor-derived cell lines was tested. The tumor cell lines used for this comparison were HT29 (colorectal), MDA-MB-231 (breast), SK-MEL-28 (melanoma), Fadu (squamous cell carcinoma), MCF7 (breast), A549 (lung), MIAPACA-2 (pancreas) and HT1080 (fibrosarcoma). The cell lines were used to test for the level of CPE achieved at a range of MOI and times post infection for each of the primary clinical isolates.

Experiments were conducted in parallel using 5 to 8 of the new viruses strains at the same time. The virus strains were plated out in duplicate at a range of MOIs (0.001-1), and the extent of CPE following crystal violet staining was assessed at 24 and 48 hours following infection. The viral strains which were most effective at killing the tumor cell lines were scored, and the most effective two or three strains from each screen of 5-8 strains were identified and compared in parallel in a further experiment to identify the top strains for further development.

The initial screens demonstrated substantial variability in the ability of the different strains to kill the different tumor cell lines. Of an initial 29 strains tested, 8 strains of interest were identified in the initial screens for further comparison. These were strains RH004A, RH015A, RH018A, RH021A, RH023A, RH31A, RH040A, and RH047A.

Figure 3:
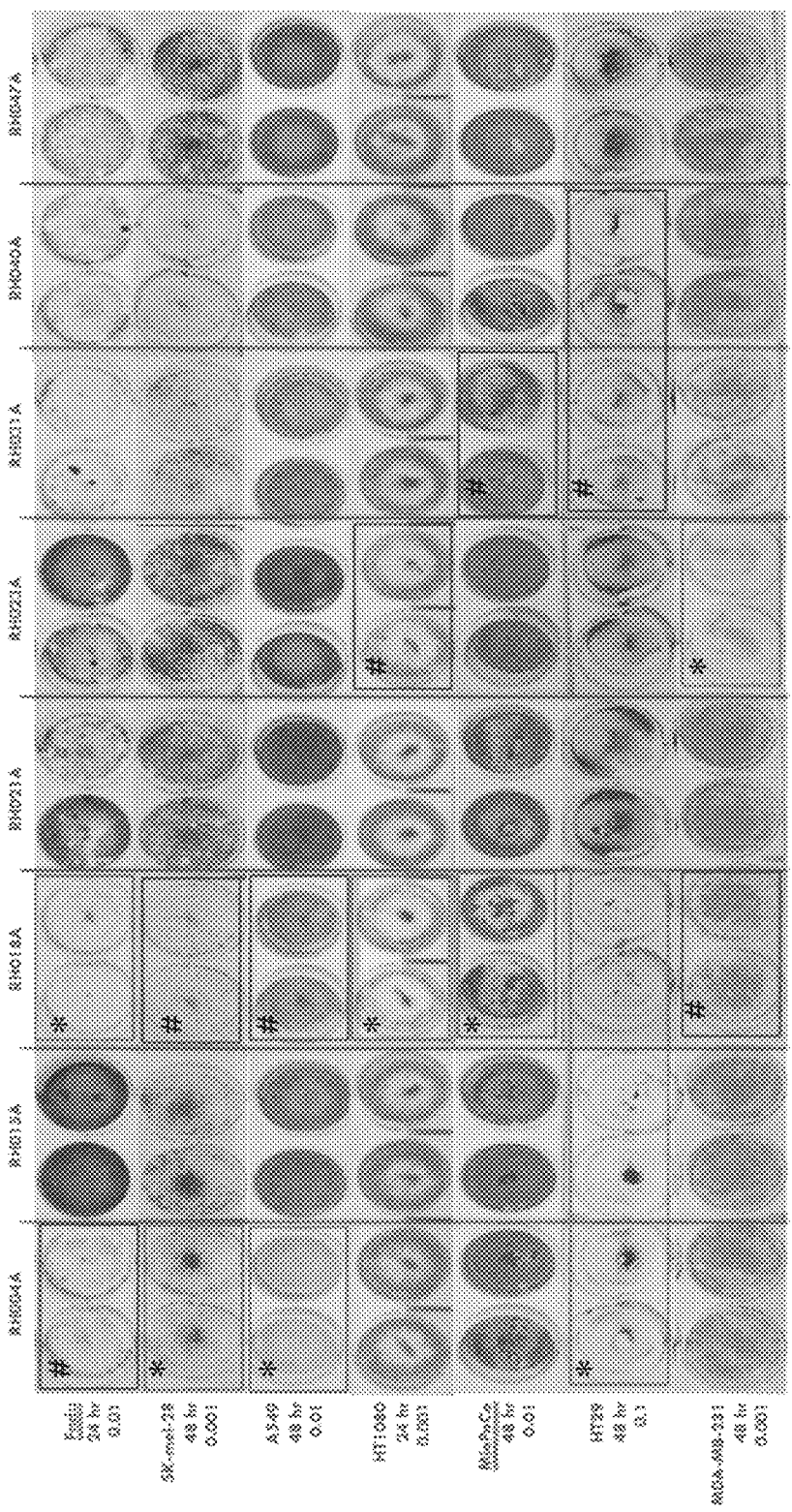
FIG. 3 shows the differential abilities of the eight top ranking HSV1 clinical isolate strains as assessed by crystal violet staining 24 hours or 48 hours after infection with a MOI of 0.1, 0.01 or 0.001 as indicated in the Figure to kill Fadu. SK-mel-28, A549, HT1080. MIA-PA-CA-2. HT29 and MDA-MB-231 human tumor cell lines. The virus strains ranked first and second on each cell line are indicated. The virus RH018A was ranked first on each of the Fadu, HT1080, MIA-PA-CA-2 and HT29 cell lines and second on each of the SK-mel-28. A549 and MDA-MB-231 cell lines. RH004A was ranked joint first with RH018A and RH015A on the HT29 cell line, first on the SK-mel-28 and A549 cell lines and second on the Fadu cell line. RH023A was ranked first on the MDA-MB-231 cell line and second on the HT1080 cell line. RH031A was ranked second on each of the MIA-PA-CA-2 and HT29 cell lines. RH040A was ranked joint second on the HT29 cell line.

The 8 strains for further comparison were tested in parallel on the panel of tumor cell lines, and their relative ability to kill these tumor cell lines was assessed following crystal violet staining and observation for CPE. FIG. 3 shows a representative time point and MOI for these viruses on each of the viruses on each of the cell lines demonstrating the differential ability of the viruses to kill the target tumor cell lines observed.

There was substantial variation amongst the strains, and it was found that while a particular strain may be particularly effective at killing one cell line, it is not necessarily particularly effective at killing other cell lines too, further demonstrating the degree of variability in the ability of clinical strains of HSV to kill tumor cells of different types.

FIG. 3 also indicates which of the virus strains was both best and second best at killing each of the cell lines, enabling the virus strains to be rank ordered as to their overall relative ability to kill the panel of cell lines as a whole. This analysis demonstrated that strains RH004A, RH015A. RH018A, RH031A and RH040A were relatively more effective than the other strains, and these five strains were chosen for potential further development as oncolytic agents. Of these top five strains, the relative rank order based on their abilities to kill across the panel of cell lines was RH018A>RH004A>RH031A>R H040A>RH015A.

More specifically, in these experiments, the tumor cell lines were used to seed multi-well tissue culture plates so that they were about 80% confluent on the day of infection. Representative wells from each tumor cell line were trypsinised and the number of cells in the well determined. These cell counts are used to determine the volume of each clinical isolate required to give an MOI of 1, 0.1, 0.01 and 0.001. Separate wells of a tumor cell line were infected with the clinical isolate at these MOI. All infections are carried out in quadruplicate. Duplicate wells were incubated for 24 hours and duplicate wells were incubated for 48 hours, both at 37° C., 5% $CO_2$, prior to fixation of the cells with glutaraldehyde and staining with crystal violet. The level of cell lysis was then assessed by gross observation, microscopy (cell counts) and photography.

Figure 4:
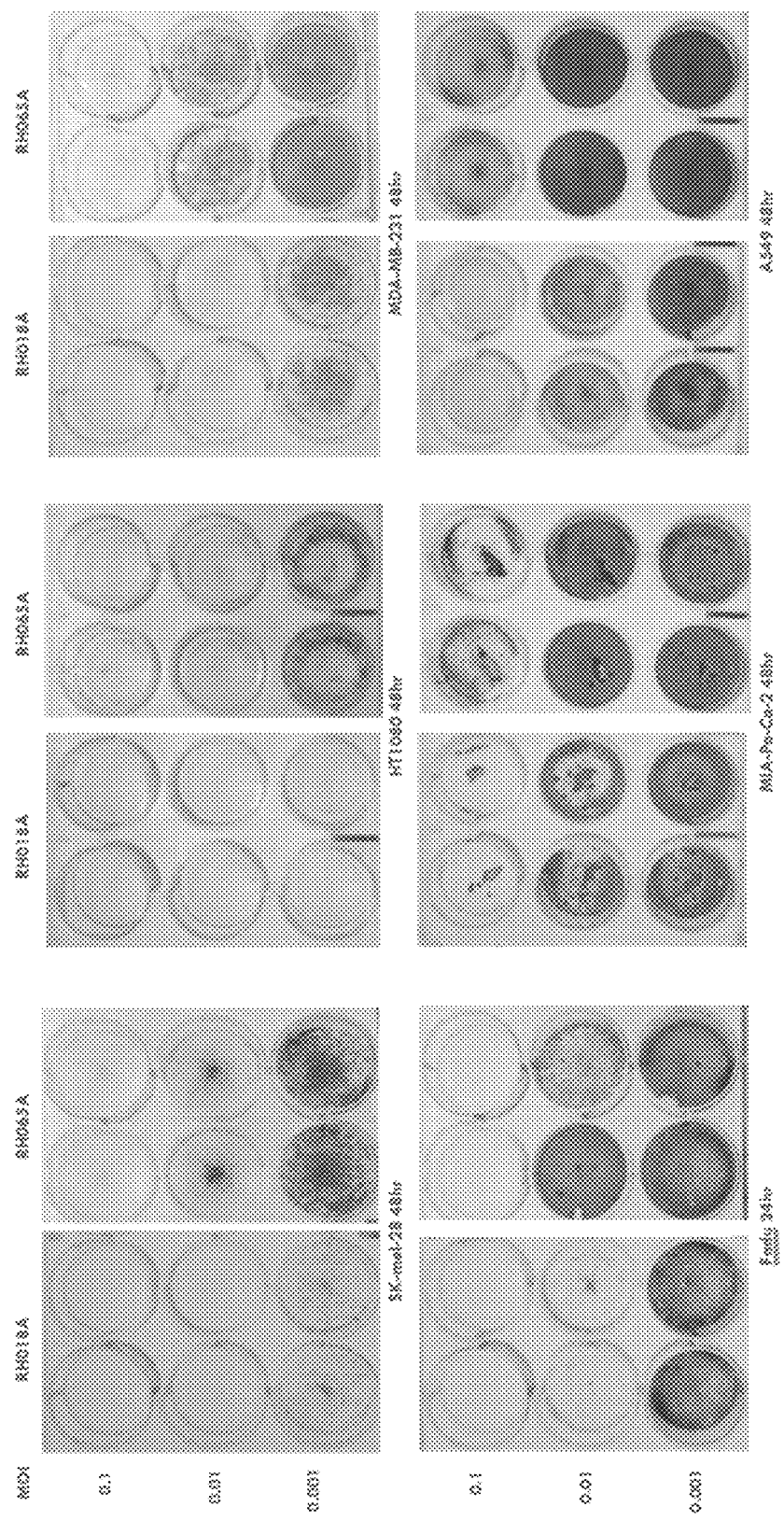
FIG. 4 shows a comparison between strain RH018A, the strain ranked first of all the strains tested, with an 'average' strain from the screen (i.e. strain RH065A). Approximately 10 fold less of strain RH018A was needed to kill an equal proportion of cells than was needed of strain RH065A as shown by crystal violet staining 24 or 48 hours post infection with MOIs of 0.1, 0.01 and 0.001 in SK-mel-28, HT1080, MDA-MB-231, Fadu. MIA-PA-CA-2 and A549 cell lines.
Figure 5A:
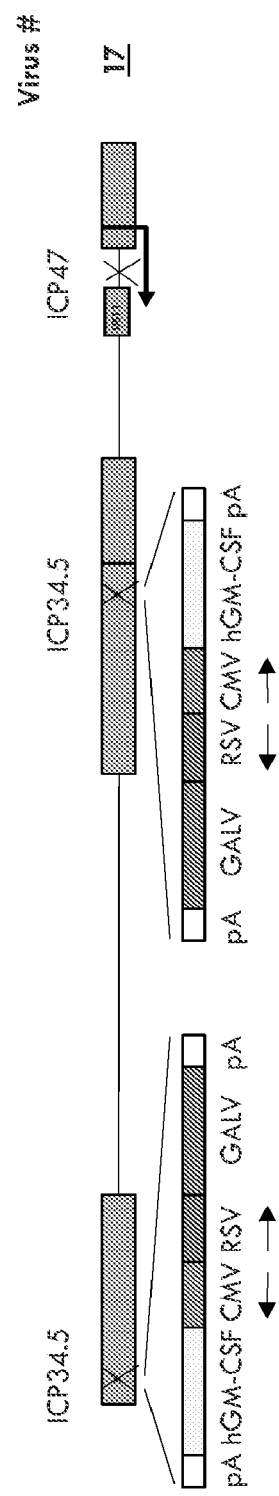
Figure 5B:
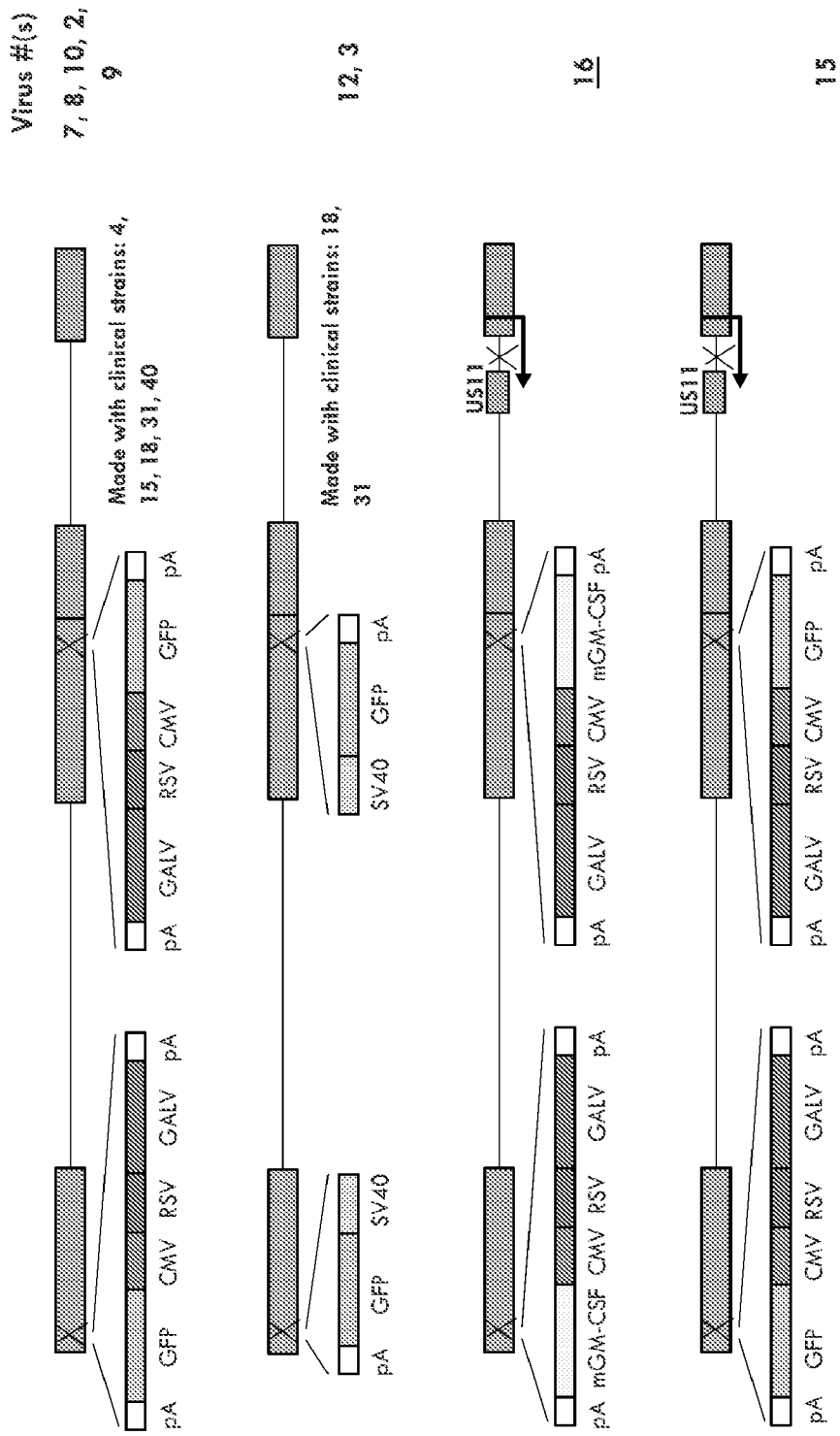
Figure 5C:
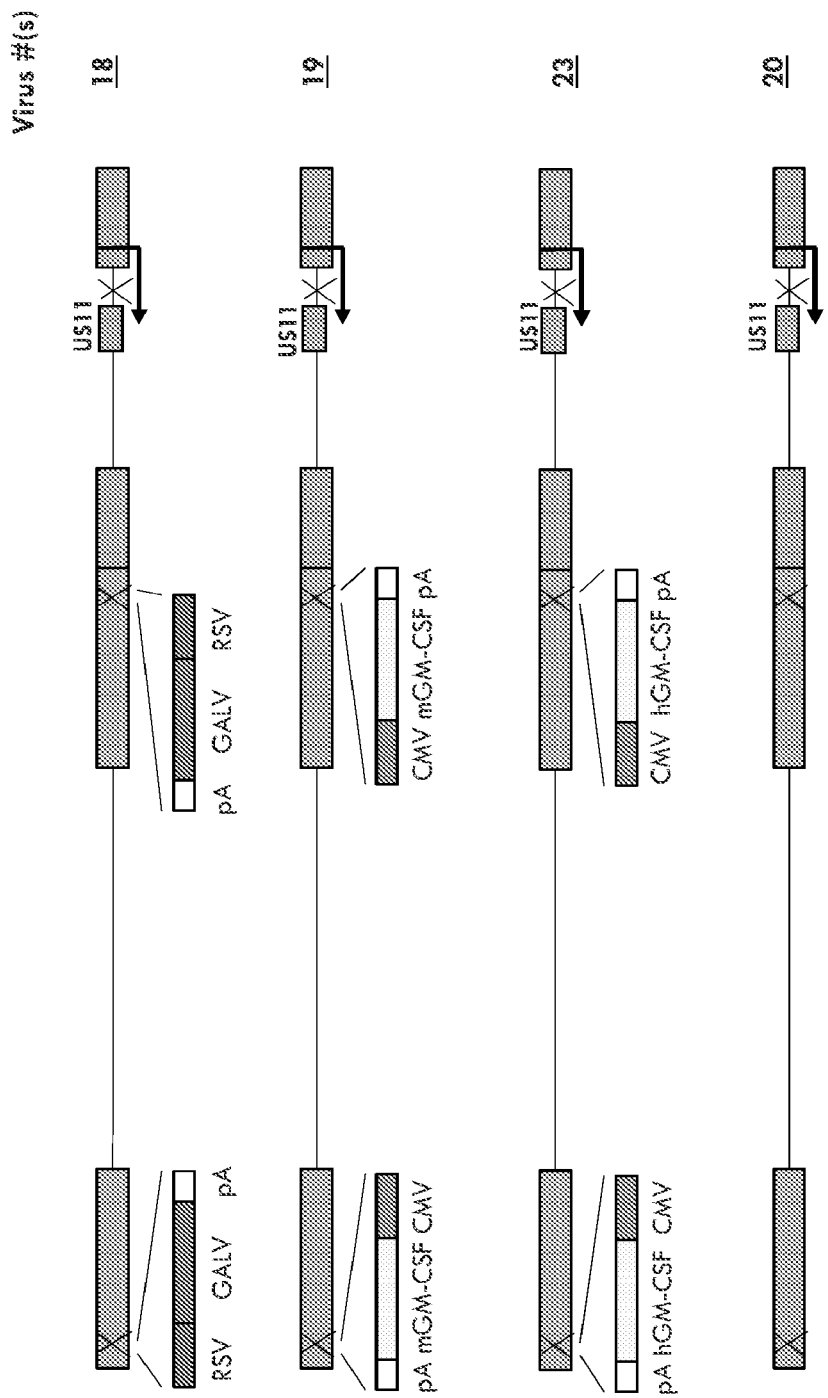
Figure 5E:
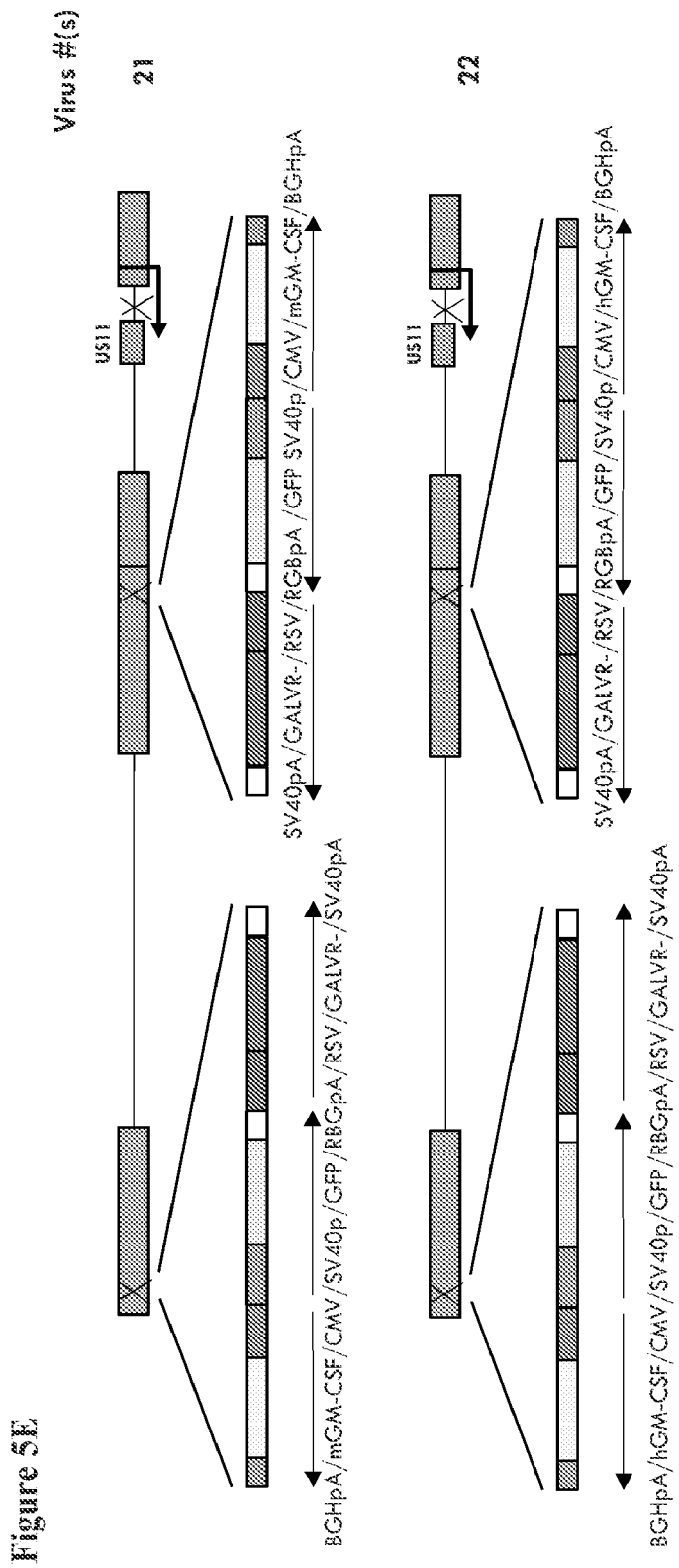
Figure 5H:
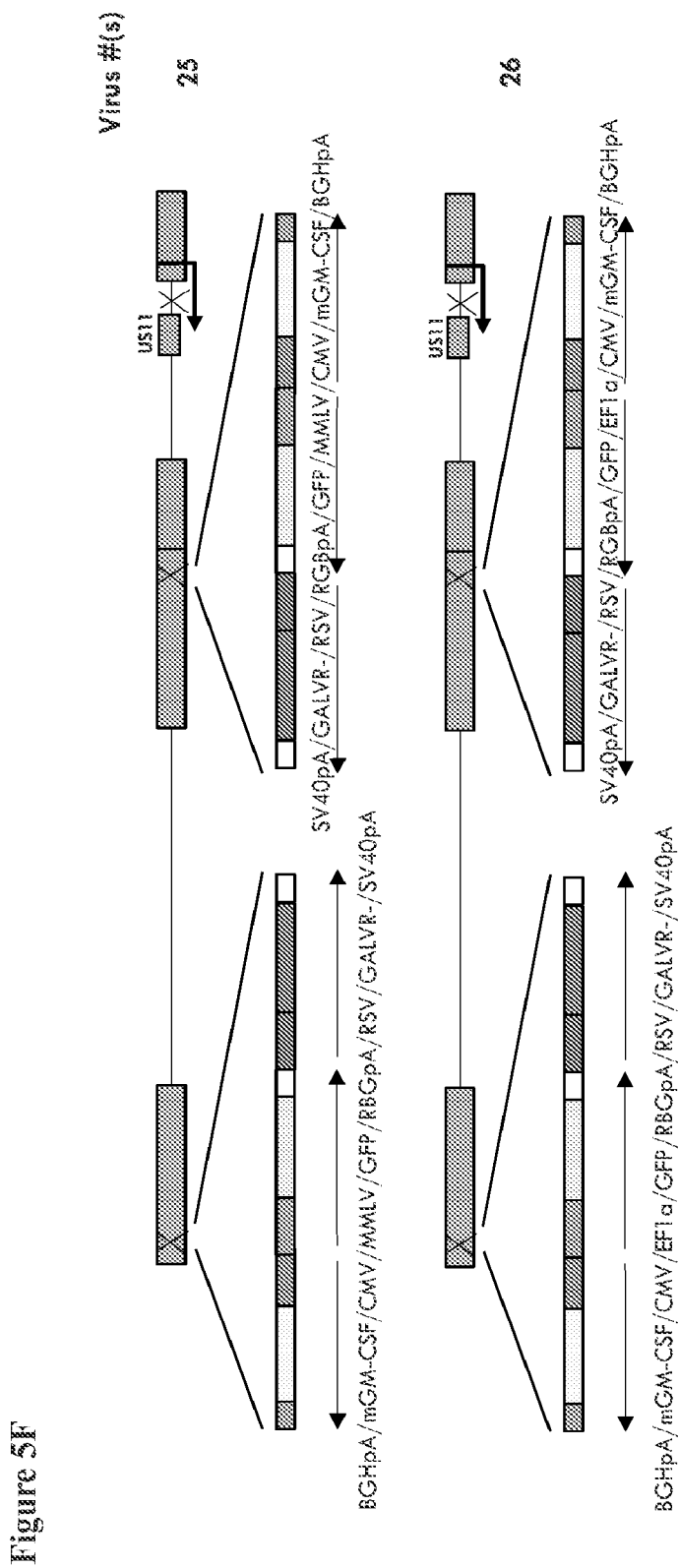
Figure 5G:
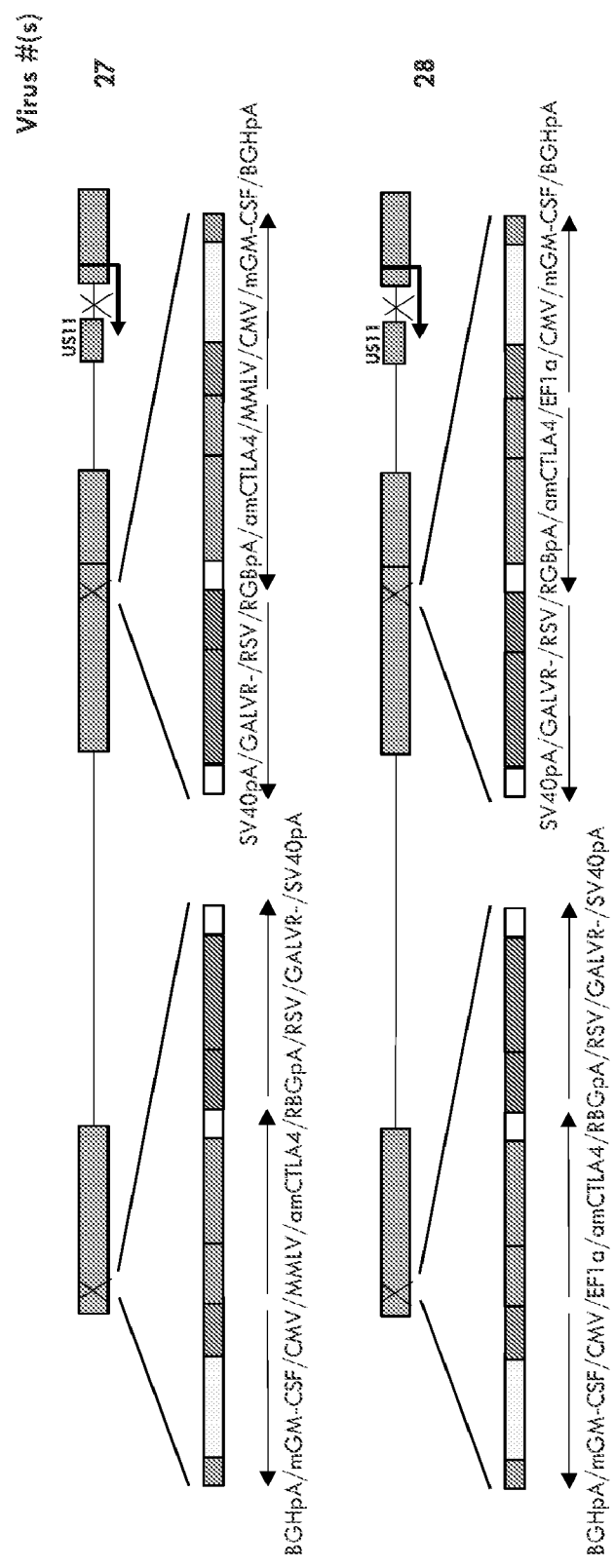
Figure 5H:
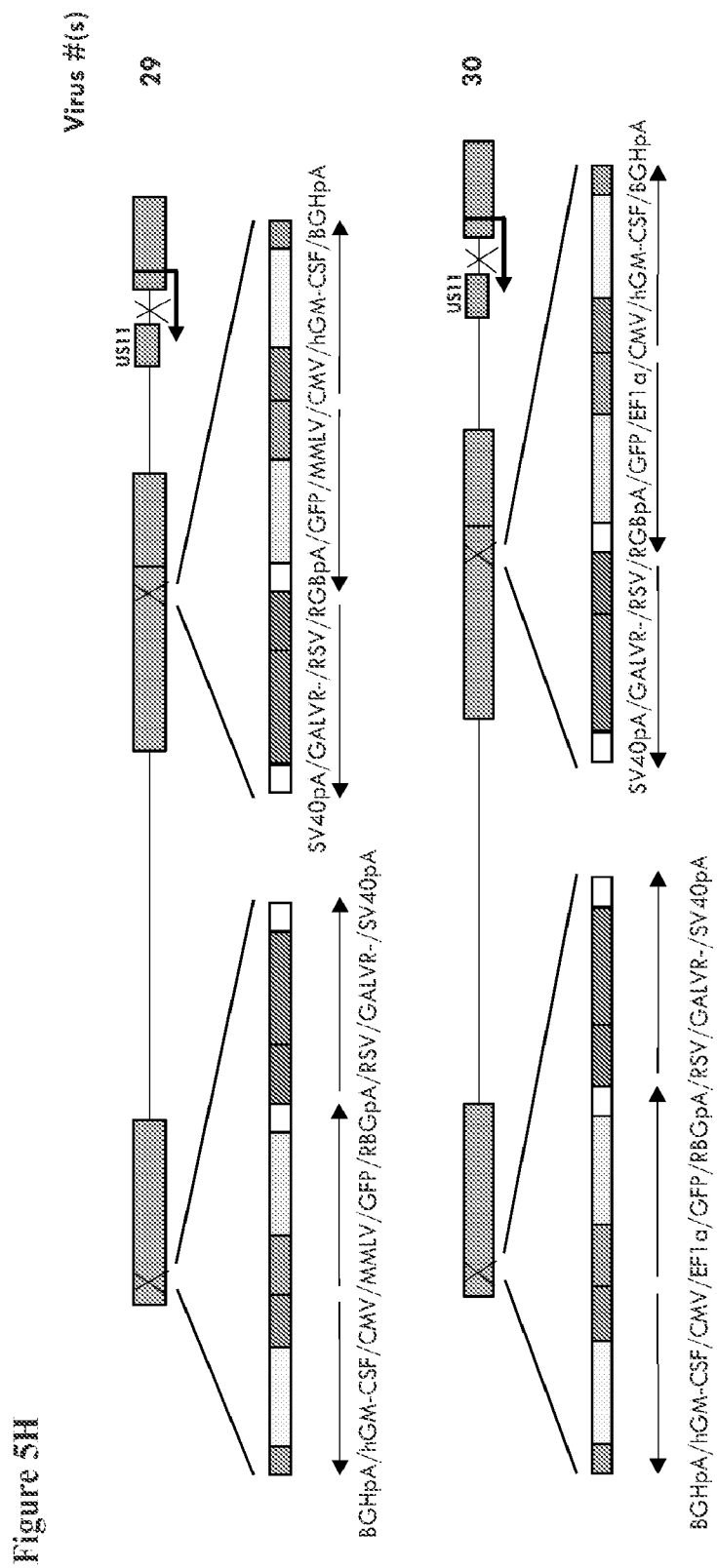
Figure 51:
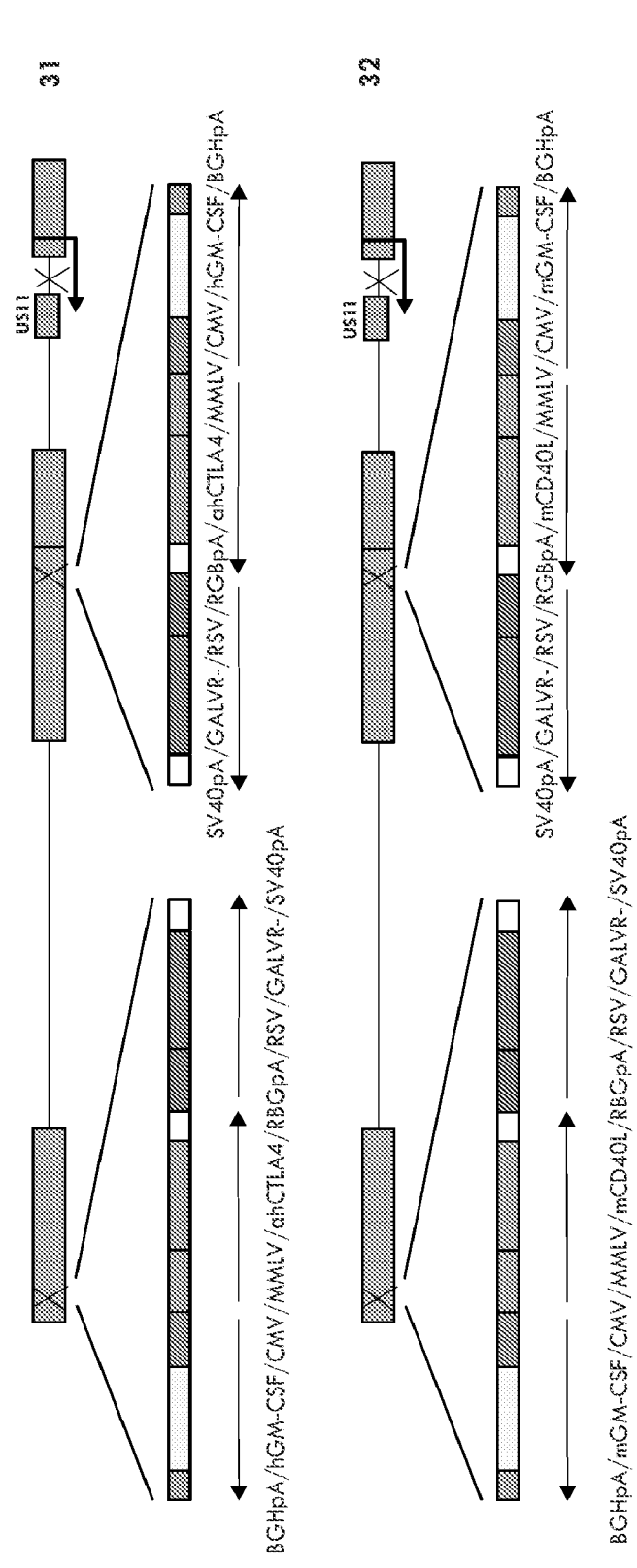
Figure 5J:
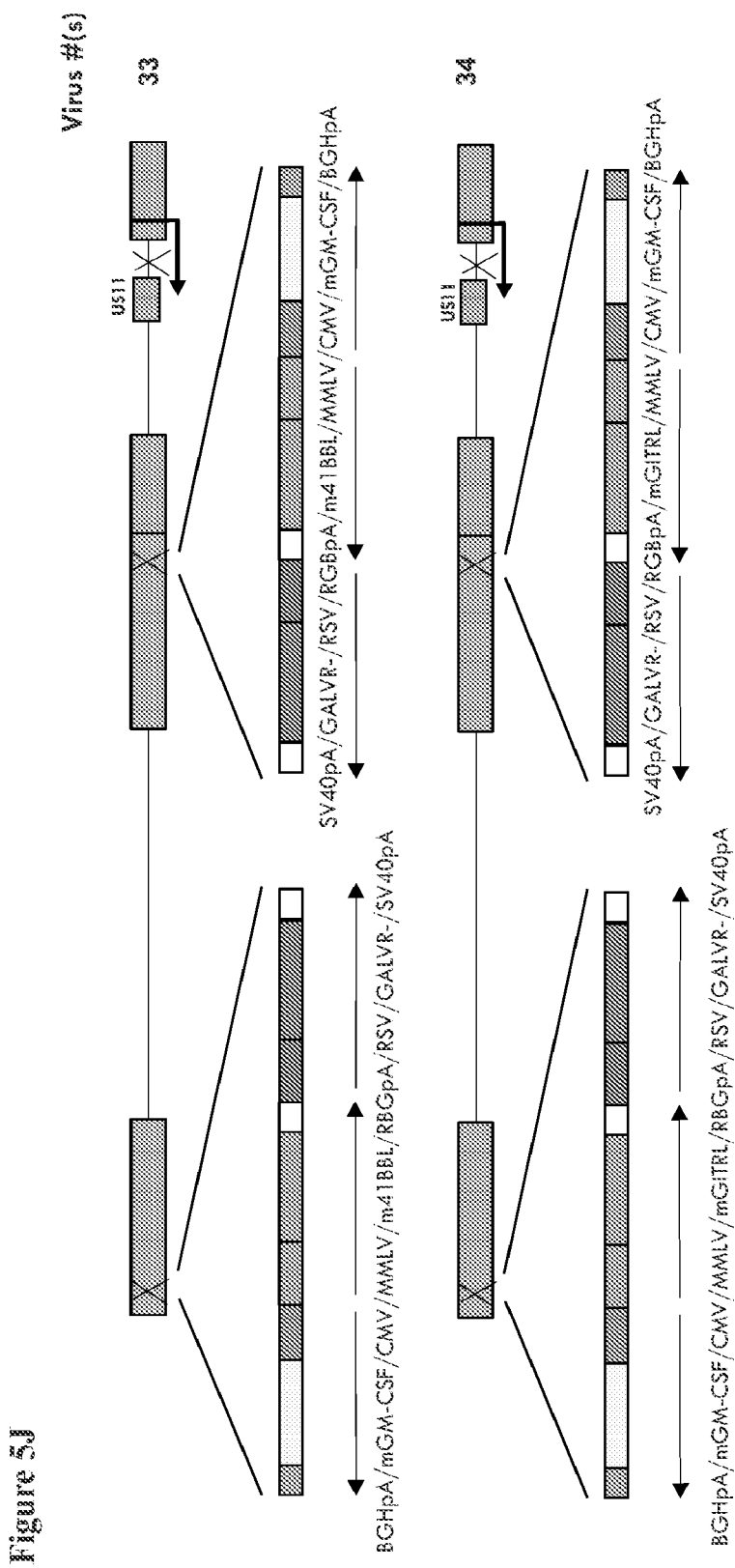
Figure 5K:
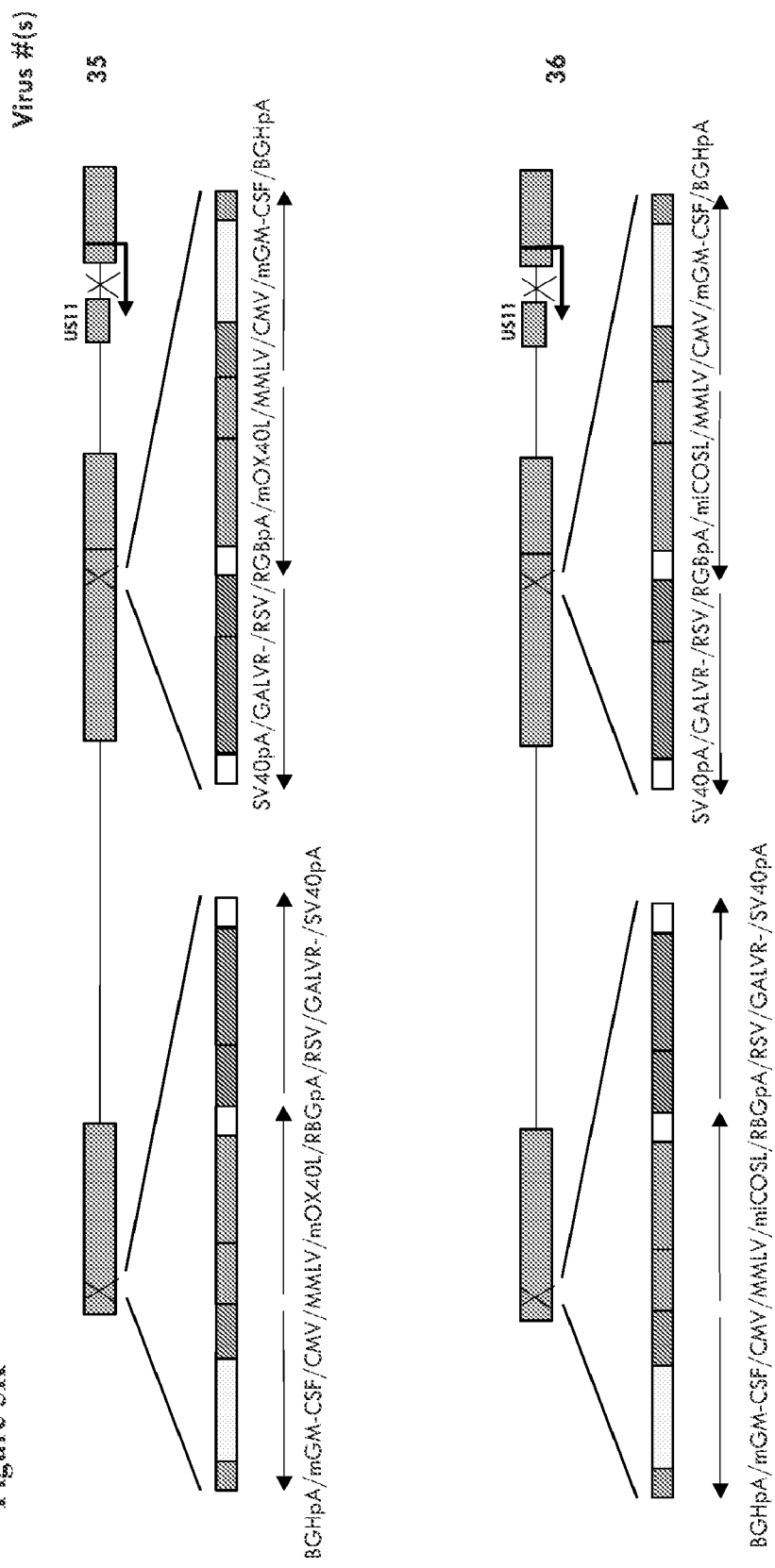

Strain RH018A, the strain ranked first of all the strains tested was compared to an 'average' strain from the screen (i.e. a strain which was not in the top 8, but was also not in the group of strains which were least effective and killing the panel of tumor cell lines). This comparison showed that Strain RH018A was approximately 10 fold more effective than this average strain (Strain RH065A) at killing the tumor cell lines (i.e. approximately 10 fold less of Strain RH018A was needed to kill an equal proportion of cells than was needed of Strain RH065A). This is shown in FIG. 4.

Example 8. Modification of Clinical Isolates

In this Example the clinical isolates selected in Example 7 were modified by deletion of ICP34.5 from the viral genome using homologous recombination with a plasmid containing regions flanking the ICP34.5 encoding gene (nucleotides 143680-145300 and 145.582-147,083 HSV1 strain 17 sequence Genbank file NC 001806.2) between which are encoded GFP and the GALV-R-fusogenic glycoprotein. The structure of this virus. (Virus 10) is shown in FIGS. 5A-5K.

Additional viruses based on Strain RH018A were also constructed in which both ICP34.5 and ICP47 (using flanking regions containing nucleotides 123464-124953 and 125727-126781: HSV1 strain 17 sequence Genbank file NC 001806.2) were deleted (resulting in placement of US11 under the control of the ICP47 promoter). To construct these viruses. GFP expressing virus plaques, with GFP expressed in place of ICP47 were first selected. GFP was then removed by homologous recombination with the empty flanking regions, and plaques not expressing GFP were selected. This resulted in an ICP47 deleted virus in which US11 is expressed as an IE protein as it is now under the control of the ICP47 promoter. ICP34.5 was then deleted using homologous recombination with a plasmid containing regions flanking HSV1 nucleotides 143680-145300 and 145.582-147,083; HSV1 strain 17 sequence Genbank file NC 001806.2) between which GFP is encoded. GFP expressing virus plaques were again selected, and GFP then removed by homologous recombination with the same flanking regions but between which are now an expression cassette comprising the genes to be inserted. The viruses that were constructed are shown in FIGS. 1 and 5A-5K. These included a codon optimized version of the mouse GM-CSF sequence and a codon optimized version of the GALV R- sequence driven by the CMV IE promoter and RSV promoter respectively, in a back to back orientation and again selecting virus plaques which do not express GFP. This virus construction was performed using methods which are standard in the art.

The mGM-CSF and GALV-R- sequences are shown in SEQ ID NOs 2 and 8 respectively. The structure of the resulting virus was confirmed by PCR, GM-CSF expression was confirmed by ELISA, and GALV-R- expression was confirmed by infection of human HT1080 tumor cells and the observation of syncitial plaques.

Figure 6:
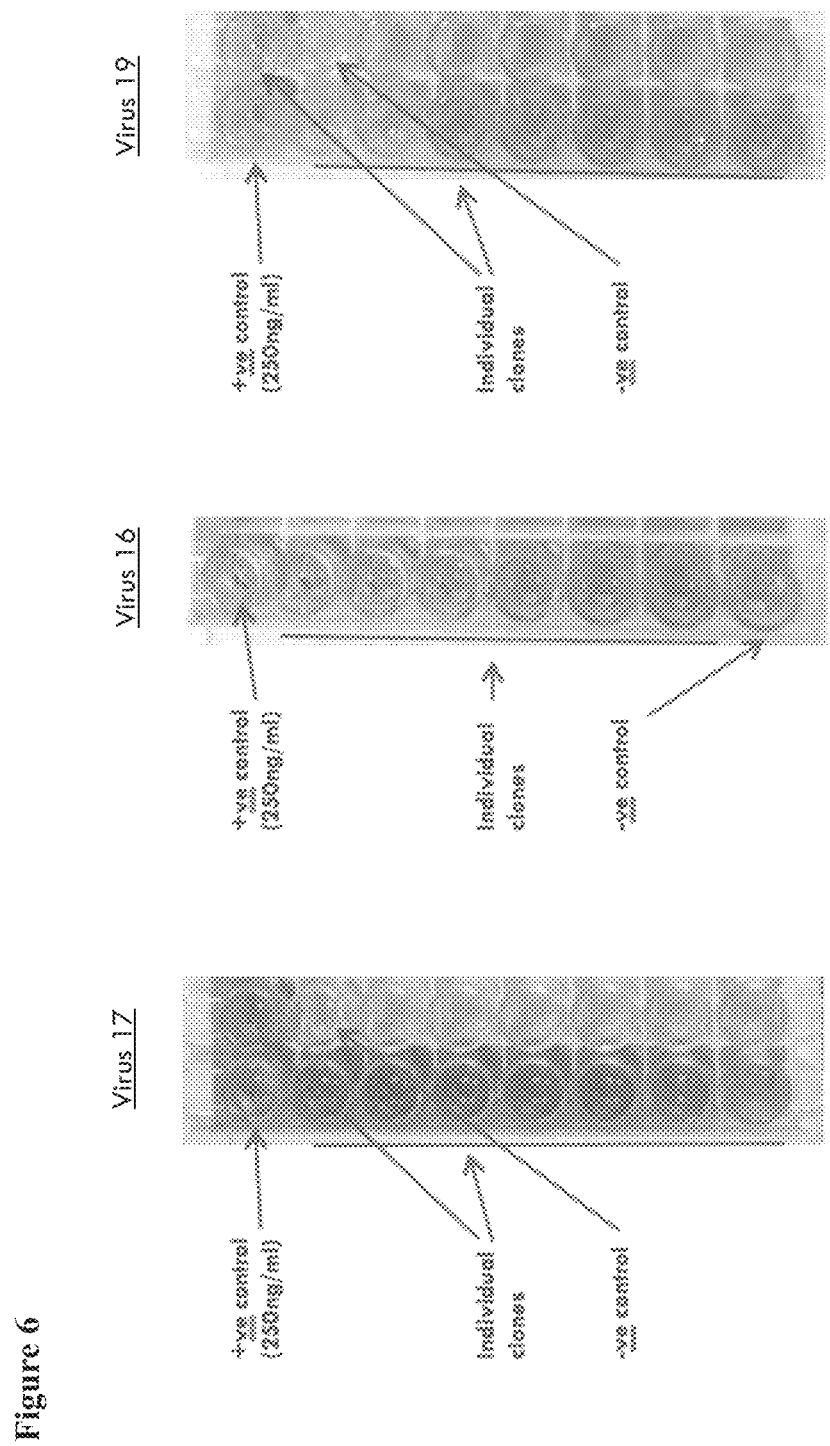
FIG. 6 shows the results of an ELISA to detect expression of human or mouse GM-CSF in supernatants from BHK cells infected with virus 16 (mGM-CSF and GALVR-), virus 17 (hGM-CSF and GALVR-) and virus 19 (mGM-CSF).

For human use, hGM-CSF is used, the sequence for a codon optimised version of which is shown in SEQ ID NO 4. The structure of this virus is shown in FIGS. 5A-5K. Expression of mouse or human GM-CSF from viruses 16, 17 and 19 is shown in FIG. 6.

Figure 7A:
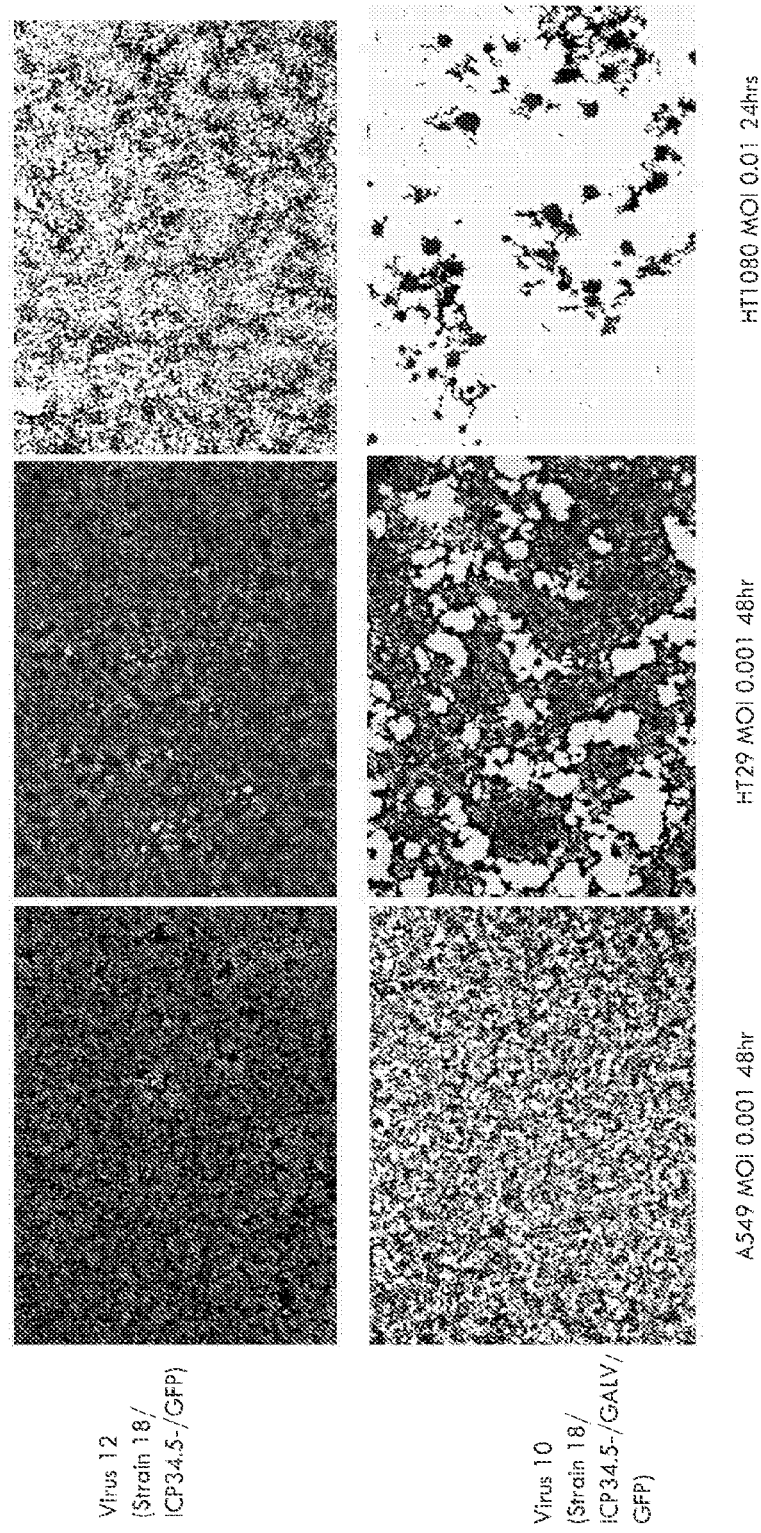
FIGS. 7A and 7B are a comparison between the cell-killing abilities of strain RH018A in which ICP34.5 is deleted and which expresses GALVR- and GFP (virus 10) with a virus that expresses only GFP (virus 12) as determined by crystal violet staining in three cell lines at low magnification.
Figure 7B:
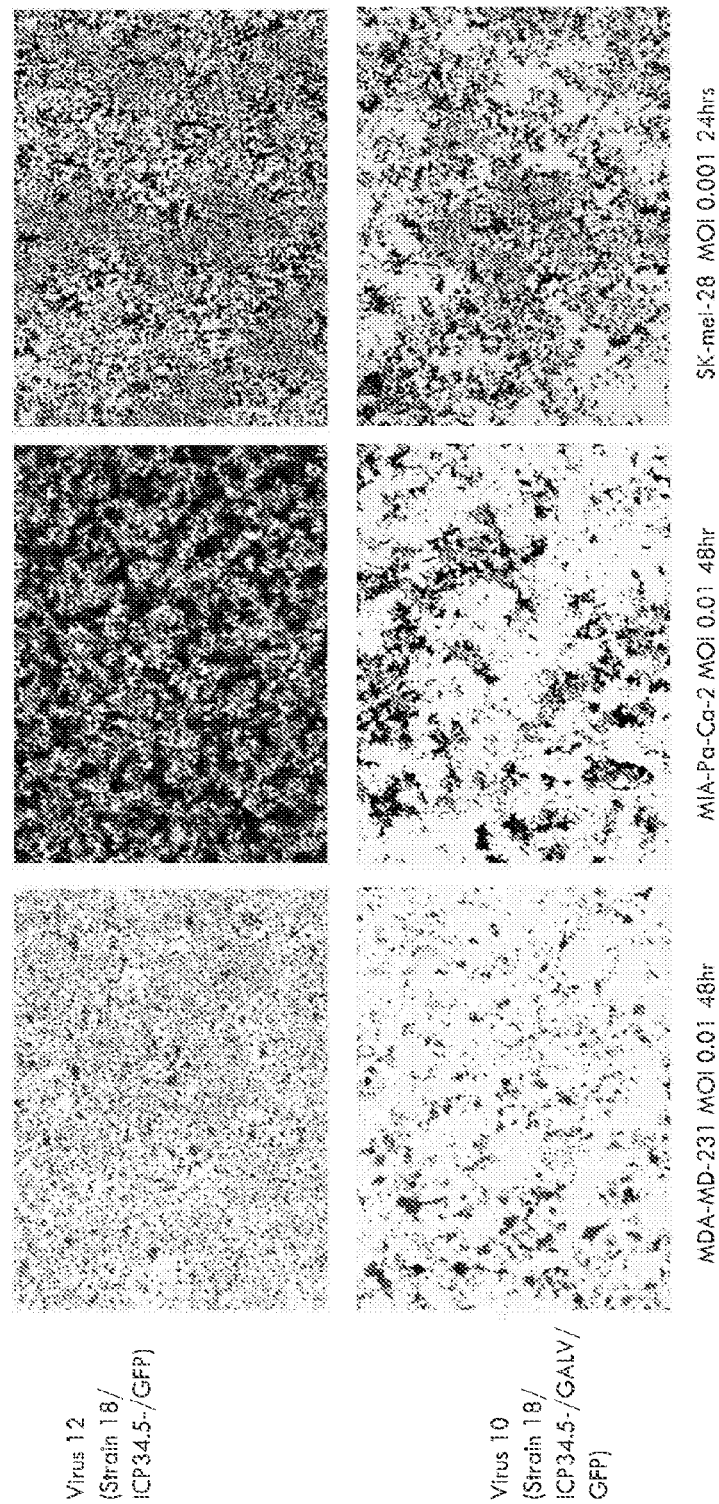

Example 9. A Virus of the Invention Modified for Oncolytic Use and Expressing a Fusogenic Glycoprotein Shows Enhanced Tumor Cell Killing In Vitro as Compared to a Virus which does not Express a Fusogenic Glycoprotein Virus 10 (see FIGS. 5A-5K), based on clinical Strain RH018A in which ICP34.5 is deleted and which expresses GALVR- and GFP, was compared in vitro to a virus which expresses only GFP (Virus 12). Virus 10 showed enhanced killing on a panel of human tumor cell lines as compared to Virus 12, as shown in FIGS. 7A and 7B.

Figure 8A:
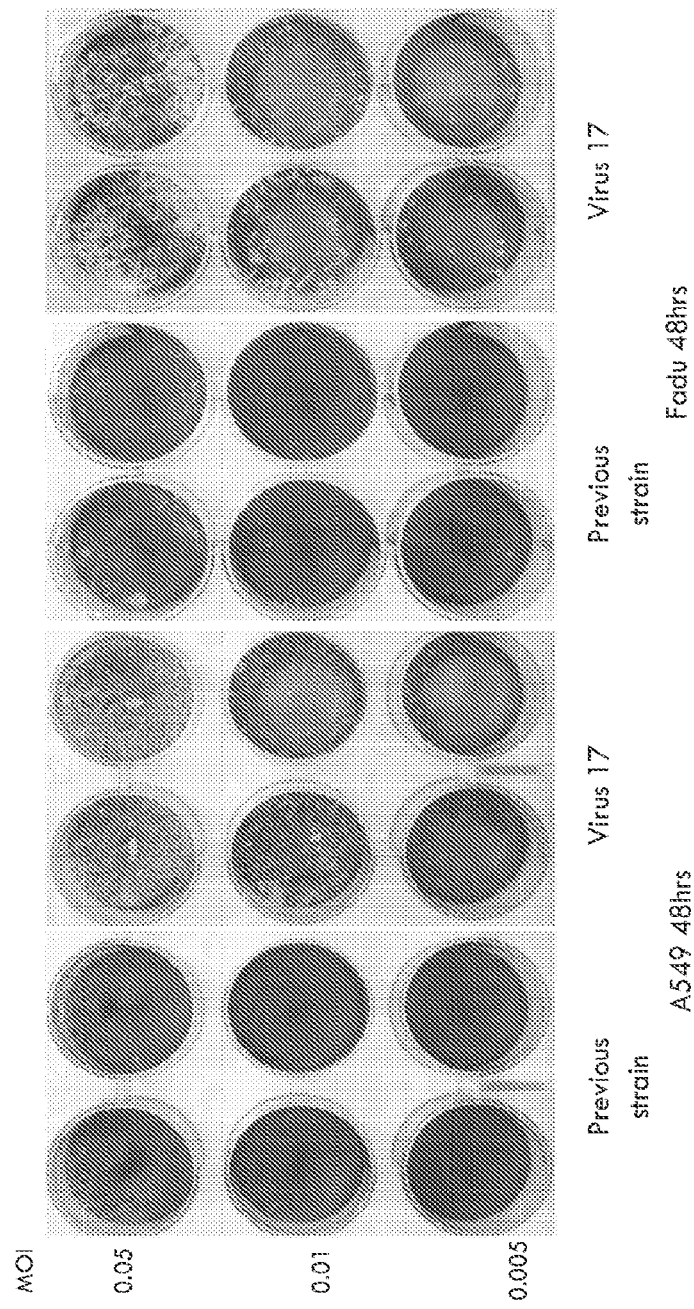
FIGS. 8A and 8B are a comparison between the cell-killing abilities of strain RH018A in which ICP34.5 and ICP47 are deleted and which expresses GALVR- and GM-CSF (virus 17) with a prior art strain with the same modifications as determined by crystal violet staining in four cell lines.
Figure 8B:
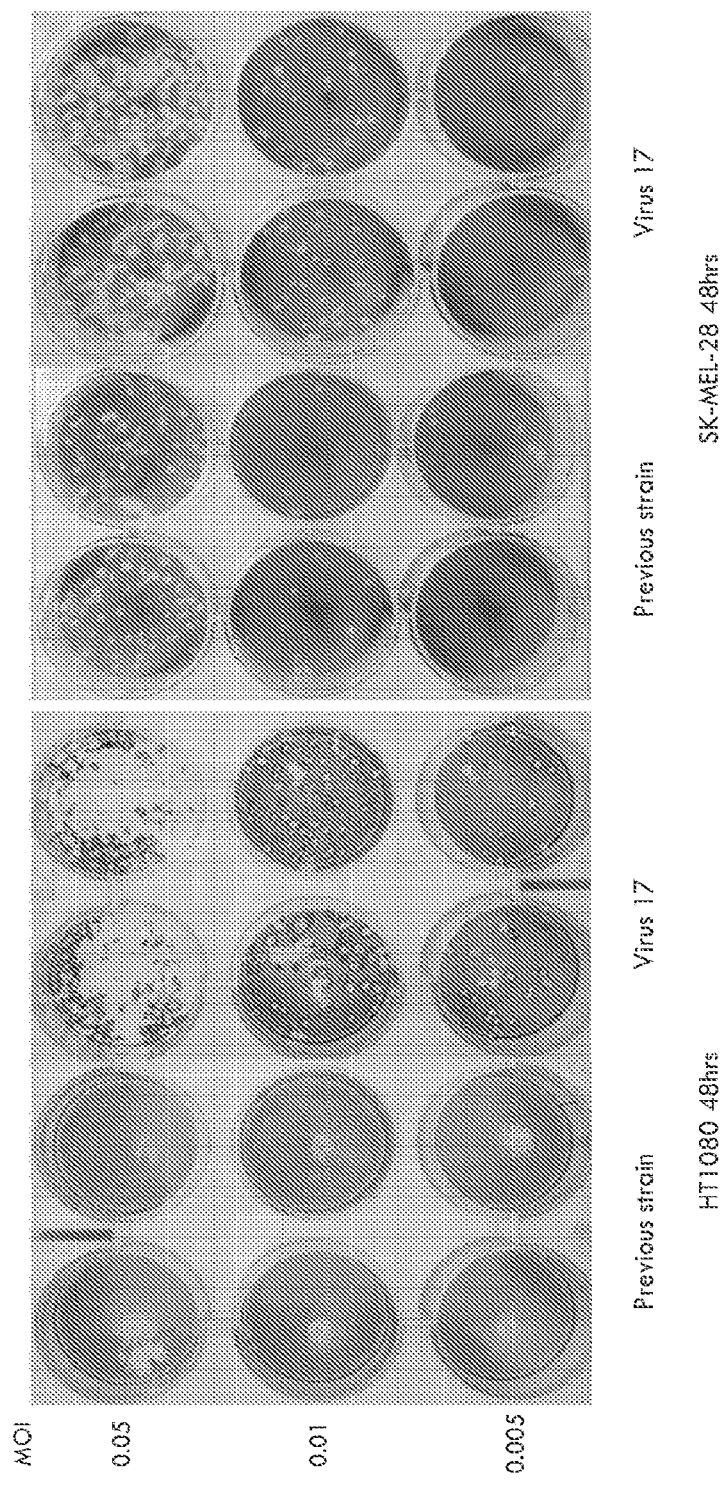

Example 10. A Virus of the Invention Modified for Oncolytic Use Shows Enhanced Tumor Cell Killing as Compared to a Similarly Modified Virus which is not of the Invention Virus 17 (see FIGS. 5A-5K), based on clinical Strain RH018A in which ICP34.5 and ICP47 are deleted and which expresses GALVR- and GM-CSF, was compared in vitro to a known virus which was also deleted for ICP34.5 and ICP47 but which was not derived from a strain of the invention and which expresses only GM-CSF. Virus 17 showed enhanced killing on a panel of human tumor cell lines as compared to the previous virus, as shown in FIGS. 8A and 8B.

Figure 9:
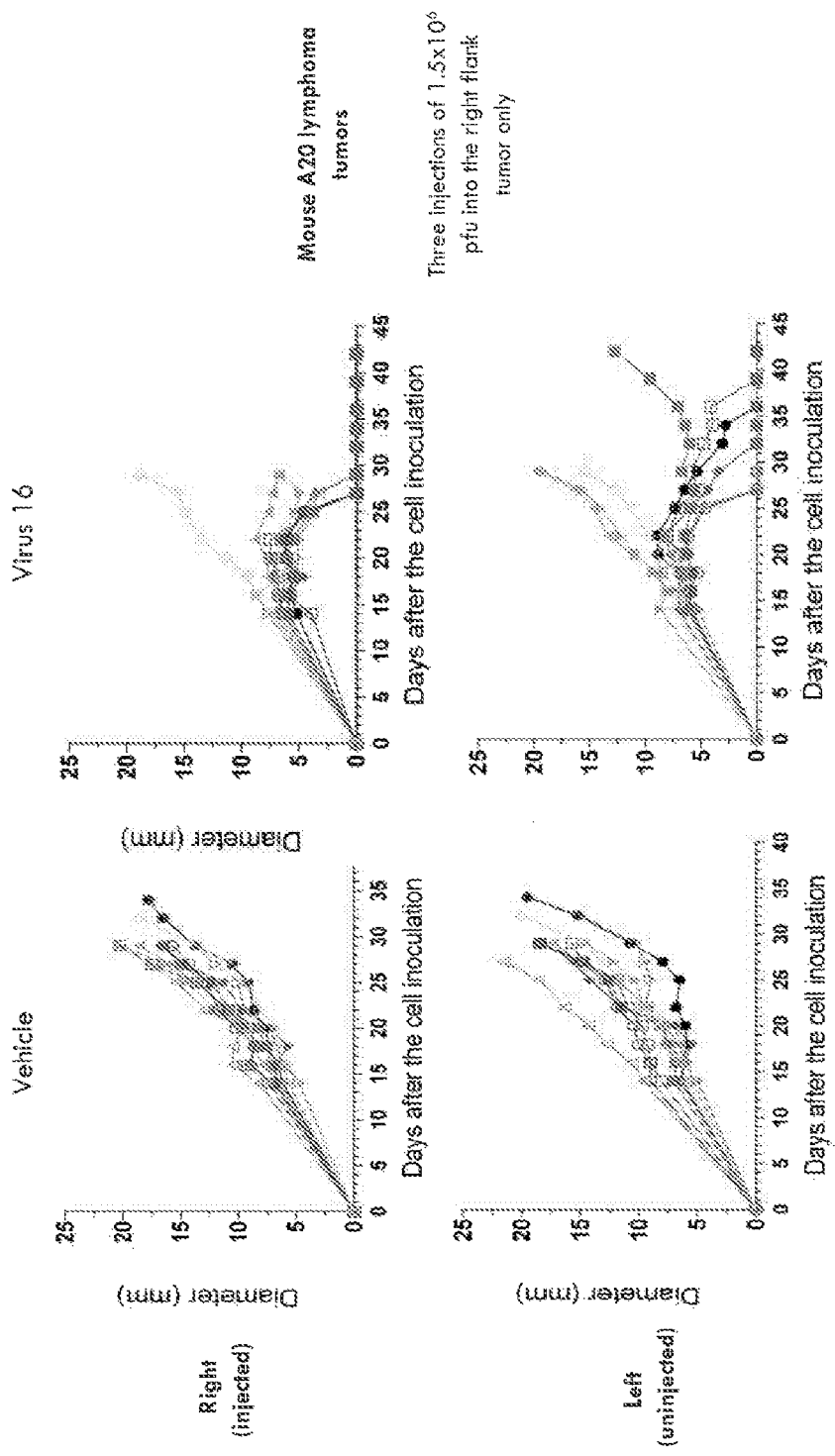
FIG. 9 shows the effectiveness of Virus 16 (ICP34.5 and ICP47 deleted expressing GALVR- and mGM-CSF) in treating mice harbouring A20 lymphoma tumors in both flanks. Tumors on the right flanks were injected with the virus or vehicle and the effects on tumor size was observed for 30 days. The virus was effective against both injected tumors and non-injected tumors.

Example 11. A Virus of the Invention Modified for Oncolytic Use Effectively Treats Mouse Tumors In Vivo Virus 16 was tested in mice harboring A20 lymphoma tumors in the left and right flanks. One million tumor cells were first implanted in both flanks of Balb/c mice and tumors allowed to grow to 0.5-0.7 cm in diameter. Tumors on the right flank were then injected 3 times (every other day) with either vehicle (10 mice) or 5×10 exp 6 pfu of Virus 16 (10 mice), and effects on tumor size observed for a further 30 days. This demonstrated that both injected and uninjected tumors were effectively treated with Virus 16 (see FIG. 9).

Example 12. The Effect of the Combined Expression of a Fusogenic Protein and an Immune Stimulatory Molecule from an Oncolytic Virus of the Invention in a Rat Tumor Model The GALV R- protein causes cell to cell fusion in human cells but not in mouse cells. However. GALV R- does cause fusion in rat cells.

The utility of the invention was further demonstrated by administering 9L cells into the flanks of Fischer 344 rats and allowing the 9L tumors to grow to approximately 0.5 cm in diameter.

The following treatments were then administered to groups of rats (ten per group), into one flank only of each rat three times per week for three weeks:

50 μl of vehicle;
50 μl of 107 pfu/ml of Virus 19 (expresses mGM-CSF but not GALV R-);
50 μl of $10^7$ pfu/ml of Virus 16 (expresses both mouse GM-CSF and GALV-R-).

Figure 10:
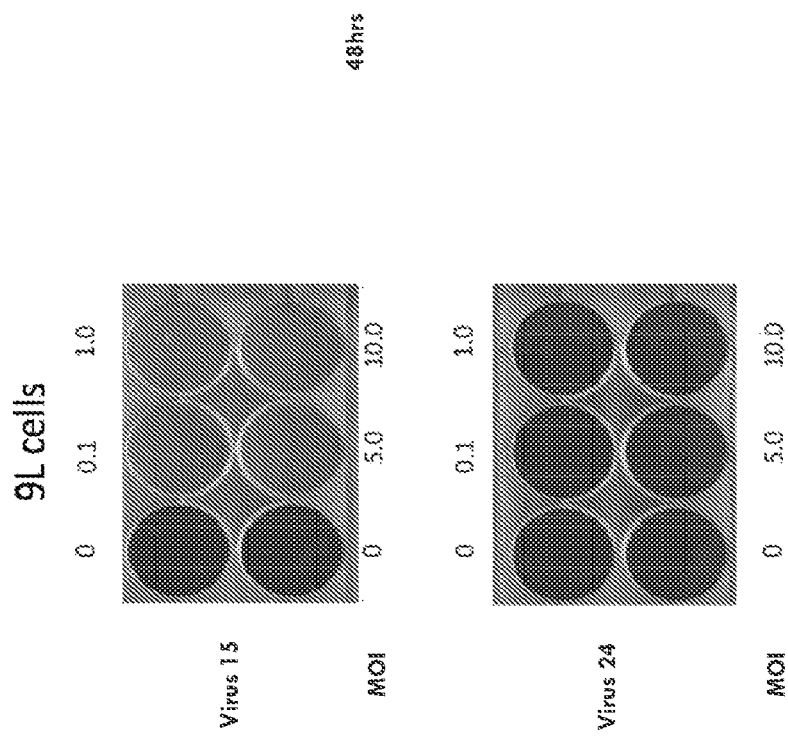
FIG. 10 demonstrates the effects of Virus 15 (ICP34.5 and ICP47 deleted expressing GALVR- and GFP) and Virus 24 (ICP34.5 and ICP47 deleted expressing GFP) on rat 9L cells in vitro as assessed by crystal violet staining. The virus expressing GALV (Virus 15) showed enhanced killing of rat 9L cells in vitro as compared to a virus which does not express GALV (Virus 24).
Figure 15:
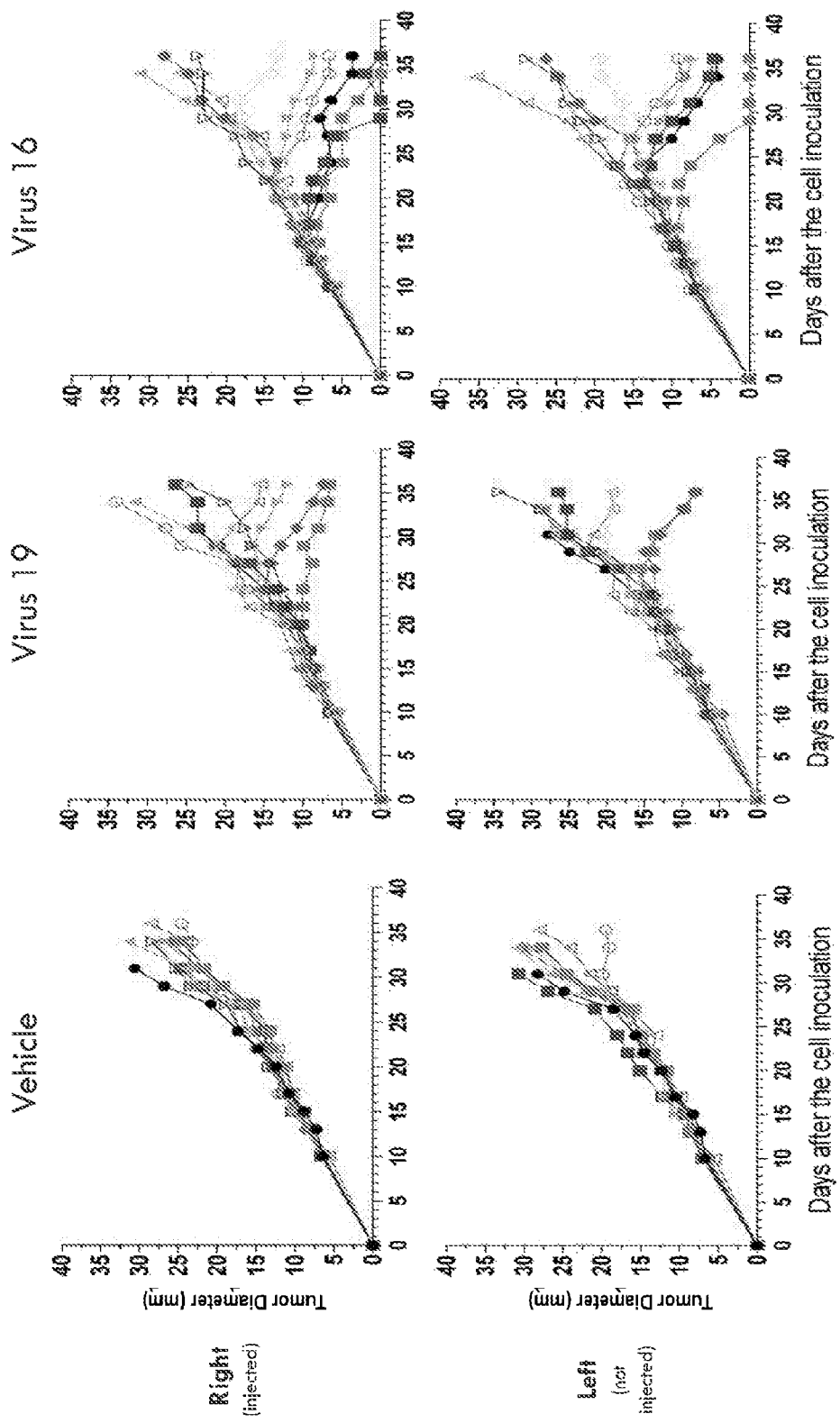
FIG. 15 demonstrates the effects of viruses of the invention expressing GALVR- on 9L cells in the flanks of Fischer 344 rats. The following treatments were administered to groups of rats (ten per group), into one flank of each rat only three times per week for three weeks: 50 µl of vehicle; 50 µl of 10$^7$ pfu/ml of Virus 19 (expresses mGM-CSF but not GALV R-); or 50 µl of 10$^7$ pfu/ml of Virus 16 (expresses both mouse GM-CSF and GALV-R-). Effects on tumor growth were then observed for a further 30 days. Superior tumor control and shrinkage was observed with the virus expressing GM-CSF and GALV-R- as compared to the virus expressing GM-CSF alone.

Effects on tumor growth were then observed for a further ≈30 days. This demonstrated superior tumor control and shrinkage with the virus expressing GALV-R- in both injected and uninjected tumors, demonstrating improved systemic effects. This is shown in FIG. 15. FIG. 10 shows that a virus expressing GALV (Virus 15) also shows enhanced killing of rat 91 cells in vitro as compared to a virus which does not express GALV (Virus 24).

Example 13. A Virus of the Invention Modified for Oncolytic Use is Synergistic with Immune Checkpoint Blockade in Mouse Tumor Models Virus 16 was tested in mice harboring CT26 tumors in the left and right flanks. One million tumor cells were first implanted in both flanks of Balb/c mice and tumors allowed to grow to 0.5-0.6 cm in diameter.

Figure 11A:
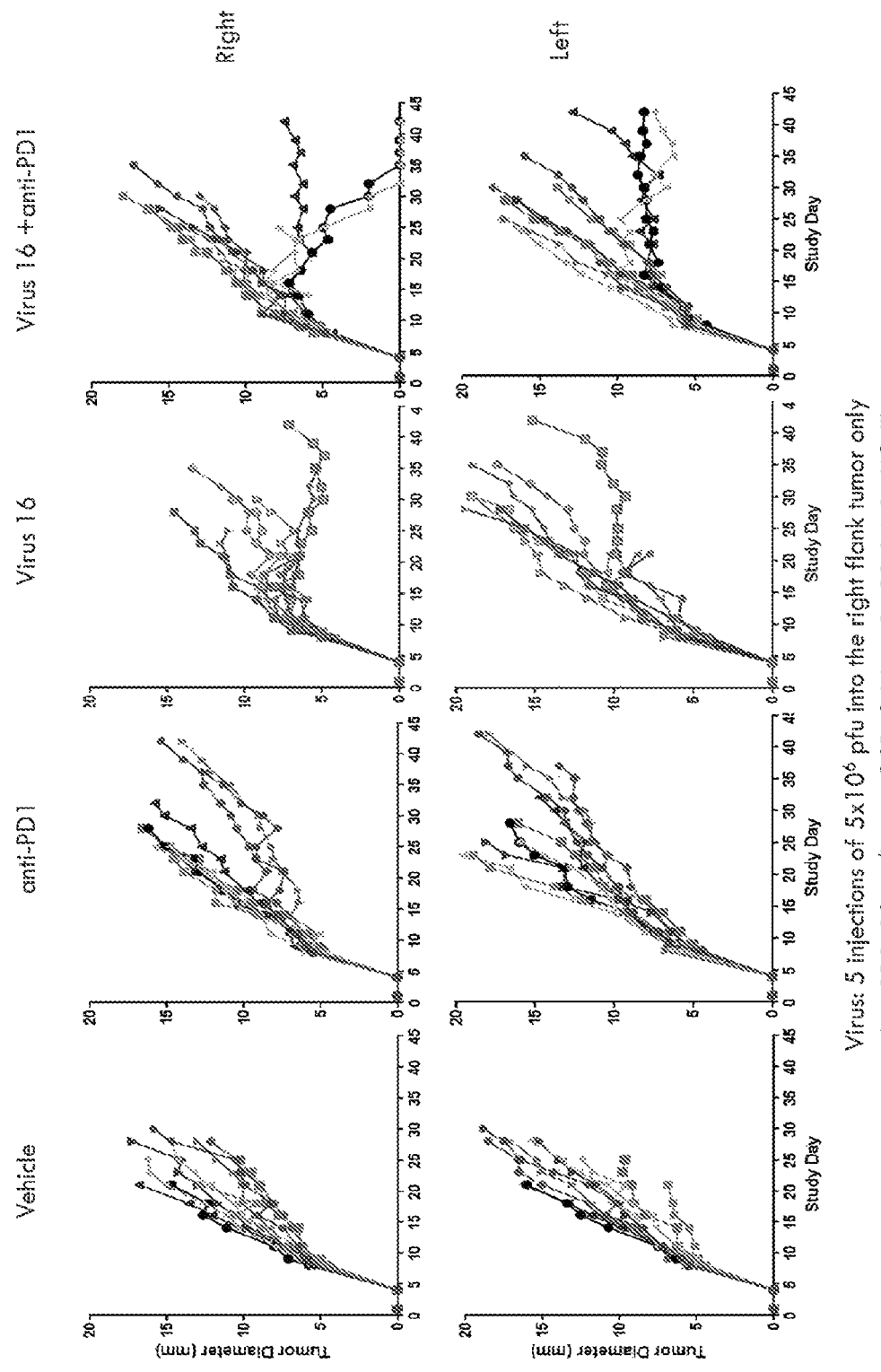
FIGS. 11A-11C show the antitumor effects of Virus 16 in Balb/c mice harboring mouse CT26 tumors in the left and right flanks. Groups of 10 mice were then treated with: Vehicle (3 injections into right flank tumors every other day); 5×10 exp 6 pfu of Virus 16 (mRP1) injected in the right flank tumor every other day; anti-mouse PD1 alone (10 mg/kg i.p. every three days, BioXCell clone RMP1-14); anti-mouse CTLA-4 (3 mg/kg i.p every three days, BioXCell clone 9D9); anti-mouse PD1 together with Virus 16; anti-mouse CTLA4 together with Virus 16; 1-methyl trypotophan (I-MT; IDO inhibitor (5 mg/ml in drinking water)); anti-mouse PD1 together with 1-methyl trypotophan; or anti-mouse PD1 together with 1-methyl trypotophan and Virus 16. Effects on tumor size were observed for a further 30 days. Greater tumor reduction was seen in animals treated with combinations of virus and checkpoint blockade than with the single treatment groups.
Figure 11B:
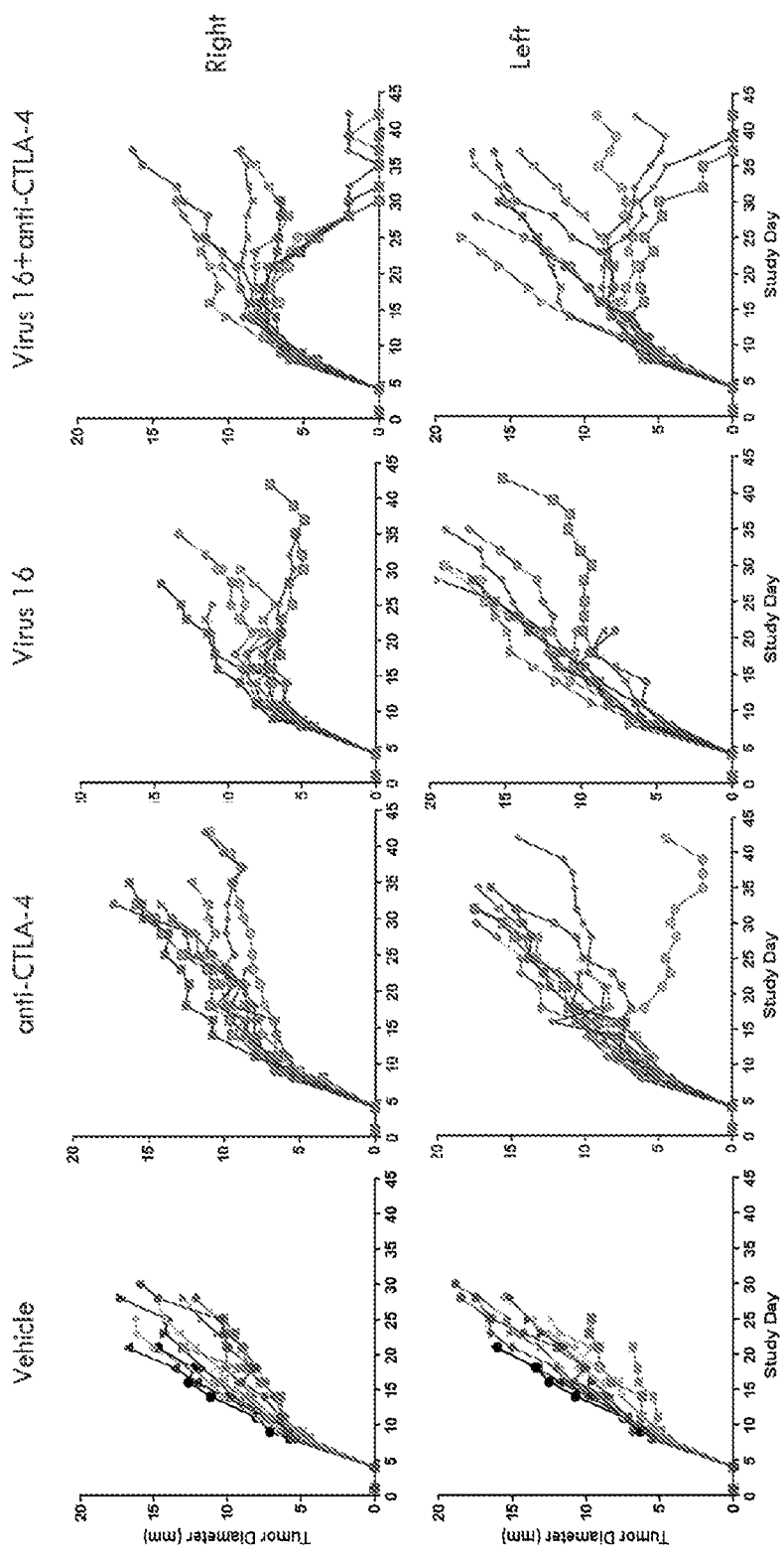
Figure 11C:
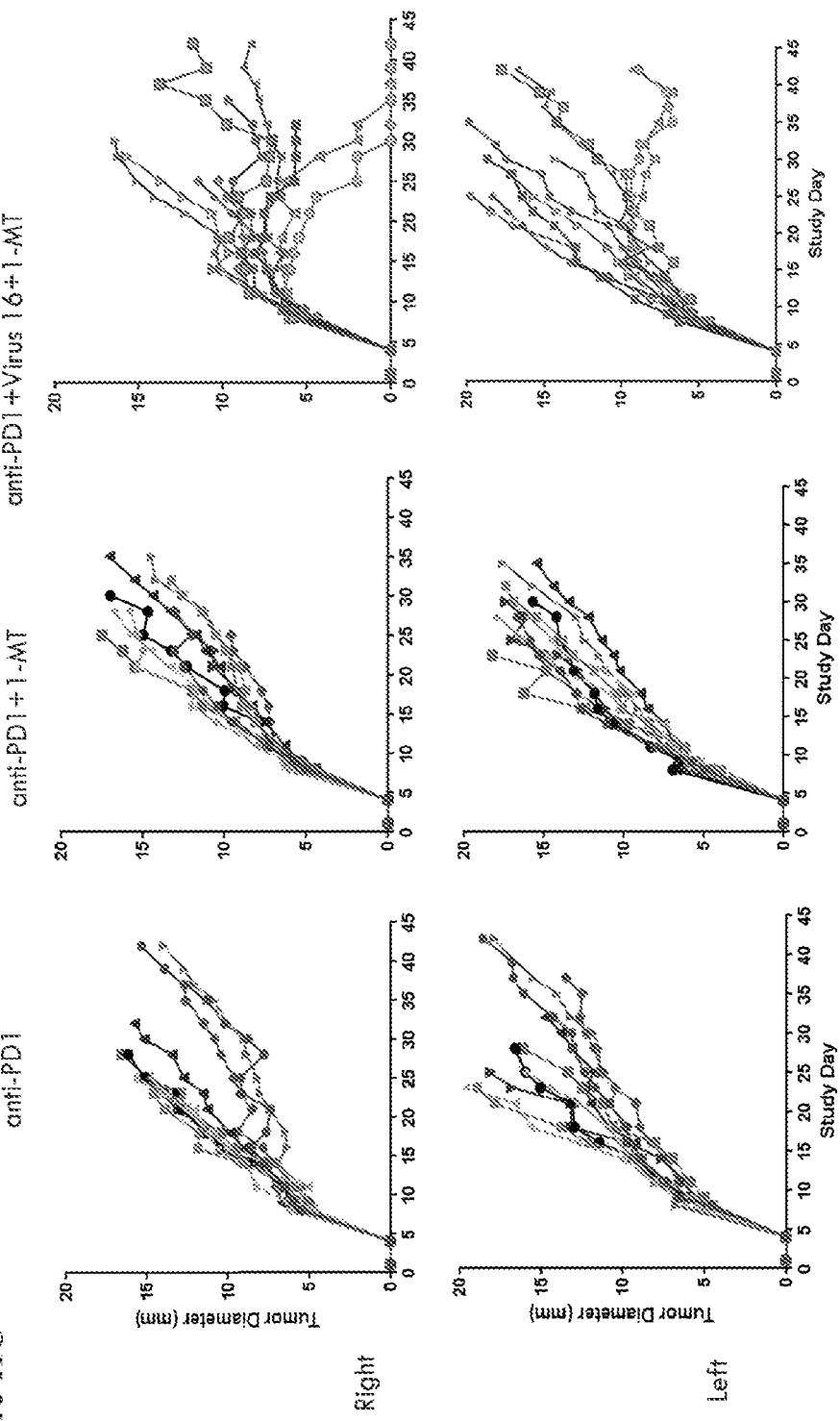
Figure 12A:
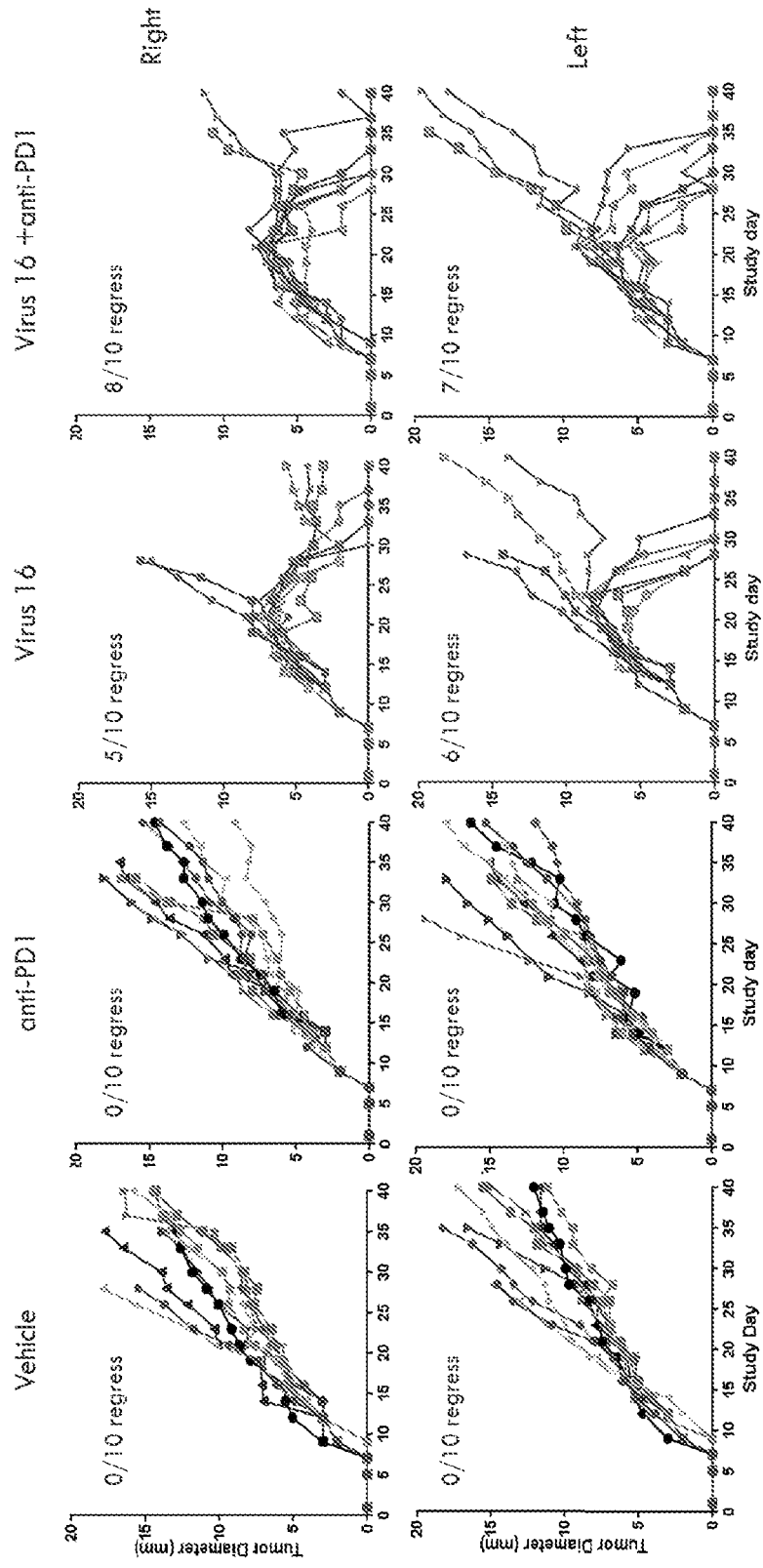
Figure 12B:
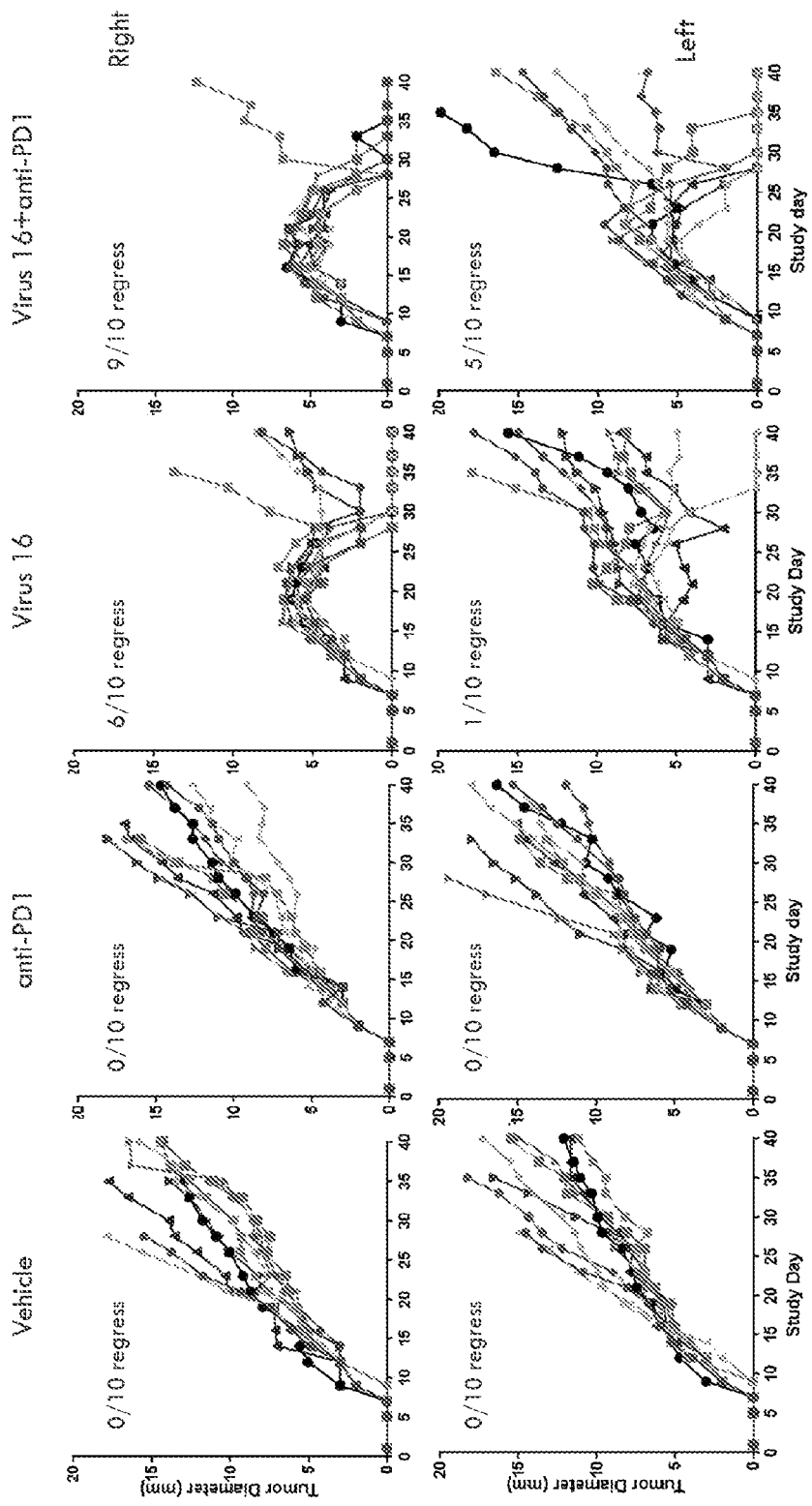

Groups of 10 mice were then treated with:
Vehicle (3 injections into right flank tumors every other day);
5×10 exp 6 pfu of Virus 16 injected in the right flank tumor every other day;
anti-mousePD1 alone (10 mg/kg i.p. every three days, BioXCell clone RMP1-14);
anti-mouseCTLA-4 (3 mg/Kg i.p every three days, BioX-Cell clone 9D9);
anti-mousePD1 together with Virus 16;
anti-mouseCTLA4 together with Virus 16;
1-methyl trypotophan (IDO inhibitor (5 mg/ml in drinking water));
anti-mouse PD1 together with 1-methyl trypotophan;
anti-mouse PD1 together with 1-methyl trypotophan and Virus 16:

Effects on tumor size were observed for a further 30 days. A greater tumor reduction in animals treated with combinations of virus and checkpoint blockade was demonstrated than in animals treated with the single treatment groups (see FIGS. 11A-11C). Enhanced tumor reduction with Virus 16 together with both anti-PD1 and IDO inhibition was also demonstrated as compared to Virus 16 together with only anti-PD1 (see FIGS. 11A-11C).

Enhanced activity of Virus 16 in combination with immune checkpoint blockade was also seen in A20 tumors (FIGS. 12A-12D).

Example 14. The Effect of the Expression of a Fusogenic Protein from an Oncolytic Virus of the Invention in Human Xenograft Models in Immune Deficient Mice The GALV R- protein causes cell to cell fusion in human cells but not in mouse cells. However, human xenograft tumors grown in immune deficient mice can be used to assess the effects of GALV expression on anti-tumor efficacy.

The utility of the invention was therefore further demonstrated by administering A549 human lung cancer cells into the flanks of nude mice and allowing the tumors to grow to approximately 0.5 cm in diameter.

The following treatments were then administered to groups of mice (ten per group), into tumor containing flank of each mouse three times over one week:
50 µl of vehicle;
50 µl of $10^7$ pfu/ml of Virus 16 (expresses both mouse GM-CSF and GALV-R-);
50 µl of $10^6$ pfu/ml of Virus 16;
50 µl of $10^5$ pfu/ml of Virus 16;
50 µl of $10^7$ pfu/ml of Virus 19 (expresses only mouse GM-CSF);
50 µl of $10^6$ pfu/ml of Virus 19;
50 µl of $10^5$ pfu/ml of Virus 19.

Figure 14:
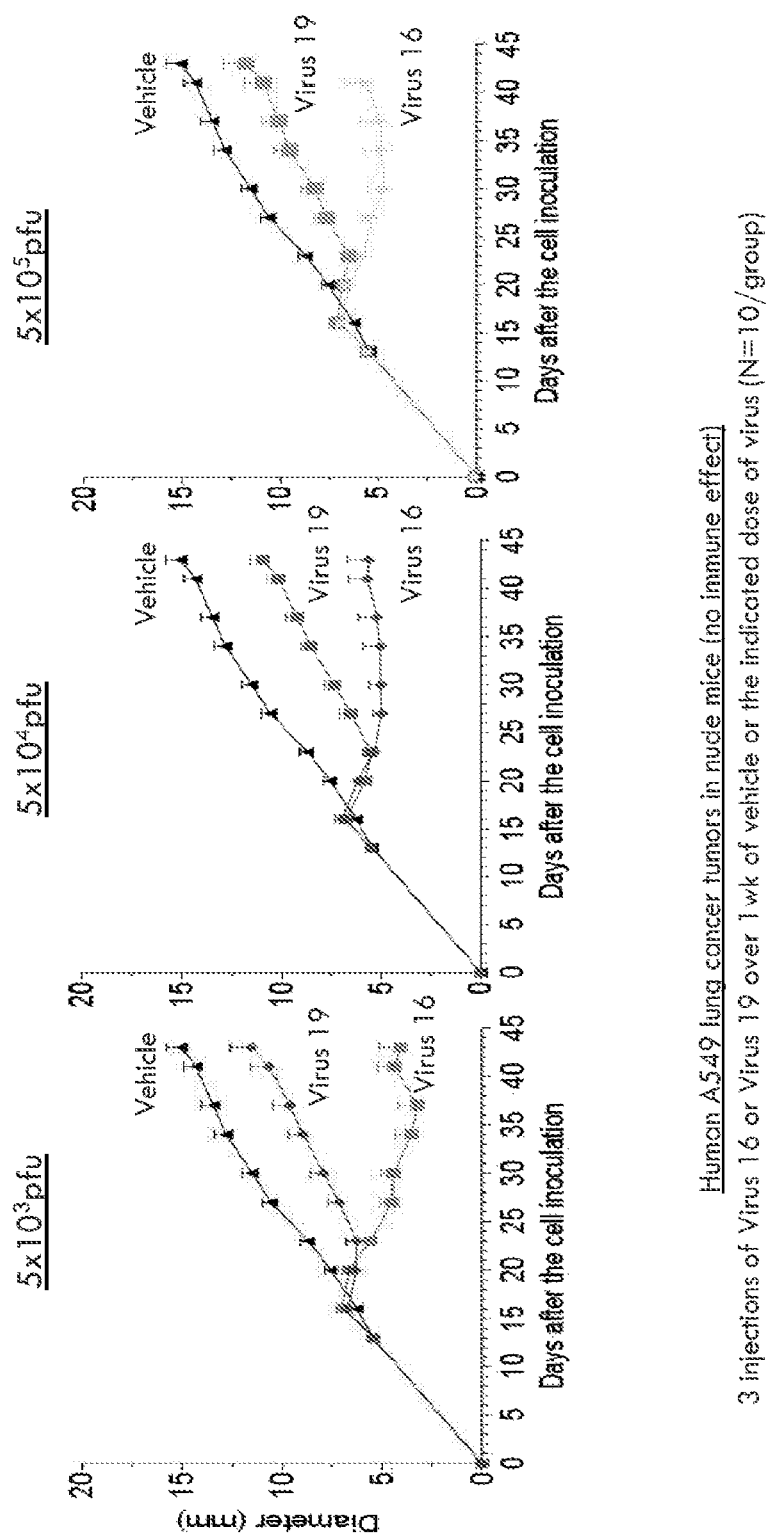
FIG. 14 shows anti-tumor effects of Virus 16 and Virus 19 in a human xenograft model (A549). There were three injections of Virus 16, Virus 19 or of vehicle over one week at three different dose levels (N=10/group). The doses of the viruses used is indicated. The anti-tumor effects of Virus 16 which expresses GALV were better than those of Virus 19 which does not express GALV.

Effects on tumor growth were then observed for a further 30 days. This experiment demonstrated superior tumor control and shrinkage with the virus expressing GALV-R- in both tumor models (see FIG. 14).

Figure 13:
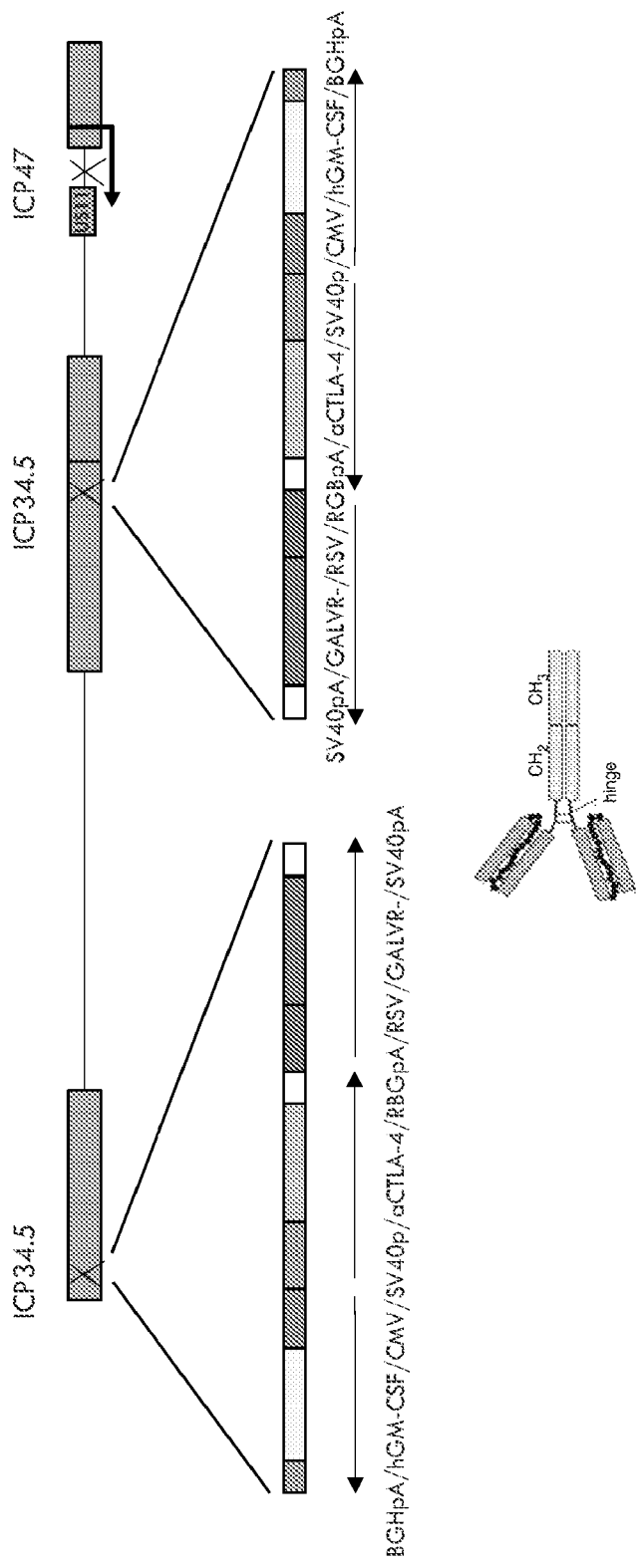
FIG. 13 shows the structure of ICP34.5 and ICP47 deleted viruses expressing GALVR-, GM-CSF and codon optimized anti-mouse or anti-human CTLA-4 antibody constructs (secreted scFv molecules linked to human or mouse IgG1 Fc regions). The scFvs contain the linked ([G$_4$S]$_3$) light and heavy variable chains from antibody 9D9 (US2011044953: mouse version) and from ipilimumab (US20150283234; human version). The resulting structure of the CTLA-4 inhibitor is also shown.
Figure 16:
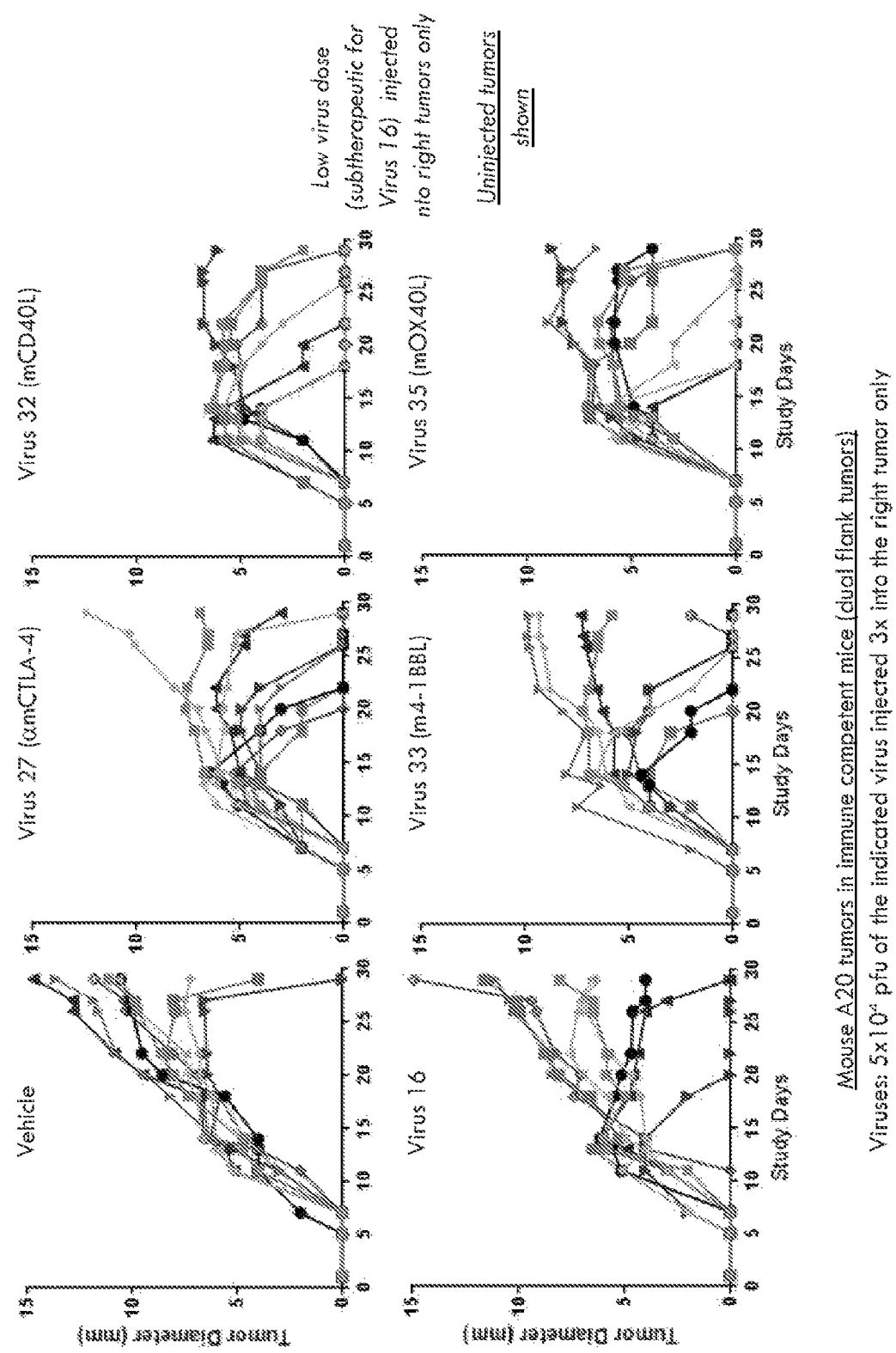
FIG. 16 shows the anti-tumor effects of viruses expressing anti-mCTLA-4 (virus 27), mCD40L (virus 32), mOX4OL (virus 35), m4-2BBL (virus 33), each also with mGM-CSF and GALV-R- compared to virus 16 (expresses GALV and mGM-CSF).

Example 15. Expression of Two Immune Stimulatory Molecules from a Virus Expressing a Fusogenic Protein Viruses similar to the GALV-R- and mGM-CSF expressing virus described above (Virus 16) were constructed, but additionally expressing mouse versions of CD40L (virus 32), ICOSL (virus 36), OX40L (virus 35), 4-1BBL (virus 33) and GITRL (virus 34). Here, instead of using a plasmid containing ICP34.5 flanking regions and an expression cassette comprising GM-CSF and GALV-R- driven by a CMV and an RSV promoter, a plasmid containing ICP34.5 flanking regions and an expression cassette comprising GM-CSF, GALV and the additional proteins driven by a CMV, an RSV and an MMLV promoter respectively were used for recombination with a virus containing GM-CSF, GALV and GFP inserted into ICP34.5. Non-GFP expressing plaques were again selected. Correct insertion was confirmed by PCR, and expression by western blotting and/or ELISA for the additional inserted gene. These viruses are shown in FIGS. 5A-5K. Similarly, viruses expressing anti-mouse and anti-human CTLA-4 in addition to GALV and mGM-CSF were also constructed (Viruses 27 and 31 in FIGS. 5A-5K and see also FIG. 13). Effects of viruses expressing anti-mouse CTLA-4 (virus 27), mCD40L (virus 32), m4-1BBL (virus 33) or mOX40L (virus 35) in addition to mGM-CSF and GALVR- in vivo is shown in FIG. 16 which showed enhanced activity in A20 tumors as compared to virus 16 (expresses mGM-CSF and GALVR-). In these experiments tumors were induced in both flanks of mice, and virus or vehicle injected only into the right flank tumor. The dose of virus used was $5 \times 10^4$ pfu (50 ul of $1 \times 10^6$ pfu/ml in each case), given three times over one week. This dose level of virus is subtherapeutic for uninjected tumors for virus 16, which allows the benefits of the delivery of the additional molecules encoded by viruses 27, 32, 33 and 35 to clearly be seen.

DEPOSIT INFORMATION

The following HSV1 strains were deposited at the ECACC, Culture Collections. Public Health England. Porton Down, Salisbury, SP4 0JG, United Kingdom on 19 Dec. 2016 by Replimune Limited and were allocated the indicated provisional accession numbers:
RH004A-Provisional Accession Number 16121902
RH015A-Provisional Accession Number 16121903
RH018A-Provisional Accession Number 16121904
RH021A-Provisional Accession Number 16121905
RH023A-Provisional Accession Number 16121906
RH031A-Provisional Accession Number 16121907
RH040B-Provisional Accession Number 16121908
RH047A-Provisional Accession Number 16121909.

The invention claimed is:

1. A method of treating cancer, comprising administering a therapeutically effect amount of an oncolytic virus and a programmed cell death protein 1 (PD-1) inhibitor to a patient in need thereof,
   wherein the oncolytic virus is a herpes simplex virus 1 (HSV1)
      strain RH018A having the accession number ECACC 16121904;
      strain RH004A having the accession number ECACC 16121902;
      strain RH031A having the accession number ECACC 16121907;
      strain RH040B having the accession number ECACC 16121908;
      strain RH015A having the accession number ECACC 16121903;
      strain RH021A having the accession number ECACC 16121905;
      strain RH023A having the accession number ECACC 16121906; or
      strain RH047A having the accession number ECACC 16121909;
   wherein said virus is modified to comprise:
   (1) one or more mutations in one or more viral genes, wherein the one or more mutations result in inhibited replication in normal tissue but still allow replication in tumors;
   (2) one or more immune stimulatory molecule-encoding genes; and/or
   (3) one or more fusogenic protein-encoding genes.

2. The method of claim 1, wherein the oncolytic virus is a HSV1 strain RH018A having the provisional accession number ECACC 16121904 modified to:
   (1) comprise one or more mutations in one or more viral genes, wherein the one or more mutations result in inhibited replication in normal tissue but still allow replication in tumors;
   (2) one or more immune stimulatory molecule-encoding genes; and/or
   (3) one or more fusogenic protein-encoding genes.

3. The method of claim 1, wherein the virus:
   (a) does not express functional ICP34.5;
   (b) does not express functional ICP47; and/or
   (c) expresses the US11 gene as an immediate early gene.

4. The method of claim 1, wherein
   the fusogenic protein is selected from the group consisting of vesicular stomatitis virus (VSV) G-protein, syncitin-1, syncitin-2, simian virus 5 (SV5) F-protein, measles virus (MV) H-protein, MV F-protein, respiratory syncytial virus (RSV) F-protein and a glycoprotein from gibbon ape leukemia virus (GALV), murine leukemia virus (MLV), Mason-Pfizer monkey virus (MPMV) or equine infectious anaemia virus (EIAV) from which the R peptide has been deleted.

5. The method of claim 1, wherein the one or more immune stimulatory molecules comprise
   GM-CSF, IL-2, IL-12, IL-15, IL-18, IL-21, IL-24, a type I interferon, interferon gamma, a type III interferon, TNF alpha, an antagonist of TGF beta, an immune checkpoint antagonist and/or an agonist of an immune potentiating pathway including CD40 ligand (CD40L), inducible T cell costimulator (ICOS) ligand, glucocorticoid-induced tumour necrosis factor receptor-related (GITR) ligand, 4-1-BB ligand, OX40 ligand and/or FMS-like tyrosine kinase 3 (flt3) ligand.

6. The method of claim 1, wherein
   the fusogenic protein-encoding gene and/or the immune stimulatory molecule-encoding gene are inserted into the ICP34.5 encoding locus, either by insertion, or partial or complete deletion, each under separate regulatory control, optionally in a back to back orientation in relation to each other.

7. The method of claim 1, wherein the virus expresses:
   (a) three heterologous genes, wherein each of the three heterologous genes is driven by a different promoter selected from the CMV promoter, the RSV promoter, the SV40 promoter and a retroviral LTR promoter, and/or terminated by a different poly adenylation sequence selected from the bovine growth hormone (BGH), SV40, human growth hormone (HGH) and rabbit beta-globin (RBG) poly adenylation sequences; or
   (b) four heterologous genes driven by each of the CMV promoter, the RSV promoter, the SV40 promoter and a retroviral LTR promoter, respectively, and/or terminated by a different poly adenylation sequence selected from the bovine growth hormone (BGH), SV40, human growth hormone (HGH) and rabbit beta-globin (RBG) poly adenylation sequences.

8. The method of claim 1, wherein the PD-1 inhibitor is an antibody.

9. The method of claim 1, wherein the virus and the PD-1 inhibitor are administered separately or concurrently.

10. The method of claim 1, wherein the cancer is a solid tumor and/or a metastatic cancer.

11. The method of claim 1, wherein the oncolytic virus is administered at a dose of between $10^4$ and $10^7$ pfu.

12. The method of using an oncolytic virus of claim 1, wherein the oncolytic virus is administered at an initial dose of between $10^4$ and $10^7$ pfu and further administered at a higher dose than the initial dose, wherein the higher dose is between $10^6$ and $10^9$ pfu.

13. The method of claim 1, wherein the oncolytic virus is administered directly into a tumor.

14. The method of claim 1, wherein the fusogenic protein is a glycoprotein from gibbon ape leukemia virus (GALV) and has the R transmembrane peptide mutated or removed (GALV-R-).

15. The method of claim 1, wherein the one or more immune stimulatory molecules comprise GM-CSF.

16. The method of claim 1, wherein the one or more immune stimulatory molecules comprise GM-CSF and a cytotoxic T-lymphocyte-associated antigen 4 (CTLA-4) inhibitor.

17. The method of claim 1, wherein the one or more immune stimulatory molecules comprise a CTLA-4 inhibitor and one or more of an agonist of CD40, an agonist of 4-1-BB, an agonist of glucocorticoid-induced tumour necrosis factor receptor-related (GITR), an agonist of OX40, an agonist of inducible T cell costimulator (ICOS) and an agonist of FMS-like tyrosine kinase 3 (flt3).

18. The method of claim 1, wherein the fusogenic protein is a glycoprotein from gibbon ape leukemia virus (GALV) and has the R transmembrane peptide mutated or removed (GALV-R-), and wherein the one or more immune stimulatory molecules comprise GM-CSF.

19. The method of claim 1, wherein the fusogenic protein is a glycoprotein from gibbon ape leukemia virus (GALV) and has the R transmembrane peptide mutated or removed (GALV-R-), and wherein the one or more immune stimulatory molecules comprise GM-CSF and a CTLA-4 inhibitor.

20. The method of claim 1, wherein the fusogenic protein is a glycoprotein from gibbon ape leukemia virus (GALV)

and has the R transmembrane peptide mutated or removed (GALV-R-), and wherein the one or more immune stimulatory molecules comprise a CTLA-4 inhibitor, CD40 ligand, and 4-1-BB ligand.

21. The method of claim 1, wherein the sequence of the gene encoding the fusogenic protein and/or the sequence of the gene encoding the immune stimulatory molecule is codon optimized so as to increase expression levels in target cells.

22. The method of claim 16, wherein the cytotoxic T-lymphocyte-associated antigen 4 (CTLA-4) inhibitor is a CTLA-4 antibody of a fragment thereof.

23. A method of using an oncolytic virus, comprising administering a therapeutically effect amount of an oncolytic virus and a PD-1 inhibitor to a patient in need thereof,
wherein the oncolytic virus is a herpes simplex virus 1 (HSV1)
strain RH018A having the accession number ECACC 16121904;
strain RH004A having the accession number ECACC 16121902;
strain RH031 A having the accession number ECACC 16121907;
strain RH040B having the accession number ECACC 16121908;
strain RH015A having the accession number ECACC 16121903;
strain RH021A having the accession number ECACC 16121905;
strain RH023A having the accession number ECACC 16121906; or
strain RH047A having the accession number ECACC 16121909;
wherein said virus is modified to comprise:
(1) one or more mutations in one or more viral genes, wherein the one or more mutations result in inhibited replication in normal tissue but still allow replication in tumors;
(2) one or more immune stimulatory molecule encoding genes; and/or
(3) one or more fusogenic protein-encoding genes.

24. The method of using an oncolytic virus of claim 23, wherein the oncolytic virus is administered at a dose between $10^4$ and $10^7$ pfu.

25. The method of using an oncolytic virus of claim 23, wherein the oncolytic virus is administered at an initial dose of between $10^4$ and $10^7$ pfu and further administered at a higher dose than the initial dose, wherein the higher dose is between $10^6$ and $10^9$ pfu.

26. The method of using an oncolytic virus of claim 23, wherein the oncolytic virus is administered directly into a tumor.

27. A method of treating a patient, comprising administering a therapeutically effect amount of an oncolytic virus and a PD-1 inhibitor to a patient in need thereof,
wherein the oncolytic virus is a herpes simplex virus 1 (HSV1)
strain RH018A having the accession number ECACC 16121904;
strain RH004A having the accession number ECACC 16121902;
strain RH031A having the accession number ECACC 16121907;
strain RH040B having the accession number ECACC 16121908;
strain RH015A having the accession number ECACC 16121903;
strain RH021 A having the accession number ECACC 16121905;
strain RH023A having the accession number ECACC 16121906; or
strain RH047A having the accession number ECACC 16121909;
wherein said virus is modified to comprise:
(1) one or more mutations in one or more viral genes, wherein the one or more mutations result in inhibited replication in normal tissue but still allow replication in tumors;
(2) one or more immune stimulatory molecule encoding genes; and/or
(3) one or more fusogenic protein-encoding genes.

28. The method of treating a patient of claim 27, wherein the oncolytic virus is administered at a dose between $10^4$ and $10^7$ pfu.

29. The method of treating a patient of claim 27, wherein the oncolytic virus is administered at an initial dose of between $10^4$ and $10^7$ pfu and further administered at a higher dose than the initial dose, wherein the higher dose is between $10^6$ and $10^9$ pfu.

30. The method of treating a patient of claim 27, wherein the oncolytic virus is administered directly into a tumor.

* * * * *